United States Patent
Matsukura

(10) Patent No.: US 8,513,287 B2
(45) Date of Patent: Aug. 20, 2013

(54) HETEROCYCLIC RING AND PHOSPHONOXYMETHYL GROUP SUBSTITUTED PYRIDINE DERIVATIVES AND ANTIFUNGAL AGENT CONTAINING SAME

(75) Inventor: Masayuki Matsukura, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 12/343,889

(22) Filed: Dec. 24, 2008

(65) Prior Publication Data

US 2009/0233883 A1 Sep. 17, 2009

Related U.S. Application Data

(60) Provisional application No. 61/017,053, filed on Dec. 27, 2007.

(30) Foreign Application Priority Data

Dec. 27, 2007 (JP) ................................. 2007-336977

(51) Int. Cl.
*A61K 31/445* (2006.01)
*C07D 401/00* (2006.01)

(52) U.S. Cl.
USPC .......................................... 514/333; 546/256

(58) Field of Classification Search
USPC .......................................... 514/333; 546/256
See application file for complete search history.

(56) References Cited

U.S. PATENT DOCUMENTS

| | | | |
|---|---|---|---|
| 4,551,532 A | 11/1985 | Hozumi et al. | |
| 4,576,956 A | 3/1986 | Makisumi et al. | |
| 4,720,493 A | 1/1988 | Kawakita et al. | |
| 4,785,010 A | 11/1988 | Zoller et al. | |
| 4,935,520 A | 6/1990 | Nojima et al. | |
| 5,034,393 A | 7/1991 | Hackler et al. | |
| 5,068,340 A | 11/1991 | Nakamura et al. | |
| 5,070,082 A | 12/1991 | Murdock et al. | |
| 5,208,247 A | 5/1993 | Trova et al. | |
| 5,296,484 A | 3/1994 | Coghlan et al. | |
| 5,328,921 A | 7/1994 | Trova et al. | |
| 5,350,749 A | 9/1994 | Hackler et al. | |
| 5,371,086 A | 12/1994 | Takemoto et al. | |
| 5,691,136 A | 11/1997 | Lupski et al. | |
| 5,691,336 A | 11/1997 | Dorn et al. | |
| 5,710,171 A | 1/1998 | Dinsmore et al. | |
| 5,747,518 A | 5/1998 | Yoshikawa et al. | |
| 5,852,042 A | 12/1998 | Jakobi et al. | |
| 5,945,431 A | 8/1999 | Jin et al. | |
| 5,985,856 A * | 11/1999 | Stella et al. ...................... | 514/80 |
| 6,022,884 A | 2/2000 | Mantlo et al. | |
| 6,080,767 A | 6/2000 | Klein et al. | |
| 6,140,131 A | 10/2000 | Sunakawa et al. | |
| 6,174,905 B1 | 1/2001 | Suzuki et al. | |
| 6,200,975 B1 | 3/2001 | Carling et al. | |
| 6,235,728 B1 * | 5/2001 | Golik et al. ...................... | 514/93 |
| 6,255,318 B1 | 7/2001 | Bedard et al. | |
| 6,262,039 B1 | 7/2001 | Hillebrand et al. | |
| 6,310,203 B1 | 10/2001 | Carling et al. | |
| 6,313,127 B1 | 11/2001 | Waterson et al. | |
| 6,319,944 B1 | 11/2001 | Claiborne et al. | |
| 6,340,690 B1 | 1/2002 | Bachand et al. | |
| 6,369,044 B1 | 4/2002 | Hillebrand et al. | |
| 6,380,218 B1 | 4/2002 | Marfat et al. | |
| 6,407,116 B1 | 6/2002 | Kajino et al. | |
| 6,414,013 B1 | 7/2002 | Fancelli et al. | |
| 6,596,718 B1 | 7/2003 | Flohr et al. | |
| 6,630,495 B1 | 10/2003 | Cooke et al. | |

(Continued)

FOREIGN PATENT DOCUMENTS

AU 2006309762 B2 2/2010
DE 197 32 033 A1 1/1999

(Continued)

OTHER PUBLICATIONS

Accession No. 2020895193, Chemcats, Interchim Intermediates, Jul. 9, 2007, TK030913, Pyridine, 3-[3-[(4-methoxyphenyl)methyl]-1,2,4-oxadiazol-5-yl]-, 438574-99-3.

Accession No. 2021278791, Chemcats, Akos Screening Library, Feb. 7, 2006, AKL-P-1720927, Pyridine, 3-[5-[(2-methoxyphenyl)methyl]-1,2,4-oxadiazol-3-yl]- CAS Registry No. 434304-24-2.

Accession No. 2025887145, Chemcats, Aurora Screening Library, kbsa-0118093, Pyridine, 3-[5-[(4-methoxyphenyl)methyl]-1,2,4-oxadiazol-3-yl]-, 431922-54-2, Jan. 1, 2007.

Accession No. 2036647688, Chemcats, Ambinter Stock Screening Collection, STK143803, Pyridine, 3-[5-[(4-methoxyphenyl)methyl]-1,2,4-thiadiazol-2-yl]-, 794713-41-9, Jun. 1, 2007.

(Continued)

*Primary Examiner* — D M Seaman
*Assistant Examiner* — Heidi Reese
(74) *Attorney, Agent, or Firm* — Birch, Stewart, Kolasch & Birch, LLP

(57) ABSTRACT

The present invention provides compounds that have excellent antifungal action, and are also excellent in terms of properties, such as solubility in water and safety. The compounds are represented by formula (I):

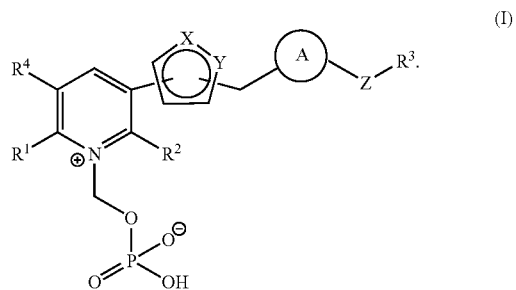

The present invention is also directed to a pharmaceutical composition comprising the compound, an antifungal agent comprising the compound as an active ingredient, and a method for preventing or treating a fungal disease by administering the compound.

3 Claims, 16 Drawing Sheets

(56) References Cited

U.S. PATENT DOCUMENTS

| | | |
|---|---|---|
| 7,179,804 B2 | 2/2007 | Amegadize et al. |
| 7,179,822 B2 | 2/2007 | Bunker et al. |
| 7,687,525 B2 | 3/2010 | Suzuki et al. |
| 7,691,882 B2 * | 4/2010 | Tanaka et al. ............... 514/333 |
| 7,754,726 B2 | 7/2010 | Lang et al. |
| 7,829,585 B2 | 11/2010 | Nakamoto et al. |
| 7,932,272 B2 | 4/2011 | Nakamoto et al. |
| 8,188,119 B2 | 5/2012 | Tanaka |
| 2002/0011495 A1 | 1/2002 | Clemmons |
| 2002/0111495 A1 | 8/2002 | Magee et al. |
| 2002/0132813 A1 | 9/2002 | Schaper et al. |
| 2003/0045554 A1 | 3/2003 | Sankaranarayanan |
| 2003/0114491 A1 | 6/2003 | Kim et al. |
| 2003/0191158 A1 | 10/2003 | Magee |
| 2003/0195169 A1 | 10/2003 | Gillman et al. |
| 2004/0010145 A1 | 1/2004 | Schaper et al. |
| 2004/0038239 A1 | 2/2004 | Tsukahara et al. |
| 2004/0044040 A1 | 3/2004 | Neubert et al. |
| 2004/0152730 A1 | 8/2004 | Farina et al. |
| 2004/0198773 A1 | 10/2004 | Hart et al. |
| 2005/0119229 A1 | 6/2005 | Ammermann et al. |
| 2006/0264419 A1 | 11/2006 | Schiemann et al. |
| 2006/0270637 A1 | 11/2006 | Gravestock et al. |
| 2007/0060619 A1 | 3/2007 | Burns et al. |
| 2007/0105904 A1 | 5/2007 | Tanaka et al. |
| 2007/0105943 A1 | 5/2007 | Nakamoto et al. |
| 2007/0167493 A1 | 7/2007 | Sankaranarayanan |
| 2008/0090846 A1 | 4/2008 | Bridger et al. |
| 2008/0275244 A1 | 11/2008 | Niijima et al. |
| 2009/0062348 A1 | 3/2009 | Nakamoto et al. |
| 2009/0082403 A1 | 3/2009 | Tanaka et al. |
| 2009/0084621 A1 | 4/2009 | Giovannini et al. |
| 2009/0227799 A1 | 9/2009 | Nakamoto et al. |
| 2010/0099718 A1 | 4/2010 | Matsukura et al. |
| 2010/0105737 A1 | 4/2010 | Tanaka |
| 2010/0160379 A1 | 6/2010 | Tanaka et al. |
| 2010/0168173 A1 | 7/2010 | Tanaka et al. |
| 2010/0331282 A1 | 12/2010 | Matsukura |
| 2011/0195999 A1 | 8/2011 | Nakamoto et al. |
| 2011/0201496 A1 | 8/2011 | Rheinheimer et al. |

FOREIGN PATENT DOCUMENTS

| | | |
|---|---|---|
| DE | 19727117 | 1/1999 |
| DE | 19727117 A1 | 1/1999 |
| EA | 200601880 A1 | 2/2007 |
| EA | 1 944 303 A1 | 7/2008 |
| EP | 0124067 | 11/1984 |
| EP | 0124067 A1 | 11/1984 |
| EP | 0124154 | 11/1984 |
| EP | 0124154 A2 | 11/1984 |
| EP | 0274867 | 7/1988 |
| EP | 0274867 A2 | 7/1988 |
| EP | 0326328 | 8/1989 |
| EP | 0326328 A2 | 8/1989 |
| EP | 0414386 | 2/1991 |
| EP | 0414386 A1 | 2/1991 |
| EP | 0533130 | 3/1993 |
| EP | 0533130 A1 | 3/1993 |
| EP | 0976744 | 2/2000 |
| EP | 0976744 A1 | 2/2000 |
| EP | 1216980 | 6/2002 |
| EP | 1216980 A1 | 6/2002 |
| EP | 1217000 | 6/2002 |
| EP | 1217000 A1 | 6/2002 |
| EP | 1229034 | 8/2002 |
| EP | 1229034 A1 | 8/2002 |
| EP | 1275301 | 1/2003 |
| EP | 1275301 A1 | 1/2003 |
| EP | 1275653 | 1/2003 |
| EP | 1275653 A1 | 1/2003 |
| EP | 1 369 420 A1 | 12/2003 |
| EP | 1 669 348 A1 | 6/2006 |
| EP | 1782811 | 5/2007 |
| EP | 1782811 A1 | 5/2007 |
| GB | 919073 | 2/1963 |
| JP | 54-2325 | 1/1979 |
| JP | 54-2325 A | 1/1979 |
| JP | 57-179192 A | 11/1982 |
| JP | 59-73575 | 4/1984 |
| JP | 59-73575 A | 4/1984 |
| JP | 59-84824 A | 5/1984 |
| JP | 59-206353 | 11/1984 |
| JP | 59-206353 A | 11/1984 |
| JP | 61-148178 | 7/1986 |
| JP | 61-148178 A | 7/1986 |
| JP | 62-277368 A | 12/1987 |
| JP | 64-3162 | 1/1989 |
| JP | 64-3162 A | 1/1989 |
| JP | 1-246264 | 10/1989 |
| JP | 1-246264 A | 10/1989 |
| JP | 1-261381 A | 10/1989 |
| JP | 3-66689 | 3/1991 |
| JP | 3-66689 A | 3/1991 |
| JP | 3-161470 | 7/1991 |
| JP | 3-161470 A | 7/1991 |
| JP | 5-213877 A | 8/1993 |
| JP | 5-294935 | 11/1993 |
| JP | 5-294935 A | 11/1993 |
| JP | 7-25853 | 1/1995 |
| JP | 7-25853 A | 1/1995 |
| JP | 7-502503 A | 3/1995 |
| JP | 8-12579 A | 1/1996 |
| JP | 8-175993 | 7/1996 |
| JP | 8-175993 A | 7/1996 |
| JP | 9-507245 A | 7/1997 |
| JP | 10-505600 | 6/1998 |
| JP | 10-505600 A | 6/1998 |
| JP | 11-152275 A | 6/1999 |
| JP | 2000-504336 | 4/2000 |
| JP | 2000-504336 A | 4/2000 |
| JP | 2000-178243 | 6/2000 |
| JP | 2000-178243 A | 6/2000 |
| JP | 2001-515464 A | 9/2001 |
| JP | 2001-522834 | 11/2001 |
| JP | 2001-522834 A | 11/2001 |
| JP | 2001-525365 A | 12/2001 |
| JP | 2001-525802 A | 12/2001 |
| JP | 2001-527083 A | 12/2001 |
| JP | 2002-275159 | 9/2002 |
| JP | 2002-275159 A | 9/2002 |
| JP | 2002-284766 | 10/2002 |
| JP | 2002-284766 A | 10/2002 |
| JP | 2002-537396 A | 11/2002 |
| JP | 2002-544162 A | 12/2002 |
| JP | 2003-506466 | 2/2003 |
| JP | 2003-506466 A | 2/2003 |
| JP | 2004-505967 A | 2/2004 |
| JP | 20047-505967 A | 2/2004 |
| JP | 2004-529154 | 9/2004 |
| JP | 2004-529154 A | 9/2004 |
| JP | 2005-33079 | 2/2005 |
| JP | 2005-33079 A | 2/2005 |
| JP | 2005-526097 A | 9/2005 |
| JP | 2005-526751 | 9/2005 |
| JP | 2005-526751 A | 9/2005 |
| JP | 2006-519247 | 8/2006 |
| JP | 2006-519247 A | 8/2006 |
| WO | WO 86/03203 | 6/1986 |
| WO | WO 86/03203 A1 | 6/1986 |
| WO | WO 93/07136 A1 | 4/1993 |
| WO | 93/12124 A1 | 6/1993 |
| WO | WO 93/12064 A1 | 6/1993 |
| WO | WO 93/12084 | 6/1993 |
| WO | 95/09159 A1 | 4/1995 |
| WO | 95/18795 A1 | 7/1995 |
| WO | WO 96/09294 | 3/1996 |
| WO | WO 96/09294 A1 | 3/1996 |
| WO | WO 97/27852 | 8/1997 |
| WO | WO 97/27852 A1 | 8/1997 |
| WO | WO 97/28128 | 8/1997 |
| WO | WO 97-28128 A1 | 8/1997 |
| WO | WO 98/25883 | 6/1998 |
| WO | WO 98/25883 A1 | 6/1998 |
| WO | WO 98/50029 | 11/1998 |

| | | |
|---|---|---|
| WO | WO 98/50029 A1 | 11/1998 |
| WO | WO 99/24404 | 5/1999 |
| WO | WO 99/24404 A1 | 5/1999 |
| WO | WO 99/48492 | 9/1999 |
| WO | WO 99/48492 A1 | 9/1999 |
| WO | WO 99/50247 | 10/1999 |
| WO | WO 99/50247 A1 | 10/1999 |
| WO | WO 00/07991 | 2/2000 |
| WO | WO 00/07991 A1 | 2/2000 |
| WO | WO 00/51996 | 9/2000 |
| WO | WO 00/51998 A1 | 9/2000 |
| WO | WO 00/62278 A1 | 10/2000 |
| WO | WO 00/62778 | 10/2000 |
| WO | WO 00/73283 | 12/2000 |
| WO | WO 00/73283 A1 | 12/2000 |
| WO | WO 01/11966 | 2/2001 |
| WO | WO 01/11966 A1 | 2/2001 |
| WO | WO 01/21584 | 3/2001 |
| WO | WO 01/21584 A1 | 3/2001 |
| WO | 01/26652 A1 | 4/2001 |
| WO | WO 01/25181 | 4/2001 |
| WO | WO 01/25181 A1 | 4/2001 |
| WO | WO 01/27096 | 4/2001 |
| WO | WO 01/27096 A1 | 4/2001 |
| WO | WO 01/36003 A2 | 5/2001 |
| WO | WO 01/51456 | 7/2001 |
| WO | WO 01/51456 A2 | 7/2001 |
| WO | WO 01/53274 | 7/2001 |
| WO | WO 01/53274 A1 | 7/2001 |
| WO | WO 01/74779 | 10/2001 |
| WO | WO 01/74779 A1 | 10/2001 |
| WO | WO 02/00651 | 1/2002 |
| WO | WO 02/00651 A2 | 1/2002 |
| WO | WO-02/04626 A1 | 1/2002 |
| WO | WO 02/06275 | 1/2002 |
| WO | WO 02/06275 A1 | 1/2002 |
| WO | WO 02/22583 | 3/2002 |
| WO | WO 02/22583 A2 | 3/2002 |
| WO | WO 02/060875 | 8/2002 |
| WO | WO 02/060875 A1 | 8/2002 |
| WO | WO 02/060896 | 8/2002 |
| WO | WO 02/060896 A1 | 8/2002 |
| WO | WO 02/060898 | 8/2002 |
| WO | WO 02/060898 A1 | 8/2002 |
| WO | WO 02/083645 | 10/2002 |
| WO | WO 02/083645 A1 | 10/2002 |
| WO | WO 02/085897 | 10/2002 |
| WO | WO 02/085897 A1 | 10/2002 |
| WO | 03/006628 A2 | 1/2003 |
| WO | WO 03/027095 | 4/2003 |
| WO | WO 03/027095 A1 | 4/2003 |
| WO | WO 03/031435 | 4/2003 |
| WO | WO 03/031435 A1 | 4/2003 |
| WO | 03/037860 A2 | 5/2003 |
| WO | 03/045920 A1 | 6/2003 |
| WO | WO 03/045385 | 6/2003 |
| WO | WO 03/045385 A1 | 6/2003 |
| WO | WO 03/059903 | 7/2003 |
| WO | WO 03/059903 A2 | 7/2003 |
| WO | 03/068747 A1 | 8/2003 |
| WO | WO 03/068232 | 8/2003 |
| WO | WO 03/068232 A1 | 8/2003 |
| WO | WO 03/068235 | 8/2003 |
| WO | WO 03/068235 A1 | 8/2003 |
| WO | WO 03/091226 | 11/2003 |
| WO | WO 03/091226 A1 | 11/2003 |
| WO | WO 03/091227 | 11/2003 |
| WO | WO 03/091227 A1 | 11/2003 |
| WO | WO 04/000813 | 12/2003 |
| WO | WO 04/000813 A1 | 12/2003 |
| WO | WO 2004/014366 | 2/2004 |
| WO | WO 2004/014366 A1 | 2/2004 |
| WO | WO 2004/014370 | 2/2004 |
| WO | WO 2004/014370 A2 | 2/2004 |
| WO | WO 2004/029027 | 4/2004 |
| WO | WO 2004/029027 A1 | 4/2004 |
| WO | WO 2004/033432 | 4/2004 |
| WO | WO 2004/033432 A1 | 4/2004 |
| WO | WO 2004/048567 | 6/2004 |
| WO | WO 2004/048567 A2 | 6/2004 |
| WO | WO 2004/052280 | 6/2004 |
| WO | WO 2004/052280 A2 | 6/2004 |
| WO | WO 2004/089931 | 10/2004 |
| WO | WO 2004/089931 A1 | 10/2004 |
| WO | WO-2005/033079 A1 | 4/2005 |
| WO | WO 2005/097774 A1 | 10/2005 |
| WO | WO 2006/006711 | 1/2006 |
| WO | WO 2006/106711 A1 | 1/2006 |
| WO | WO 2006/016548 | 2/2006 |
| WO | WO 2006-016548 A1 | 2/2006 |
| WO | WO 2007/052615 A1 | 5/2007 |
| WO | WO-2007/052615 A1 | 5/2007 |
| WO | WO 2007/056215 A2 | 5/2007 |
| WO | WO 2008/070149 A2 | 6/2008 |
| WO | 2008/136324 A1 | 11/2008 |
| WO | WO 2009/081970 | 7/2009 |
| WO | WO 2009/081970 A1 | 7/2009 |
| WO | WO 2009/084621 | 7/2009 |
| WO | WO 2009-084621 A1 | 7/2009 |

OTHER PUBLICATIONS

Chan et al., Database Accession No. 8422493, Abstract, Bioorganic & Medicinal Chemistry Letters, 1999, pp. 2583-2586., vol. 9, No. 17, Database Crossfire Beilstein, Beilstein Institut Zur Foerderung Der Chemischen Wissenschaften, Frankfurt Am Main, DE, XP-002512523.

Chang, K. Y. et al., "Synthesis and Structure-Activity Relationships of Quaternary Ammonium Cephalosporins with 3-Pyrazolylpyridinium Derivatives," Bioorganic & Medicinal Chemistry Letters (2000) vol. 10, No. 11, pp. 1211-1214.

Connors et al., "Prodrugs in medicine," Overview, Biologicals & Immunologicals, Exp. Opin. Ther. Patents, vol. 5, No. 9, 1995, pp. 873-885.

Office Action from co-pending U.S. Appl. No. 10/573,890, mailed Jul. 29, 2009.

Gardner et al., "Genome sequence of the human malaria parasite *Plasmodium falciparum*," Nature, vol. 419, pp. 498-511, (2002).

Guillory, "Generation of Polymorphs, Hydrates, Solvates, and Amorphous Solids", Polymorphism in Pharmaceutical Solids, 1999, pp. 183-226, ed. Harry G. Brittain, Marcel Dekker, Inc., New York.

Ikizler, et al, "Antimicrobial activities of some 4H-1,2,4-triazoles" Indian Journal of Pharmaceutical Sciences, 1999, vol. 61, No. 5, pp. 271-274.

International Search Report dated May 20, 2008 for corresponding International Application No. PCT/JP2008/057851.

Ishikawa et al., "TAK-599, a Novel N-Phosphono Type Prodrug of Anti-MRSA Cephalosporin T-91825: Synthesis, Physicochemical and Pharmacological Properties," Bioorganic & Medicinal Chemistry, vol. 11, pp. 2427-2437 (2003).

Kajino et al., "Preparation and formulation of quinazoline derivatives as allergy inhibitors", Database CA [Online], Chemical Abstract Service; XP002512525, Database Accession No. 216905, 1999.

Lukevics, E. et al., "Synthesis and cytotoxicity of silyl- and carbonyl-substituted isoxazoles," Chemistry of Heterocyclic Compounds (2000) vol. 36, No. 10, pp. 1226-1231.

Modena et al.: "Plant growth regulating activities of 2-[2-(arylamino)-2-oxoethyl]benzoic acids", Database Accession No. 1993:597690, Abstract, Farmaco, vol. 48, No. 4, pp. 567-572, 1993, XP002512527.

Naik et al., "Glucosamine Inhibits Inositol Acylation of the Glycosylphosphatidylinositol Anchors in Intraerythrocytic *Plasmodium falciparumi*," The Journal of Biological Chemistry, vol. 278, No. 3, pp. 2036-2042, (2003).

Office Action issued May 7, 2009 in co-pending U.S. Appl. No. 11/589,128.

Ohshima et al., "Non-Prostanoid Thromboxane A2 Receptor Antagonists with a Dibenzoxepin Ring System. 2," J. Med. Chem., vol. 35, pp. 3402-3413, (1992).

Okawa et al., "Pyrido[2,3-]pyrimidine Derivatives: Synthesis via the Intermolecular Aza-Wittig Reaction/Heterocyclization and the Crystal Structure," Synthesis, Database CA [Online] Chemical Abstract Service, XP002512524, Database accession No. 677971 (1998), pp. 1467-1475 (1998).

Piechaczak et al., "Monoamine oxidase inhibitors. VII. Derivatives of quinolinecarboxylic acids," Database Accession No. 1966:75701, Abstract, Acta Poloniae Pharmaceutica, vol. 23, No. 1, pp. 7-13, 1966, XP002512526.

Plate, R. et al., "Synthesis and Muscarinic Activities of 3-(Pyrazolyl)-1,2,5,6-tetrahydropyridine Derivatives," Bioorganic & Medicinal Chemistry Letters (1996) vol. 10, No. 2, pp. 227-237.

Satyanarayana, et al., "Studies on the synthesis and biological activity of 3-arylaminomethyl-5-(3-pyridyl)-1, 3, 4-oxadiazole-2-thione derivatives," Bolletino Chimico Farmaceutico, 2001, vol. 140, No. 4, p. 228-232.

Shinkai et al., "N-Acylphenylalanines and Related Compounds. A New Class of Oral Hypoglycemic Agents," J. Med. Chem., vol. 31, pp. 2092-2097, (1988).

Supplementary European Search Report dated Feb. 6, 2009 for corresponding European Application No. 04788159.4.

Tanaka et al., "An Effective Lewis Acid-Mediated 1,3-Dipolar Cycloaddition of Nitrile Oxide Using Acetylene: Synthesis of a (2-Aminopyridin-3-yl) isoxazole Derivative and Its Application to Novel Antifungal Agents," pp. 1-8.

Vippagunta et al., "Crystalline Solids", Advanced Drug Delivery Reviews, 2001, pp. 3-26, vol. 48.

Vrzheschch, P. V. et al., "Supercooperativity in platelet aggregation: Substituted pyridyl isoxazoles, a new class of supercooperative platelet aggregation inhibitors," FEBS Letters (1994) vol. 351, No. 2, pp. 168-180.

Vrzheschch, P. V. et al., "Supercooperativity in platelet aggregation: Substituted pyridyl isoxazoles, a new class of supercooperative platelet aggregation inhibitors," FEBS Letters (1994) vol. 351, No. 2, pp. 168-170.

Hata, "New Approaches to Antifungal Drugs for the Treatment of Fungal and Protozoal Infections, Ravuconazole and Beyond: New Targets and Pre-clinical Strategies," The SMI's 12th Annual Conference, Superbugs and Superdrugs, Mar. 18, 2010, Crowne Plaza London—St. James, 44 pages.

Lo et al., "Development of highly selective and sensitive probes for hydrogen peroxide." Communication, Chem Comm, The Royal Society of Chemistry, 2003, pp. 2728-2729.

Chandran et al., "Synthesis of 8-Aminoquinolines: Part II—8-Guanidine Derivatives," Journal of Scientific & Industrial Research (1952) 11B, 129-132

International Search Report issued Feb. 3, 2009, in PCT International Application No. PCT/JP2008/073697.

Office Action issued May 4, 2010, in copending U.S. Appl. No. 11/658,901.

European Search Report issued Jul. 19, 2010, in corresponding European Patent Application No. 06730370.1.

Pernak, J. et al., "Synthesis and antimicrobial activities of new pyridinium and benzimidazolium chlorides," Eur. J. Med. Chem., vol. 36 (2001) pp. 313-320.

Pregnolato, M. et al., "3H-[1,2]Dithiolo[3,4-b]pyridine-3-thione and its derivatives Synthesis and antimicrobial activity," IL FARMACO, vol. 55, (2000) pp. 669-679.

Chan et al., "Discovery of 1,6-Naphthylridines as a Novel Class of Potent and Selective Human Cytomegalovirus Inhibitors," Journal of Medicinal Chemistry (1999), vol. 42, No. 16, pp. 3023-3025.

Kushner et al., "Experimental Chemotherapy of Tuberculosis. II. The Synthesis of Pyrazinamides and Related Compounds," Journal of the American Chemical Society (1952), vol. 74, pp. 3617-3621.

Lucas et al., "Facile Synthesis of a Library of 9-Alkyl-8-benzyl-9H-purin-6-ylamine Derivatives," Journal of Combinatorial Chemistry (2001), vol. 3, No. 6, pp. 518-520.

Tanaka et al., "An Effective Synthesis of a (Pyridin-3-yl)isoxazole via 1,3-Dipolar Cycloaddition Using ZnCl2: Synthesis of a (2-Aminopyridin-3-yl)isoxazole Derivative and its Antifungal Activity," Chemistry Letters, vol. 39, No. 10, pp. 1033-1035, The Chemical Society of Japan, Oct. 5, 2010.

English translation of International Search Report mailed Aug. 31, 2010, issued in corresponding PCT International Application No. PCT/JP2010/060502.

Extended European Search Report dated Jan. 12, 2011, issued in European Patent Application No. 08868067.3.

Office Action issued Jan. 24, 2011, in Saudi Arabian Patent Application No. 108290840, with English translation.

Office Action issued Jul. 30, 2009, in Pakistani Patent Application No. 1524/2008.

Ex parte Quayle Action issued Mar. 31, 2011, in copending U.S. Appl. No. 11/658,901.

Extended European Search Report issued Apr. 18, 2011, in European Patent Application No. 08740624.5.

Freshney et al., Culture of Animal Cells, A Manual of Basic Technique, 1983, Wiley & Sons, Inc., New York pp. 7-8.

International Search Report issued Aug. 31, 2010, in PCT International Patent Application No. PCT/JP2010/060502.

Freshney et al., Culture of Animal Cells, A Manual of Basic Technique, 1983, Wiley & Sons, Inc., New York pp. 7-9.

Office Action issued Jun. 17, 2011, in related U.S. Appl. No. 12/109,834.

Hata et al., "Efficacy of Oral E1210, a New Broad-Spectrum Antifungal with a Novel Mechanism of Action, in Murine Models of Candidaisis . . . ," Antimicrobial Agents and Chemotherapy (Oct. 2011) vol. 55, No. 10, pp. 4543-4551.

Hata et al., "Efficacy of Oral E1210, a New Broad-Spectrum Antifungal, in Murine Models of Oropharylgeal Candidiasis . . . ," 50th Interscience Conference on Antimicrobial Agents and Chemotherapy (ICAAC), Boston, USA, Sep. 12-15, 2010 (Document No. F1-842).

Hata et al., "In Vitro and In Vivo Antifungal Activities of E1211, a Water-Soluble Prodrug of E1210," 50th Interscience Conference on Antimicrobial Agents and Chemotherapy (ICAAC), Boston, USA, Sep. 12-15, 2010 (Document No. F1-1377).

Horii et al., "In vivo Pharmacodynamic Correlates of Success for E1210 Treatment of Disseminated Candidiasis," 50th Interscience Conference on Antimicrobial Agents and Chemotherapy (ICAAC), Boston, USA, Sep. 12-15, 2010 (Document No. F1-843).

Miyazaki et al., "In Vitro Activity of E1210, a Novel Antifungal, against Clinically Important Yeasts and Molds," Antimicrobial Agents and Chemotherapy (Oct. 2011), vol. 55, No. 10, pp. 4652-4658.

Miyazaki et al., "In vitro Antifungal Activity of E1210, a Novel Antifungal, with Activity Against Clinically Important Yeasts and Moulds," 50th Interscience Conference on Antimicrobial Agents and Chemotherapy (ICAAC), Boston, USA, Sep. 12-15, 2010 (Document No. F1-840).

Nakamoto et al., "Synthesis and Evaluation of New Nicotinamide Derivative Antifungals Acting via Glycosylphosphatidylinositol (GPI) . . . ," 8th AFMC International Medicinal Chemistry Symposium Nov. 29-Dec. 2, 2011, Tokyo (Document No. 1P-193).

Okubo et al., "Physicochemical properties and Nonclinical Pharmacokinetics of E1211, a Water-Soluble Prodrug of E1210," 50th Interscience Conference on Antimicrobial Agents and Chemotherapy (ICAAC), Boston, USA, Sep. 12-15, 2010 (Document No. F1-1376).

Okubo et al., "Preclinical Pharmacokinetics and Toxicology of E1210, a New Broad-Spectrum Antifungal," 50th Interscience Conference on Antimicrobial Agents and Chemotherapy (ICAAC), Boston, USA, Sep. 12-15, 2010 (Document No. F1-844).

Pfaller et al., "In Vitro Activity of a Novel Broad-spectrum Antifungal Agent, E1210, and Comparators Tested against Candida spp.," 50th Interscience Conference on Antimicrobial Agents and Chemotherapy (ICAAC), Boston, USA, Sep. 12-15, 2010 (Document No. F1-1373).

Pfaller et al., "In Vitro Activity of a Novel Broad-spectrum Antifungal, E1210, Tested against Aspergillus spp. By CLSI . . . ," 50th Interscience Conference on Antimicrobial Agents and Chemotherapy (ICAAC), Boston, USA, Sep. 12-15, 2010 (Document No. F1-1375).

Pfaller et al., "In Vitro Activity of a Novel Broad-Spectrum Antifungal, E1210, Tested against Aspergillus spp. Determined by CLSI . . . ," Antimicrobial Agents and Chemotherapy (Nov. 2011) vol. 55, No. 11, pp. 5155-5158.

Pfaller et al., "In vitro activity of a novel broad-spectrum antifungal, E1210, tested against Candida spp. as determined by CLSI broth microdilution method," Diagnostic Microbiology and Infectious Disease (2011) vol. 71, pp. 167-170.

Pfaller et al., "Pre-clinical development of antifungal susceptibility test methods for the testing fo the novel antifungal agent E1210 versus Candida: comparison . . . ," J. Antimicrob. Chemother. (2011) vol. 66, pp. 2581-2584.

Pfaller et al., "Pre-clinical Development of Susceptibility Testing Methods for the Novel Antifungal E1210 Tested Against Candida: Comparison of . . . ," 50th Interscience Conference on Antimicrobial Agents and Chemotherapy (ICAAC), Boston, USA, Sep. 12-15, 2010 (Document No. F1-1374).

Watanabe et al., "E1210, a New Broad-Spectrum Antifungal, Inhibits Glycosylphosphatidylinositol Biosynthesis in Fungi and Affects . . . ," 50th Interscience Conference on Antimicrobial Agents and Chemotherapy (ICAAC), Boston, USA, Sep. 12-15, 2010 (Document No. F1-841).

Watanabe et al., "In Vitro Activity of E 1 210 and in Vivo Activity of E1211, a Water-Soluble Prodrug of E1210, in Combination with Other Antifungals," 50th Interscience Conference on Antimicrobial Agents and Chemotherapy (ICAAC), Boston, USA, Sep. 12-15, 2010 (Document No. F1-1378).

Hata et al., "Efficacy of Oral E1210, a New Broad-Spectrum Antifungal, in Murine Models of Oropharylgeal Candidiasis . . . ," 50th Interscience Conference on Antimicrobial Agents and Chemotherapy (ICAAC), Boston, USA, Sep. 12-15, 2010 (Document No. F1-842).

Hata et al., "In Vitro and In Vivo Antifungal Activities of E1211, a Water-Soluble Prodrug of E1220," 51st Interscience Conference on Antimicrobial Agents and Chemotherapy (ICAAC), Chicago, USA, Sep. 17-22, 2011 (Document No. F1-1377).

Horii et al., "In vivo Pharmacodynamic Correlates of Success for E1210 Treatment of Disseminated.Candidiasis," 50th Interscience Conference on Antimicrobial Agents and Chemotherapy (ICAAC), Boston, USA, Sep. 12-15, 2010 (Document No. F1-843).

Miyazaki "In vitro Antifungal Activity of E1210, a Novel Antifungal, with Activity Against Clinically.Important Yeasts and Moulds," 50th Interscience Conference on Antimicrobial Agents and Chemotherapy (ICAAC), Boston, USA, Sep. 12-15, 2010 (Document No. F1-840).

Okubo et al., "Physicochemical properties and Nonclinical Pharmacokinetics of E1211, a Water-Soluble Prodrug of E1210," 51st Interscience Conference on Antimicrobial Agents and Chemotherapy (ICAAC), Chicago, USA, Sep. 17-22, 2011 (Document No. F1-1376).

Pfaller et al., "In Vitro Activity of a Novel Broad-spectrum Antifungal Agent, E1210, and Comparators Tested against Candida spp.," 51st Interscience Conference on Antimicrobial Agents and Chemotherapy (ICAAC), Chicago, USA, Sep. 17-22, 2011 (Document No. F1-1373).

Pfaller et al., "In Vitro of a Novel Broad-spectrum Antifungal, E1210, Tested against Aspergillus spp. by CLSI . . . ," 51st Interscience Conference on Antimicrobial Agents and Chemotherapy (ICAAC), Chicago, USA, Sep. 17-22, 2011 (Document No. F1-1375).

Pfaller et al., "Pre-clinical Development of Susceptibility Testing Methods for the Novel Antifungal E1210 Tested Against Candida: Comparison of . . . ," 51st Interscience Conference on Antimicrobial Agents and Chemotherapy (ICAAC), Chicago, USA, Sep. 17-22, 2011 (Document No. F1-1374).

Watanabe et al., "In Vitro Activity of E1210 and In Vivo Activity of E1211, a Water-Soluble Prodrug of E1210, in Combination with Other Antifungals," 51st Interscience Conference on Antimicrobial Agents and Chemotherapy (ICAAC), Chicago, USA, Sep. 17-22, 2011 (Document No. F1-1378).

Office Action issued Oct. 20, 2011, Indian Patent Application No. 3678/DELPN/2008.

Extended European Search Report issued Apr. 3, 2012, in European Patent Applicaten No. 05740790.4.

Office Action issued Apr. 13, 2012, in U.S. Appl. No. 12/109,634.

Official Acton issued Mar. 22, 2012, in Russian Patent Application No. 200143926/04, with English translation.

Response filed Mar. 30, 2012, in reply to Office Action issued in Chinese Patent Application No. 200680040781.0, with Engish translation.

Extended European Search Report issued Apr. 27, 2012, in European Patent Application No. 09821820.9.

Notice of Allowance issued May 11, 2012, in Ukraine Patent Application No. a201008001, with English translation.

Notice of Second Office Action dated May 3, 2012, issued in Chinese Patent Application No. 200880013858.4, with Enlish translation.

Response filed Apr. 26, 2012, in reply to the Office Action dated Nov. 3, 2011, issued in Australian Patent Application No. 2008246798.

Amendment filed Jul. 3, 2012, in response to the Office Action issued Apr. 13. 2012, in U.S. Appl. No. 12/109,834.

Notice of Acceptance issued Jul. 2, 2012, in Australian Patent Application No. 2008246754.

Notification of Second Office Action dated May 3, 2012, issued in Chinese Patent Application No. 20880013856.4, with English translation.

Response filed Apr. 26, 2006, in reply to the Office Action dated Nov. 3, 2011, issued in Australian Patent Application No. 2008246798.

Request for Reexamination filed Jan. 20, 2012, in Chinese Patent Application No. 200880007023.8, with English translation.

Amendment in Response to Final Office Action filed Feb. 16, 2012, in reply to the Office Action issued Dec. 14, 2011, in U.S. Appl. No. 12/442,293.

Response dated Mar. 6, 2012, filed in reply to the Office Action issued Oct. 26, 2011, in Chinese Patent Application No. 200880013858.4, with English translation.

Heimbach et al., "Overcoming Poor Aqueous Solubility of Drugs for Oral Delivery", Prodrugs: Challenges and Rewards, Part 1 (edited by Stella et al.), Chapter 2.2.1, pp. 158-215 (59 pages), Springer, 2007.

Response to Chinese Office Action, dated Sep. 23, 2011, for Chinese Application No. 200880007023.8.

Response to Chinese Office Action, dated Sep. 8, 2011, for Chinese Application No. 200680040781.0.

Response to Extended European Search Report, dated Apr. 8, 2011, for European Application No. 07828273.8.

Response to Extended European Search Report, dated Jun. 8, 2011, for European Application No. 08740624.5.

Response to Thai Office Action for Thai Application No. 0901004757.

Response to US Office Action, dated Jun. 7, 2011, for U.S. Appl. No. 12/704,643

Vietnamese Office Action, dated Apr. 16, 2010, for Vietnamese Application No. 1-2008-01321.

Communication Pursuant to Article 94(3) EPC issued May 10, 2012, in European Patent Application No. 08868067.3.

Response filed May 4, 2012, in reply to the Office Action issued Jan. 4, 2012, in Pakistan Patent Application No. 1524/2008, with English translation.

Amendment Order for Patent Application issued Apr. 25, 2012, in Thailand Patent Application No. 0901004757, with English translation.

Examination Report dated Jan. 4, 2012, issued in Pakistani Patent Application No. 1524/2008.

Communication Under Rule 71(3) EPC issued May 14, 2012, in European Patent Application No. 06612167.0.

Examiner's First Report issued May 18, 2012, in Australian Patent Application No. 2008246754.

Examiner's Report No. 2 Issued May 30, 2012, in Australian Patent Application No. 2005246798.

Notice of Acceptance of Application issued May 30, 2012, in Pakistan Patent Application No. 1524/2008.

Notice of Acceptance of Application issued May 30, 2012, in Pakistan Patent Application No. 680/2011.

Notice of Reasons for Rejection issued Jun. 1. 2012, in Japanese patent Application No. 2007-542735, with English translation.

Notification to Complete Registration Formalities dated Jun. 6, 2012, issued in Chinese Patent Application No. 200680040781.0, with English translation.

Office Action issued May 15, 2012, in Taiwan Patent Application No. 095139861, With English translation.

Response filed Apr. 26, 2012, in reply to the First Examination Report issued Oct. 20, 2011, in Indian Patent Application No. 3678/DELNP/2008.

Response filed Jane 20, 2012, in reply to Examiner's First Report issued May 18, 2012, in Australian Patent Application No, 2008246754.

Response filed May 24, 2012, in Russian Patent Application No. 2009143926, with English translation.
Amendment filed Jul. 3, 2012, in response to the Office Action issued Apr. 13, 2012, in U.S. Appl. No. 12/109,834.
Second Office Action issued Jan. 12, 2012, in Chinese Patent Application No. 200680040781.0, with English translation.
Extended European Search Report issued Apr. 3, 2012, in European Application No. 08740790.4.
Office Action issued Apr. 13, 2012, in U.S. Appl. No. 12/109,834.
Official Action issued Mar. 22, 2012, in Russian Patent Application No. 200914326/04, with English translation.
Response filed Mar. 20, 2012, in reply to Office Action issued in Chinese Patent Application No. 200680040781.0, with English translation.
Communication Under Rule 71(3) EPC issued May 14, 2012, in European Patent Application No. 06812187.0.
Examiner's Report No. 2 issued May 30, 2012, in Australian Patent Application No. 2008246796.
Notice of Reasons for Rejection issued Jun. 1, 2012, in Japanese patent Application No. 2007-542735, with English translation.
Response filed Jun. 20, 2012, in reply to Examiner's First Report issued May 18, 2012, in Australian Patent Application No. 2008246754.
Extended European Search Report issued Apr. 3, 2012, in European Patent Application No. 05740790.4.
Office Action issued Apr. 13, 2012, in U.S. Appl. No. 12/109,534.
Official Action issued Mar. 22, 2012, in Russian Patent Application No. 2009143926/04, with English translation.
Response filed Mar. 30, 2012, in reply to Office Action issued in Chinese Patent Application No. 200680040781.0, with English translation.
Extended European Search Report issued Apr. 27, 2012, in European Patent Application No. 09621820.9.
Request for Reexamination filed Jan. 20, 2012, in Chinese Patent Application No. 20088007023.8, with English translation.
Australian Office Action dated Oct. 22, 2009, for Australian Application No. 2006309762.
Canadian Office Action, doted Apr. 13. 2010, for Canadian Application No. 2,626,767.
Chinese Office Action, dated Apr. 25. 2011, for Chinese Application No. 200680040781.0.
Chinese Office Action, dated Oct. 26, 2011, for Chinese Application No. 20008000023.8
Extended European Search Report, dated Jul. 29, 2010, for European Application No. 05750893.9.
Extended European Search Report, dated Oct. 1, 2010, for European Appicaton No. 06812187.0.
Filipino Office Action, dated Jun. 17, 2011, for Filipino Application No. 1-2006-500878.
Filipino Office Action, dated Mar. 2, 2011, for Fiiipino Application No. 1-2000-000870.
Indian Examination Report, dated Aug. 23. 2010, for Indian Application No. 839/DELNO/2007.
International Preliminary Report on Patentability and Written Opinion of the International Searching Authority, dated Jun. 29, 2010, for Application No, PCT/JP2008/073697.
International Pretiminary Report on Patentability and Written Opinion of the International Searching Authority, dated Mar. 24, 2009, for Application No. PCT/JP2007/068230.
International Preliminary Report on Patentability and Written Opinion of the International Searching Authority, dated Oct. 27, 2009, for Application No. PCT/JP2006/057851.
International Preliminary Report on Patentability and Written Opinion of the International Searching Authority, dated Oct. 3, 2007, for Application No. PCT/JP2006/308422.
International. Search Report and Written Opinion of the International Searching Authority, dated Dec. 19, 2006, for Application No. PCT/JP2006/321678.
International Search Report, dated Jun. 3, 2006, for Application No. PCT/JP2008/057569.
International Search Report, dated Sep. 20, 2005, for Application No, PCT/JP2005/014505.
Japanese Office Action, dated Jan. 5, 2011, for Japanese Application No. 2006-514417.
Japanese Office Action, dated Mar. 25, 2011 for Japanese Application No. 2005-514417.
Japanese Office Action, dated Oct 5, 2011, for Japanese Application No. 2007-512776.
Korean Notice of Allowance, dated Nov. 29, 2010, for Korean Application No. 10-2006-7010403.
Korean Office Action, dated Jul. 26, 2010, for Korean Application 10-2008-7010403.
Malaysian Office Action, dated May 31, 2011, for Malaysian Application No. PI 2005136.
Office Action, dated Apr. 16, 2010, for Mexican Application No. MX/a/2006/004671.
Mexican Office Action, dated Dec. 9, 2009, for Mexican Application No. MX/a/2006/004671.
Mexican Office Action, dated Jul. 12, 2011, for Mexican Application N. MX/a/2009/011532.
New Zealand land Examination Report, dated Feb. 9, 2010, for New Zealand Application No. 567191.
New Zealand Examination Report, dated Mar. 31. 2011, for New Zealand Application No. 578930.
New Zealand Examination Report, dated Sep. 22, 2011, for New Zealand Application No. 592418.
Pakistani Examination Report, dated Aug. 31, 2010, for Pakistanl Application No. 879/2009.
Pakistani Examination Report, dated Mar. 17, 2011, for Pakistani Application No. 548/2010.
Pakistani Office Action, dated Feb. 3, 2009, for Pakistan Application No. 385/2008.
Pakistani Office Action, dated Oct. 11. 2011, for Pakistani Application No. 680/2011.
Response to Australian Office Action, dated Jan. 29, 2010, tor Australian Application No. 2003300762.
Response to Canadian Office Action. dated Oct. 13, 2010, for Canadian Application No. 2,626,767.
Response to Chinese Office Action, dated Sep. 8, 2011 for Chinese Application No. 200680040781.0.
Response to Extended European Search Report, dated Apr. 8, 2011, for European Application No. 07826273.8.
Response to Extended European Search Report, dated Dec. 14, 2010, for European Application No. 05768693.9.
Response to Extended European Search Report, dated Mar. 1, 2011, tor European Application No. 06812187.0.
Response to Filipino Office Action, dated Jul. 7, 2011, for Filipino Application No. 1-2008-500678.
Response to Japanese Office Action, dated Jun. 1, 2011, for Japanese Application No. 2005-514417.
Response to Japanese Office Action, dated Oct. 18, 2011, for Japanese Application No. 2007-512775.
Response to New Zealand Examination Report, dated Apr. 29, 2010, for New Zealand Application No. 667151.
Response to Pakistani Office Action, dated Sep. 21, 2011, for Pakistani Application No. 1524/2006.
Response filed Mar. 21, 2011, in reply to the Thai Office Action dated Dec. 9, 2010, in Thai Patent Application No. 0901004757.
Response to Thai Office Action, dated Jul. 16, 2009, for Thai Application No. 0601006362.
Response to Thai Office Action, dated May 26, 2011, for Thai Appiication No. 0801002096.
Response to US Office Action, dated Apr. 24, 2009 for U.S. Appl. No. 10/578,890.
Response to US Office Action, dated Dec. 17, 2010, for U.S. Appl. No. 11/558,901.
Response to Vietnamese Office Action, dated Jan.8, 2010, for Vietnamese Application No. 1-2009-02302
Response to Vietnamese Office Action, dated Jul. 11, 2008, for Vietnamese Application No. 1-2006-01321.
Response to Vietnamese Office Action, dated Jun. 15, 2010, for Vietnamese Application No. 1-2006-01321.
Saudi Aaban Office Action, dated Jan. 5, 2010, for Saudi Arabian Application No. 6270396.
US Office Action, dated Apr. 1, 2011, for U.S. Appl. No. 12/704,537.

US Office Action, dated Aug. 6, 2011, for U.S. Appl. No. 12/442,293.
US Office Action, dated Jan. 19, 2010, for U.S. Appl. No. 10/575,690.
US Office Action, dated Jan. 18, 2010, for U.S. Appl. No. 11/658,901.
US Office Action, dated Jan. 19, 2011, for U.S. Appl. No. 12/704,537.
US Office Action, dated Jan. 19, 2011, for U.S. Appl. No. 12/704,543.
US Office Action, dated Mar. 27, 2009, for U.S. Appl. No. 10/575,690.
US Office Action, dated May 20, 2011, for U.S. Appl. No. 12/442,253.
US Office Action dated Nov. 5, 2010, for U.S. Appl. No. 12/109,959.
US Office Action, dated Oct. 9, 2009, for U.S. Appl. No. 11/867,249.
Vietnamese Office Action, dated Apr. 16, 2010, for Vietnamese Application No. 1-2008,-01321
Vietnamese Office Action, dated Jun. 19, 2008, for Vietnamese Application No. 1-2006-01321.
Vietnamese Office Action, dated May 20, 2011, for Vietnamese Appliciation No. 1-2011-01625.
Argument and Amendment filed on Nov. 19, 2012, in reply to the Notice of Reasons for Rejection mailed on Sep. 20, 2012, for Japanese Application No. 2009-548083 with English translation.
Chinese Office Action dated Nov. 23, 2012 issued in the Chinese Patent Application No. 200880123034.2 with English translation.
Communication under Rule 71(3) EPC dated Dec. 5, 2012 issued in European Patent Application No. 08740624.5.
Notice of Reasons for Rejection mailed on Nov. 20, 2012 issued in the Japanese Patent Application No. 2009-512922 with English translation.
Office Action dated Dec. 3, 2012 for U.S. Appl. No. 13/476,727.
Response filed on Nov. 21, 2012, in reply to the Office Action dated Apr. 25, 2012 for Thai patent application No. 0901004757 with English translation.
Response filed Aug. 14, 2012, in Reply to the Office Action issued in Taiwan Patent Application No. 095139861, with English translation.
Response filed Jul. 17, 2012, in reply to the Office Action isssued in Chinese Patent Application No. 200880013858.4, with English translation.
Response filed Jul. 31, 2012, in reply to the Notice of Reasons for Rejection issued May 30, 2012, in Japanese Patent Application No. 2007-524735, with English translation.
Chen et al., "Studies on Acylthiesemicarbazides and Related Heterocyclic Derivatives (XVIII)—Syntheses and Antibacterial Activity of 2-Arylamino-5-[5-(3-Pyridyl)-2H-tetrazol-2-ylmethylene)-1,3,4-Thiadiazoles," Chemical Journal of Chinese Universities (1991), vol. 12, No. 8, pp. 1069-1071. with English abstract.
Communication Under Rule 71(3) EPC issued Sep. 24, 2012, in European Patent Application No. 06730370.1.
Decision to Grant a Patent issued Sep. 26. 2012, in Japanese Patent Application No. 2007-542735, with English translation.
Full English translation of Response filed Aug. 14, 2012, in reply to the First Office .Action issued May 15, 2012, in Taiwan Patent Application No. 095139861.
Notice of Reasons for Rejection issued Sep. 20, 2012, in Japanese Patent Application No, 2009-548083, with English translation.
Notice of Reasons for Rejection issued Sep. 25, 2012, in Japanese Patent Application No. 2008-535377, with English translation.
Registry [Online] Retrieved from STN Database, Cas Registry No. 431922-54-2, Jun. 18, 2002 (Date searched: Sep. 20, 2012),.
Registry [Online] Retrieved from STN Database, Cas Registry No. 434304-24-2, Jun. 27, 2002 (Date searched: Sep. 20, 2012).
Registry [Online] Retrieved from STN Database, Cas Registry No. 438574-99-3, Jul. 16, 2002 (Date searched: Sep. 20, 2012).
Registry [Online] Retrieved from STN Database, Cas Registry No. 764713-41-9, Oct. 18, 2002 (Date searched: Sep. 20, 2012).
Response filed Sep. 5, 2012, in repfy to the Official Communication pursuant to Art 94(3) EPC issued May 10, 2012, in European Patent Application 08868067.3.
Wu at al., "Studies on Acylthipsernicarbazitles and Related Heterocycle (XXIII)—Synthesis and Bacterial Activity of 5-(5-(3-pyridyL)-2H-tetrazole-2-ylmethyl)-2-arylamine-1,3,4-oxadiazoles," Chemical Research in Chinese Universities (1994), vol. 10, No. 2, pp, 181-190.

Approval Decision Letter from the Intellectual Property Office issued Nov. 16 2012, in Taiwan Patent Application No. 095139861, with English translation.
Argument and Amendment filed Oct. 30, 2012, in reply to the Notice of Reasons for Rejection issued Sep. 25, 2012, in Japanese Patent Application No. JP2008-535377, with English translation.
Examiner's Report Issued on Patent of Invention Application issued Sep. 11, 2012, in Chilean Patent Application No. 908-2011, with English translation.
Official Action issued Oct. 15, 2012, in Russian Patent Application No. 2010126105/04, with English translation.
Response filed Nov. 6, 2012, in reply to the Communication Persuant to Rule 70(2) and 70a(2) issued May 15, 2012, in European Patent Application No. 09821820.9.
Australian Office Action, dated Nov. 3, 2011, for Australian Application No. 2008246798.
Australian Office Action, dated Oct. 22, 2009, for Australian Application No. 2006309762.
Canadian Office Action, dated Apr. 13, 2010, for Canadian Application No. 2,626,767.
Chinese Office Action, dated Apr. 25, 2011, for Chinese Application No. 200680040781.0.
Chinese Office Action, dated Jun. 22, 2011, for Chinese Application No. 200880007023.8.
Chinese Office Action, dated Oct. 26, 2011, for Chinese Application No. 200880007023.8.
Chinese Office Action, dated Oct. 26, 2011, for Chinese Application No. 200880013858.4.
Extended European Search Report, dated Apr. 18, 2011, for European Application No. 08740624.5.
Extended European Search Report, dated Jul. 29, 2010, for European Application No. 05768893.9.
Extended European Search Report, dated Oct. 1, 2010, for European Application No. 06812187.0.
Filipino Office Action, dated Jun. 17, 2011, for Filipino Application No. 1-2008-500878.
Filipino Office Action, dated Mar. 2, 2011, for Filipino Application No. 1-2008-500878.
Heimbach et al., "Overcoming Poor Aqueous Solubility of Drugs for Oral Delivery", Prodrugs: Challenges and Rewards, Part 1 (edited by Stella et al.), Chapter 2.2.1, pp. 158-215 (59 pp.), Springer, 2007.
Indian Examination Report, dated Aug. 23, 2010, for Indian Application No. 839/DELNP/2007.
Indian Examination Report, dated Jan. 12, 2011, for Indian Application No. 7442/DELNP/2007.
Indian Examination Report, dated Jul. 14, 2011, for Indian Application No. 839/DELNP/2007.
Indian Examination Report, dated Oct. 20, 2011, for Indian Application No. 3678/DELNP/2008.
International Preliminary Report on Patentability and Written Opinion of the International Searching Authority, dated Apr. 26, 2011, for Application No. PCT/JP2009/005559.
International Preliminary Report on Patentability and Written Opinion of the International Searching Authority, dated Apr. 3, 2006, for Application No. PCT/JP2004/014063.
International Preliminary Report on Patentability and Written Opinion of the International Searching Authority, dated Feb. 13, 2007, for Application No. PCT/JP2005/014505.
International Preliminary Report on Patentability and Written Opinion of the International Searching Authority, dated Jun. 29, 2010, for Application No. PCT/JP2008/073697.
International Preliminary Report on Patentability and Written Opinion of the International Searching Authority, dated Mar. 24, 2009, for Application No. PCT/JP2007/068230.
International Preliminary Report on Patentability and Written Opinion of the International Searching Authority, dated Oct. 27, 2009, for Application No. PCT/JP2008/057851.
International Preliminary Report on Patentability and Written Opinion of the International Searching Authority, dated Oct. 3, 2007, for Application No. PCT/JP2006/306422.
International Search Report and Written Opinion of the International Searching Authority, dated Dec. 19, 2006, for Application No. PCT/JP2006/321678.

International Search Report, dated Dec. 28, 2004, for Application No. PCT/JP2004/014063.
International Search Report, dated Jun. 3, 2008, for Application No. PCT/JP2008/057569.
International Search Report, dated Jun. 6, 2006, for Application No. PCT/JP2006/306422.
International Search Report, dated Nov. 13, 2007, for Application No. PCT/JP2007/068230.
International Search Report, dated Nov. 24, 2009, for Application No. PCT/JP2009/005559.
International Search Report, dated Sep. 20, 2005, for Application No. PCT/JP2005/014505.
Japanese Office Action, dated Aug. 6, 2010, for Japanese Application No. 2005-514417.
Japanese Office Action, dated Jan. 5, 2011, for Japanese Application No. 2005-514417.
Japanese Office Action, dated Mar. 25, 2011, for Japanese Application No. 2005-514417.
Japanese Office Action, dated Oct. 5, 2011, for Japanese Application No. 2007-512776.
Korean Notice of Allowance, dated Nov. 29, 2010, for Korean Application No. 10-2008-7010403.
Korean Office Action, dated Jul. 26, 2010, for Korean Application No. 10-2008-7010403.
Malaysian Office Action, dated May 31, 2011, for Malaysian Application No. Pi 20081356.
Mexican Office Action, dated Apr. 16, 2010, for Mexican Application No. Mx/a/2008/004671.
Mexican Office Action, dated Dec. 9, 2009, for Mexican Application No. Mx/a/2008/004671.
Mexican Office Action, dated Jul. 12, 2011, for Mexican Application No. Mx/a/2009/011532.
Mexican Office Action, dated Sep. 27, 2011, for Mexican Application No. Mx/a/2010/007093.
New Zealand Examination Report, dated Feb. 9, 2010, for New Zealand Application No. 567191.
New Zealand Examination Report, dated Mar. 31, 2011, for New Zealand Application No. 578930.
New Zealand Examination Report, dated Oct. 8, 2010, for New Zealand Application No. 578930.
New Zealand Examination Report, dated Sep. 20, 2011, for New Zealand Application No. 592416.
Pakistani Examination Report, dated Aug. 31, 2010, for Pakistani Application No. 879/2009.
Pakistani Examination Report, dated Mar. 17, 2011, for Pakistani Application No. 546/2010.
Pakistani Office Action, dated Feb. 3, 2009, for Pakistani Application No. 385/2008.
Pakistani Office Action, dated Nov. 28, 2008, for Pakistani Application No. 1442/2006.
Pakistani Office Action, dated Oct. 11, 2011, for Pakistani Application No. 680/2011.
Response to Australian Office Action, dated Jan. 29, 2010, for Australian Application No. 2006309762.
Response to Canadian Office Action, dated Oct. 13, 2010, for Canadian Application No. 2,626,767.
Response to Chinese Office Action, dated Sep. 23, 2011, for Chinese Application No.200880007023.8.
Response to Chinese Office Action, dated Sep. 8, 2011, for Chinese Application No.200680040781.0.
Response to Extended European Search Report, dated Apr. 8, 2011, for European Application No.07828273.8.
Response to Extended European Search Report, dated Dec. 14, 2010, for European Application.No. 05768893.9.
Response to Extended European Search 08740624.5 Report, dated Jun. 8, 2011, for European Application No. 08740624.5.
Response to Extended European Search 06812187.0 Report, dated Mar. 1, 2011, for European Application No. 06812187.0.
Response to Extended European Search Report, dated Mar. 29, 2011, for European Application No. 08868067.3.
Response to Extended European Search Report, dated Nov. 24, 2010, for European Application No. 06730370.1.

Response to Filipino Office Action, dated Apr. 29, 2011, for Filipino Application No. 1-2008-500878.
Response to Filipino Office Action, dated Jul. 7, 2011, for Filipino Application No. 1-2008-500878.
Response to Indian Examination Report, dated Mar. 7, 2011, for Indian Application No. 839/DELNP/2007.
Response to Indian Examination Report, dated May 16, 2011, for Indian Application No. 7442/DELNP/2007.
Response to to Japanese Office Action, dated Jun. 1, 2011, for Japanese Application No. 2005-514417.
Response to Japanese Office Action, dated Mar. 1, 2011, for Japanese Application No. 2005-514417.
Response to Japanese Office Action, dated Oct. 18, 2011, for Japanese Application No. 2007-512776.
Response to Japanese Office Action, dated Sep. 29, 2010, for Japanese Application No. 2005-514417.
Response to Korean Office Action, dated Sep. 27, 2010, for Korean Application No. 10-2008-7010403.
Response to Malaysian Office Action, dated Jun. 1, 2011, for Malaysian Application No. PI 20081356.
Response to Mexican Office Action, dated Aug. 17, 2010, for Mexican Application No. Mx/a/2008/004671.
Response to Mexican Office Action, dated Dec. 7, 2011, for Mexican Application No. Mx/a/2010/007093.
Response to Mexican Office Action, dated Mar. 25, 2010, for Mexican Application No. Mx/a/2008/004671.
Response to Mexican Office Action, dated Sep. 20, 2011, for Mexican Application No. Mx/a/2009/011532.
Response to New Zealand Examination Report, dated Apr. 15, 2011, for New Zealand Application No. 578930.
Response to New Zealand Examination Report, dated Apr. 29, 2010, for New Zealand Application No. 567191.
Response to New Zealand Examination Report, dated Mar. 18, 2011, for New Zealand No. 578930.
Response to New Zealand Examination Report, dated Nov. 14, 2011, for New Zealand Application No. 592416.
Response to Pakistani Office Action, dated Dec. 1, 2011, for Pakistani Application No. 680/2011.
Response to Pakistani Office Action, dated Mar. 2, 2011, for Pakistani Application No. 1442/2006.
Response to Pakistani Office Action, dated Sep. 21, 2011, for Pakistani Application No. 1524/2008.
Response to Russian Office Action, dated Jun. 3, 2009, for Russian Application No. 2008121965/04.
Response to Saudi Arabian Office Action, dated Apr. 16, 2011, for Saudi Arabian Application No. 108290840.
Response to Saudi Arabian Office Action, dated Apr. 16, 2011, for Saudi Arabian Application No. 8290258.
Response to Saudi Arabian Office Action, dated Apr. 3, 2010, for Saudi Arabian Application No. 6270396.
Response to Thai Office Action for Thai Application No. 0901004757, 2009.
Response to Thai Office Action, dated Jul. 16, 2009, for Thai Application No. 0601005362.
Response to Thai Office Action, dated May 26, 2011, for Thai Application No. 0801002096.
Response to US Office Action, dated Apr. 24, 2009, for U.S. Appl. No. 10/573,890.
Response to US Office Action, dated Apr. 7, 2010, for U.S. Appl. No. 10/573,890.
Response to US Office Action, dated Aug. 3, 2009, for U.S. Appl. No. 11/589,128.
Response to US Office Action, dated Dec. 10, 2010, for U.S. Appl. No. 12/109,834.
Response to US Office Action, dated Dec. 16, 2011, for U.S. Appl. No. 12/109,834.
Response to US Office Action, dated Dec. 17, 2010, for U.S. Appl. No. 11/658,901.
Response to US Office Action, dated Feb. 17, 2011, for U.S. Appl. No. 12/704,637.
Response to US Office Action, dated Feb. 17, 2011, for U.S. Appl. No. 12/704,643.

Response to US Office Action, dated Feb. 18, 2010, for U.S. Appl. No. 11/658,901.
Response to US Office Action, dated Feb. 23, 2009, for U.S. Appl. No. 11/589,128.
Response to US Office Action, dated Jan. 27, 2011, for U.S. Appl. No. 12/109,959.
Response to US Office Action, dated Jul. 22, 2010, for U.S. Appl. No. 11/658,901.
Response to US Office Action, dated Jun. 15, 2011, for U.S. Appl. No. 12/442,293.
Response to US Office Action, dated Jun. 7, 2010, for U.S. Appl. No. 11/887,249.
Response to US Office Action, dated Jun. 7, 2011, for U.S. Appl. No. 12/704,637.
Response to US Office Action, dated Jun. 7, 2011, for U.S. Appl. No. 12/704,643.
Response to US Office Action, dated Mar. 29, 2010, for U.S. Appl. No. 11/887,249.
Response to US Office Action, dated Mar. 8, 2011, for U.S. Appl. No. 12/109,834.
Response to US Office Action, dated Nov. 6, 2009, for U.S. Appl. No. 11/887,249.
Response to US Office Action, dated Oct. 26, 2011, for U.S. Appl. No. 12/442,293.
Response to US Office Action, dated Oct. 27, 2009, for U.S. Appl. No. 10/573,890.
Response to Vietnamese Office Action, dated Jan. 8, 2010, for Vietnamese Application No. 1-2009-02302.
Response to Vietnamese Office Action, dated Jul. 11, 2008, for Vietnamese Application No. 1-2008-01321.
Response to Vietnamese Office Action, dated Jun. 13, 2011, for Vietnamese Application No. 1-2011-01026.
Response to Vietnamese Office Action, dated Jun. 15, 2010, for Vietnamese Application No. 1-2008-01321.
Russian Office Action, dated Apr. 2, 2009, for Russian Application No. 2008121965/04.
Saudi Arabian Office Action, dated Jan. 5, 2010, for Saudi Arabian Application No. 6270396.
Saudi Arabian Office Action, dated Oct. 12, 2010, for Saudi Arabian Application No. 8290258.
Supplementary Partial European Search Report, dated Feb. 6, 2009, for European Application No. 04788159.4.
Thai Office Action, dated Apr. 8, 2009, for Thai Application No. 0601005362.
Thai Office Action, dated Dec. 9, 2010, for Thai Application No. 0901004757.
Thai Office Action, dated Mar. 1, 2011, for Thai Application No. 0801002096.
US Office Action, dated Apr. 1, 2011, for U.S. Appl. No. 12/704,637.
US Office Action, dated Apr. 4, 2011, for U.S. Appl. No. 12/704,643.
US Office Action, dated Aug. 8, 2011, for U.S. Appl. No. 12/442,293.
US Office Action, dated Dec. 13, 2011, for U.S. Appl. No. 13/047,447.
US Office Action, dated Dec. 14, 2011, for U.S. Appl. No. 12/442,293.
us Office Action, dated Jan. 14, 2010, for U.S. Appl. No. 11/887,249.
us Office Action, dated Jan. 19, 2010, for U.S. Appl. No. 10/573,890.
US Office Action, dated Jan. 19, 2010, for U.S. Appl. No. 11/658,901.
US Office Action, dated Jan. 19, 2011, for U.S. Appl. No. 12/109,834.
US Office Action, dated Jan. 19, 2011, for U.S. Appl. No. 12/704,637.
US Office Action, dated Jan. 19, 2011, for U.S. Appl. No. 12/704,643.
US Office Action, dated Jan. 22, 2009, for U.S. Appl. No. 11/589,128.
US Office Action, dated Mar. 27, 2009, for U.S. Appl. No. 10/573,890.
US Office Action, dated May 14, 2010, for U.S. Appl. No. 11/887,249.
US Office Action, dated May 20, 2011, for U.S. Appl. No. 12/442,293.
US Office Action, dated May 7, 2009, for U.S. Appl. No. 11/589,128.
US Office Action, dated Nov. 10, 2010, for U.S. Appl. No. 12/109,834.
US Office Action, dated Nov. 5, 2010, for U.S. Appl. No. 12/109,959.
US Office Action, dated Oct. 9, 2009, for U.S. Appl. No. 11/887,249.

Vietnamese Office Action, dated Apr. 16, 2010, for Vietnamese Application No. 1-2008-01321
Vietnamese Office Action, dated Dec. 11, 2009, for Vietnamese Application No. 1-2009-02302.
Vietnamese Office Action, dated Jun. 19, 2008, for Vietnamese Application No. 1-2008-01321.
Vietnamese Office Action, dated May 20, 2011, for Vietnamese Application No. 1-2011-01026.
Decision on Grant of Patent for invention issued Jan. 16, 2013. In Russian Patent Application No. 2010126105/04, with English translation.
Notice otAcceptanse issued Feb. 4, 2013, in Australian Patent Appiicatlon No. 2008344341.
Database Chemcats [Online] Chemical, Abstracts Service, Columbus, Ohio, US; XP002600765 Database accession No. 2059288788 *Order No. (ON): 6700755* & Chembridge Corporation: "ChemBridge Screening Library" Jun. 9, 2010, ChemBridge Corpoation, sail Diego (USA).
Database Chemcats [Online] Chemical Abstracts Service, Colmnus, Ohio USA XP002600787 Database accession Co. 2084604173 *Order No. (ON): STK143803* & Vitas-M "Vitas-M Screening Collection" Jul. 13, 2010, Vitas-M, Hodynskl Blv. 15, Moskow, (RU).
Database Registry [Online] Chemical Abstracts Service, Columbus, Ohio, US; Jul. 16, 2002, XP002600783 Database accession No. 438574-99-3(RN) *abstract*.
Database Registry (Online) Chemical Abstracts Service Columbus, Ohio, US; Jun. 16, 2002, XP002000784 Database accession No. 431922-54-2(Rn) *abstract*.
Database Registry [Online] Chemical Abstracts Service, Cokrnbus, Ohio, US; Oct. 18, 2004, XP002600786 Database accession No. 764713-41-9(RN) *abstract*.
Extended European Search Report dated Oct. 11, 20210, issued in corresponding European Patent Application No. 07826273.8.
Office Action issued Oct. 13, 2010, in co-pending U.S. Appl. No. 11/658,901.
Decision on Grant of Patent for Invention issued Jun. 25, 2012, in Russian Patent Application No. 2009143926, with English translation.
Response filed Aug. 12, 2012, in Reply to the Office Action issued in Taiwan Patent Application No. 095139861, with English translation.
Response filed Jul. 17, 2012, in reply to the Office Action issued in Chinese Patent Application No. 200880013858.4, with English translation.
Response filed Jul. 31, 2012, in reply to the Notice of Reasons for Rejection issued May 30, 2012, in Japanese Patent Application No. 2007-542735, with English translation.
Amendment under 37 CFR 1.116 filed Mar. 21, 2013, in reply to the Office Action issued Jan. 4, 2013, in U.S. Appl. No. 12/109,834.
Decision to Grant a Patent issued Mar. 14, 2013, in Japanese Patent Applicaion No. 2009-548083, with English translation.
Election of Species Requirement issued Mar. 5, 2013, in U.S. Appl. No. 13/242,702.
Non-Final Office Action issued Apr. 4, 2013, in U.S. Appl. No. 13/242,702.
Notice of Allowance issued Apr. 8, 2013, in U.S. Appl. No. 12/109,834.
Reply to Election of Species Requirement filed Mar. 25, 2013, in response to the Election of Species Requirement issued Mar. 5, 2013, in U.S. Appl. No. 13/242,702.
Response filed Mar. 27, 2013, in reply to the First Office Action isssued in Chinese Patent Application No. 200880123034.2, with English translation.
Communication Under Rule 71(3) EPC issued Jun . 21, 2013, in European Patent Application No. 06812187.0.
Communication Pursuant to Articie 94(3) EPC issued Jan. 7, 2013, in European Patent Application No. 04788159.4.
Firia OffiCe Action issued Jan. 4, 2013, in U.S. Appl. No. 12/109,834.
Response filed Dec. 17. 2012, in reply to the Official Action issued Oct. 15, 2012, in Russian Patent Application No. 2010126105/04, With English transiation.
European Search Report issued Jul. 29, 2010, in corresponding European Patent Application No. 05768893.9.

* cited by examiner

HETEROCYCLIC RING AND PHOSPHONOXYMETHYL GROUP SUBSTITUTED PYRIDINE DERIVATIVES AND ANTIFUNGAL AGENT CONTAINING SAME

TECHNICAL FIELD

The present invention relates to novel heterocyclic ring and phosphonoxymethyl group substituted pyridine derivatives, and antifungal agents containing the same.

BACKGROUND ART

In recent years, managements of opportunistic infections have become more and more significant more than ever because of an increase in the number of elderly people and immunocompromised patients as a result of advanced chemotherapies or the like. As demonstrated by the fact that opportunistic infections are occurring one after another by different avirulent pathogen, it has been shown that the problem of infectious disease will not ends as long as there are underlying diseases that diminish the immune functions of patients. Consequently, new strategies for infectious diseases control, including the problem of drug-resistant pathogen, will be one of the important issues in the soon-to-come aged society.

In the field of antifungal agents, heretofore, for instance, amphotericine B which is based on a polyene skeleton, fluconazole, itraconazole and voriconazole which are based on an azole skeleton, or the like, have been developed for the treatment of deep seated mycoses. Most of pre-existing drugs already available commercially have similar mechanism of action, and currently, the appearance of azole-resistant fungi or the like has been problems.

In recent years, as a 1,3-β-glucan synthetase inhibitor with a novel mechanism, naturally occurring compound-derived cyclic hexapeptides caspofungin and micafungin or the like, have been developed; however, from the fact that these agents only exist in injectable form, they are not yet sufficient practically as antifungal agents.

Since there have been the situations that the pre-existing antifungal agents are insufficient for treatment of the deep seated mycoses, there is a demand and need for development of agents which are based on a novel mechanism and are of high safety. As the related art relevant to antifungal agents based on such a novel mechanism, Patent Documents 1 and 2 describe pyridine derivatives which demonstrates effects against the onset, progress, and persistence of infections by inhibiting the expression of cell wall proteins, inhibiting the cell wall assembly and also adhesion onto cells, and preventing pathogens from showing pathogenicity, with the process which transports GPI (Glycosylphosphatidylinositol)-anchored proteins to the cell wall being inhibited.

In light of this situation, there has been proposed in Patent document 3 a hetero ring-substituted pyridine derivative as an antifungal agent that has excellent antifungal action not seen in conventional antifungal agents, and is also superior in terms of its properties, safety, and metabolic stability.

On the other hand, Patent documents 4 and 5 disclose N-phosphoryloxymethyl prodrugs that are compounds represented by the following formula, as water-soluble prodrugs:

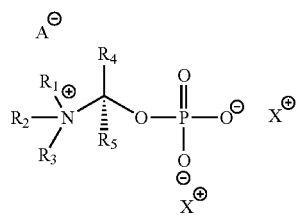

(wherein $R_1$, $R_2$, and $R_3$ represent substituents including a parent tertiary or secondary amine, each of $R_4$ and $R_5$ represents an organic or inorganic residue, and X represents a cationic organic or inorganic salt.)

However, the water-soluble prodrugs known up to now do not have an excellent antifungal action based on the inhibition of the GPI-anchored protein transport process, nor are they excellent in terms of solubility in water, stability in an aqueous solution, as well as safety and in-vivo kinetics, and the creation of a better antifungal agent has been desired.

Patent document 1: International Publication WO 02/04626 pamphlet

Patent document 2: International Publication WO 05/033079 pamphlet

Patent document 3: International Publication WO 07/052,615 pamphlet

Patent document 4: U.S. Pat. No. 6,235,728 B1

Patent document 5: Japanese Patent Publication No. 2001-527083

DISCLOSURE OF INVENTION

Problems to be Solved by the Invention

In light of such situations, it is an object of the present invention to provide an antifungal agent that has excellent antifungal action, and is also excellent in terms of solubility in water, its stability in an aqueous solution, and its safety and in-vivo kinetics.

As a result of diligent research conducted in light of the above situations, the inventors perfected the present invention upon discovering that compounds which are represented by the following formula (I):

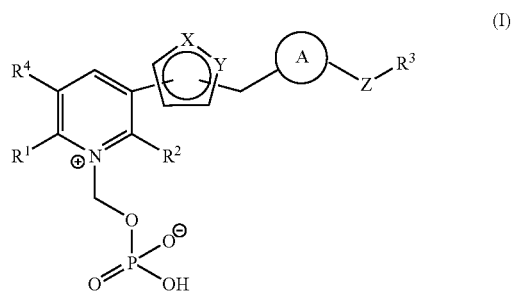

and has a phosphonoxymethyl group on a nitrogen atom on a pyridine derivative has excellent antifungal action and is also excellent in terms of solubility in water, its stability in an aqueous solution, and its safety and in-vivo kinetics.

Specifically, in a first aspect of the present invention, there is provided:

[1] A compound represented by the following formula (I):

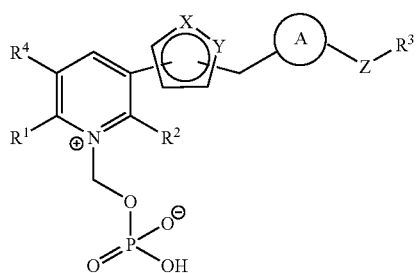

(I)

(wherein

R¹ represents a hydrogen atom, a halogen atom, an amino group, $R^{11}$—NH— (wherein $R^{11}$ represents a $C_{1-6}$ alkyl group, a hydroxy $C_{1-6}$ alkyl group, a $C_{1-6}$ alkoxy $C_{1-6}$ alkyl group, or a $C_{1-6}$ alkoxycarbonyl $C_{1-6}$ alkyl group), $R^{12}$—(CO)—NH— (wherein $R^{12}$ represents a $C_{1-6}$ alkyl group or a $C_{1-6}$ alkoxy $C_{1-6}$ alkyl group), a $C_{1-6}$ alkyl group, a hydroxy $C_{1-6}$ alkyl group, a cyano $C_{1-6}$ alkyl group, a $C_{1-6}$ alkoxy group, or a $C_{1-6}$ alkoxy $C_{1-6}$ alkyl group;

$R^2$ represents a hydrogen atom, a $C_{1-6}$ alkyl group, an amino group, or a di-$C_{1-6}$ alkylamino group;

one of X and Y represents a nitrogen atom, and the other represents a nitrogen atom or an oxygen atom;

ring A represents a 5- or 6-member heteroaryl ring or a benzene ring, which may have one or two halogen atoms or $C_{1-6}$ alkyl groups;

Z represents a single bond, a methylene group, an ethylene group, an oxygen atom, a sulfur atom, —CH₂O—, —OCH₂—, —NH—, —CH₂NH—, —NHCH₂—, —CH₂S—, or —SCH₂—;

$R^3$ represents a hydrogen atom or a halogen atom, or a $C_{1-6}$ alkyl group, a $C_{3-8}$ cycloalkyl group, a $C_{6-10}$ aryl group, a 5- or 6-member heteroaryl group, or a 5- or 6-member non-aromatic heterocyclic group, wherein these groups may have one or two substituents selected from a substituent group α; and $R^4$ represents a hydrogen atom or a halogen atom;

[substituent Group α]

a halogen atom, a cyano group, a $C_{1-6}$ alkyl group, a $C_{1-6}$ alkoxy group, a $C_{1-6}$ alkoxycarbonyl group, a $C_{3-8}$ cycloalkyl group, a $C_{2-6}$ alkenyl group, and a $C_{2-6}$ alkynyl group), or a salt thereof.

[2] The compound or the salt thereof according to item [1], wherein the salt of the compound represented by the following formula (I) is a salt represented by the following formula (IA):

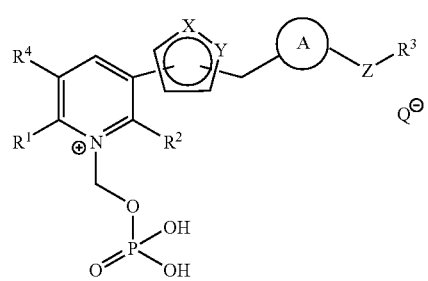

(IA)

wherein
Q⁻ represents a pharmaceutically acceptable anion.

[3] The compound or the salt thereof according to item [1], wherein the salt of the compound represented by the following formula (I) is a salt represented by the following formula (IB):

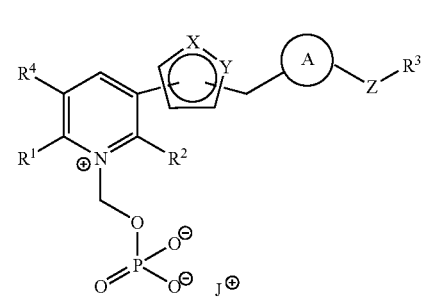

(IB)

wherein
J⁺ represents a pharmaceutically acceptable cation.

[4] The compound or the salt thereof according to any one of items [1] to [3], wherein a partial structure represented by the following formula (II):

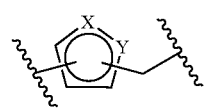

(II)

of the compound represented by the above formula (I), (IA), or (IB) represents a partial structure selected from the following group:

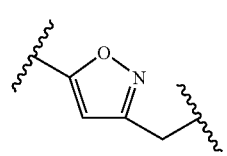

(III)

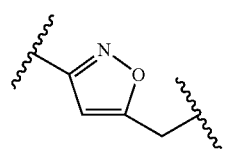

(IV)

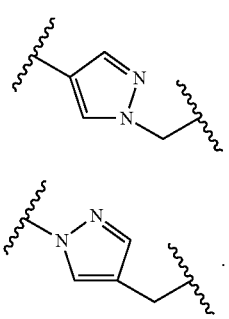

[5] The compound or the salt thereof according to any one of items [1] to [4], wherein one of X and Y represents a nitrogen atom and the other represents an oxygen atom.

[6] The compound or the salt thereof according to item [4], wherein the partial structure represented by the following formula (II):

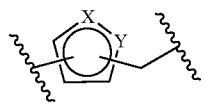

of the compound represented by the above formula (I), (IA), or (IB) represents a partial structure represented by the following formula (III):

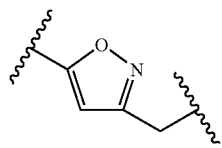

or a partial structure represented by the following formula (IV):

(IV)

[7] The compound or the salt thereof according to any one of items [1] to [6], wherein both of X and Y represent nitrogen atoms.

[8] The compound or the salt thereof according to item [7], wherein the partial structure represented by the following formula (II):

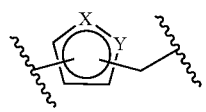

of the compound represented by the above formula (I), (IA), or (IB) represents a partial structure represented by the following formula (V):

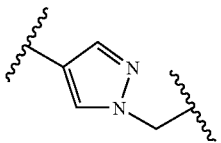

or a partial structure represented by the following formula (VI):

(VI)

[9] The compound or the salt thereof according to any one of items [1] to [8], wherein $R^2$ represents an amino group.

[10] The compound or the salt thereof according to item [9], wherein $R^1$ represents a hydrogen atom, an amino group, or a $C_{1-6}$ alkoxy $C_{1-6}$ alkyl group.

[11] The compound or the salt thereof according to any one of items [1] to [8], wherein $R^1$ represents an amino group and $R^2$ represents a hydrogen atom.

[12] The compound or the salt thereof according to any one of items [1] to [11], wherein the ring A represents a pyridine ring, a benzene ring, a furan ring, a thiophene ring, or a pyrrole ring.

[13] The compound or the salt thereof according to item [12], wherein the ring A represents a pyridine ring or a benzene ring.

[14] The compound or the salt thereof according to any one of items [1] to [13], wherein Z represents an oxygen atom, —CH$_2$O—, or —OCH$_2$—.

[15] A pharmaceutical composition comprising: the compound or the salt thereof according to any one of items [1] to [14].

[16] A medicament comprising: the compound or the salt thereof according to any one of items [1] to [14].

[17] An antifungal agent comprising as an active ingredient the compound or the salt thereof according to any one of items [1] to [14].

[18] A method for preventing and/or treating a fungal disease by administering a pharmaceutically effective amount of the compound or the salt thereof according to any one of items [1] to [14].

[19] A use of the compound or the salt thereof according to any one of items [1] to [14], for manufacture of an antifungal agent.

In addition, in a second aspect of the present invention, there is provided:

[20] A process for producing a compound represented by the following formula (I):

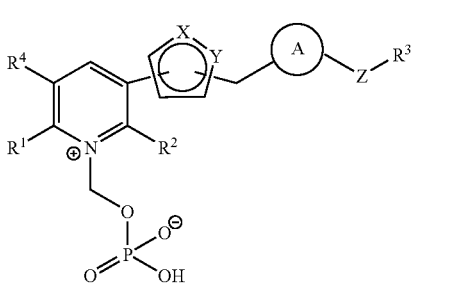

(wherein

R$^1$ represents a hydrogen atom, a halogen atom, an amino group, R$^{11}$—NH— (wherein R$^{11}$ represents a C$_{1-6}$ alkyl group, a hydroxy C$_{1-6}$ alkyl group, a C$_{1-6}$ alkoxy C$_{1-6}$ alkyl group, or a C$_{1-6}$ alkoxycarbonyl C$_{1-6}$ alkyl group), R$^{12}$—(CO)—NH— (wherein R$^{12}$ represents a C$_{1-6}$ alkyl group or a C$_{1-6}$ alkoxy C$_{1-6}$ alkyl group), a C$_{1-6}$ alkyl group, a hydroxy C$_{1-6}$ alkyl group, a cyano C$_{1-6}$ alkyl group, a C$_{1-6}$ alkoxy group, or a C$_{1-6}$ alkoxy C$_{1-6}$ alkyl group;

R$^2$ represents a hydrogen atom, a C$_{1-6}$ alkyl group, an amino group, or a di-C$_{1-6}$ alkylamino group;

one of X and Y represents a nitrogen atom, and the other represents a nitrogen atom or an oxygen atom;

ring A represents a 5- or 6-member heteroaryl ring or a benzene ring, which may have one or two halogen atoms or C$_{1-6}$ alkyl groups;

Z represents a single bond, a methylene group, an ethylene group, an oxygen atom, a sulfur atom, —CH$_2$O—, —OCH$_2$—, —NH—, —CH$_2$NH—, —NHCH$_2$—, —CH$_2$S—, or —SCH$_2$—;

R$^3$ represents a hydrogen atom or a halogen atom, or a C$_{1-6}$ alkyl group, a C$_{3-8}$ cycloalkyl group, a C$_{6-10}$ aryl group, a 5- or 6-member heteroaryl group, or a 5- or 6-member non-aromatic heterocyclic group, wherein these groups may have one or two substituents selected from a substituent group α; and R$^4$ represents a hydrogen atom or a halogen atom;

[substituent Group α]

a halogen atom, a cyano group, a C$_{1-6}$ alkyl group, a C$_{1-6}$ alkoxy group, a C$_{1-6}$ alkoxycarbonyl group, a C$_{3-8}$ cycloalkyl group, a C$_{2-6}$ alkenyl group, and a C$_{2-6}$ alkynyl group), comprising the steps of:

reacting a compound represented by the following formula (1) and phosphoric acid di-tert-butyl ester chloromethyl ester in the presence of a base; and

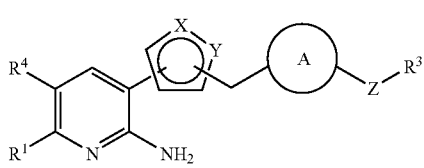

(wherein ring A, R$^1$, R$^3$, R$^4$, X, Y and Z have the same meaning as defined above)

subjecting to a treatment by an acid.

[21] The process according to item [20], wherein the base is sodium iodide.

[22] The process according to item [20] or [21], wherein the acid is trifluoroacetic acid or hydrochloric acid.

[23] A process for producing a salt of a compound represented by the following formula (IA):

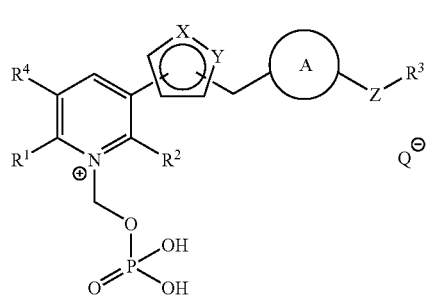

(wherein ring A, R$^1$, R$^3$, R$^4$, X, Y and Z have the same meaning as defined above, and Q$^-$ represents a pharmaceutically acceptable anion)

comprising reacting the compound obtained by the process according to any one of items [20] to [22] and an acid.

[24] The process according to item [23], wherein the acid is selected from the group consisting of hydrochloric acid, hydrobromic acid, nitric acid, and sulfuric acid.

[25] A process for producing a salt of a compound represented by the following formula (IB):

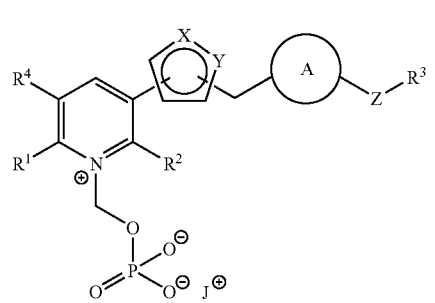

(wherein ring A, R$^1$, R$^3$, R$^4$, X, Y and Z have the same meaning as defined above, and J$^+$ represents a pharmaceutically acceptable cation)

comprising reacting the compound obtained by the process according to any one of items [20] to [22] and a base.

[26] The process according to item [25], wherein the base is selected from the group consisting of lithium hydroxide, sodium hydroxide, potassium hydroxide calcium hydroxide and lysine.

Advantageous Effects of the Invention

The compound represented by formula (I), (IA), or (IB) (hereinafter referred to simply as "the compound according to the present invention") 1) acts against the onset, development and persistence of infections by inhibiting fungal GPI biosynthesis, thereby inhibiting expression of cell wall proteins and blocking cell wall assembly while preventing the fungus from attaching to cells so that the pathogen cannot become pathogenic, and 2) is superior in terms of physical properties, and particularly its solubility in water, its stability in an aqueous solution, and its safety and in-vivo kinetics, making the above compounds extremely useful as a preventive or therapeutic agent for fungal infections.

BEST MODE FOR CARRYING OUT THE INVENTION

Figure 1:
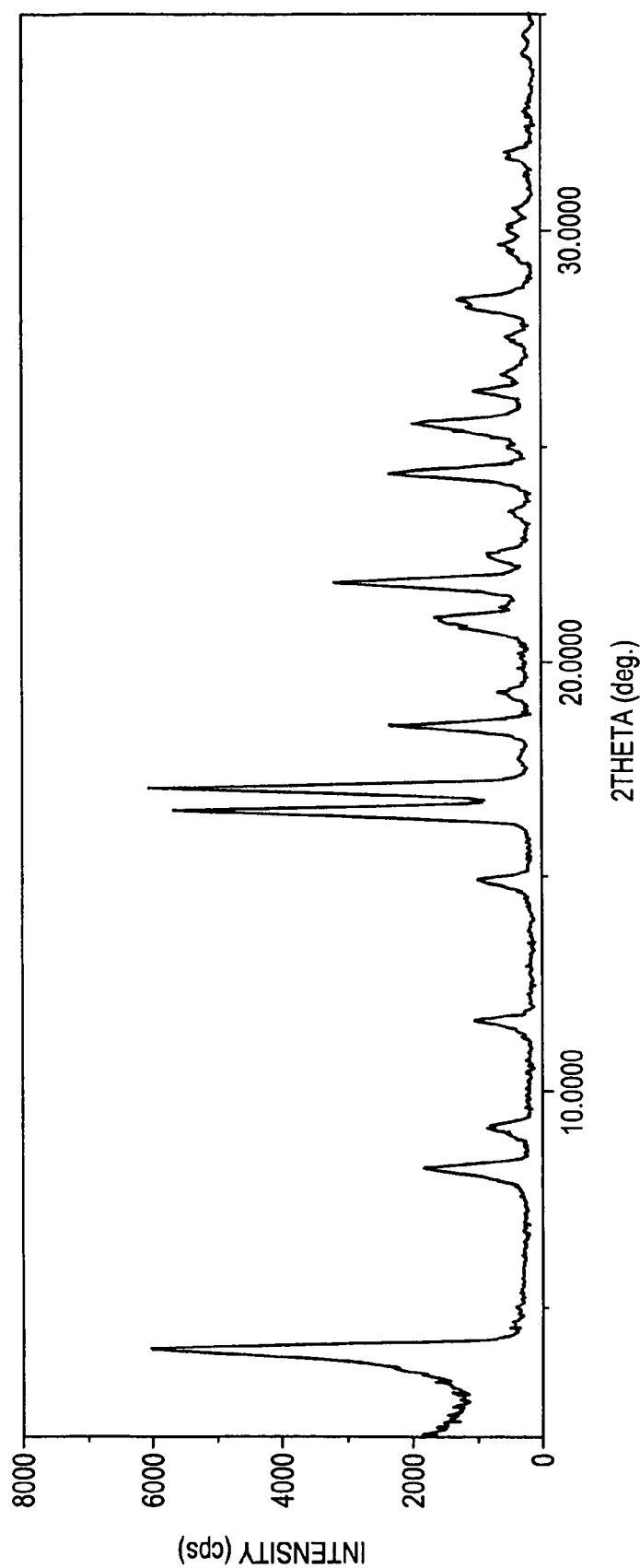
FIG. 1 shows the X-ray diffraction pattern of 2-amino-1-((phosphonoxy)methyl)-3-(3-((4-((2-pyridinyloxy)methyl)phenyl)methyl)-5-isoxazolyl)-pyridinium anhydrous form (type 1) obtained in Example 2 of the present invention.
Figure 2:
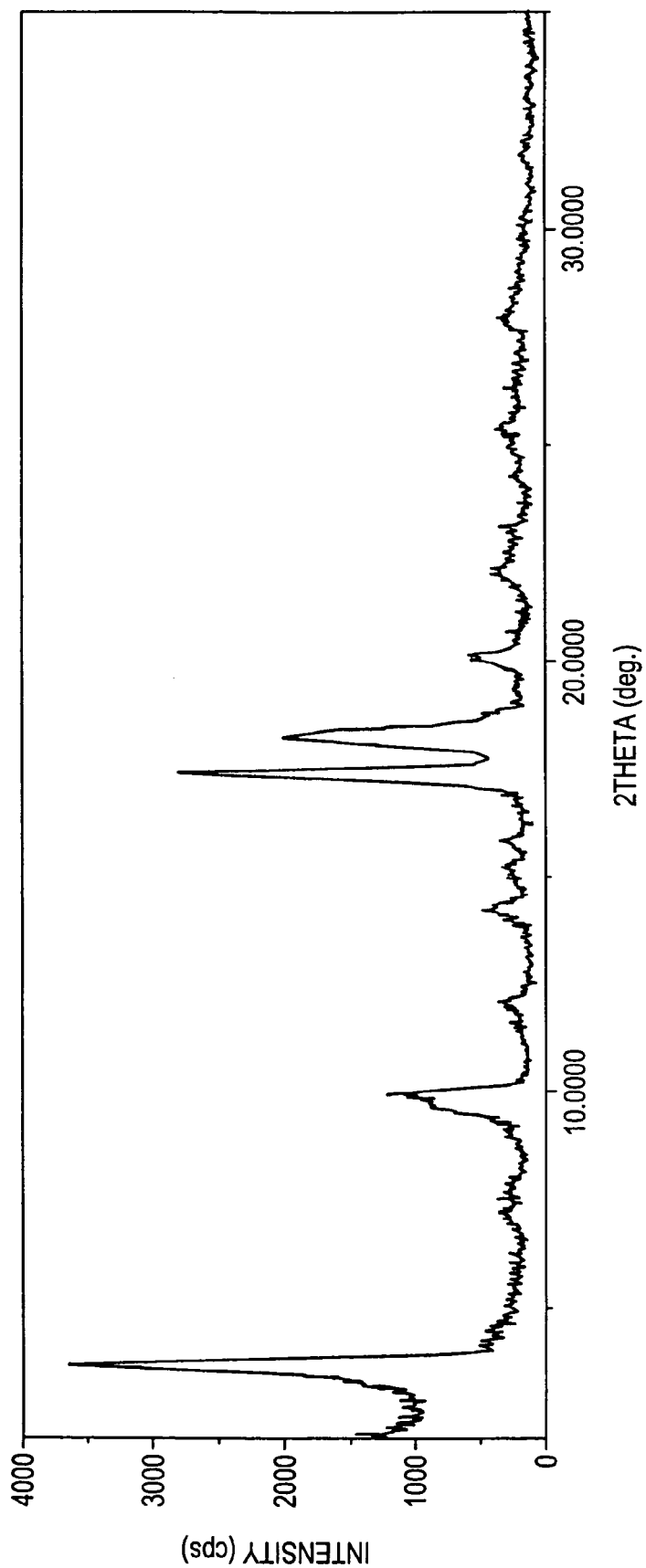
FIG. 2 shows the X-ray diffraction pattern of 2-amino-1-((phosphonoxy)methyl)-3-(3-((4-((2-pyridinyloxy)methyl)phenyl)methyl)-5-isoxazolyl)-pyridinium anhydrous form (type 2) obtained in Example 3 of the present invention.
Figure 3:
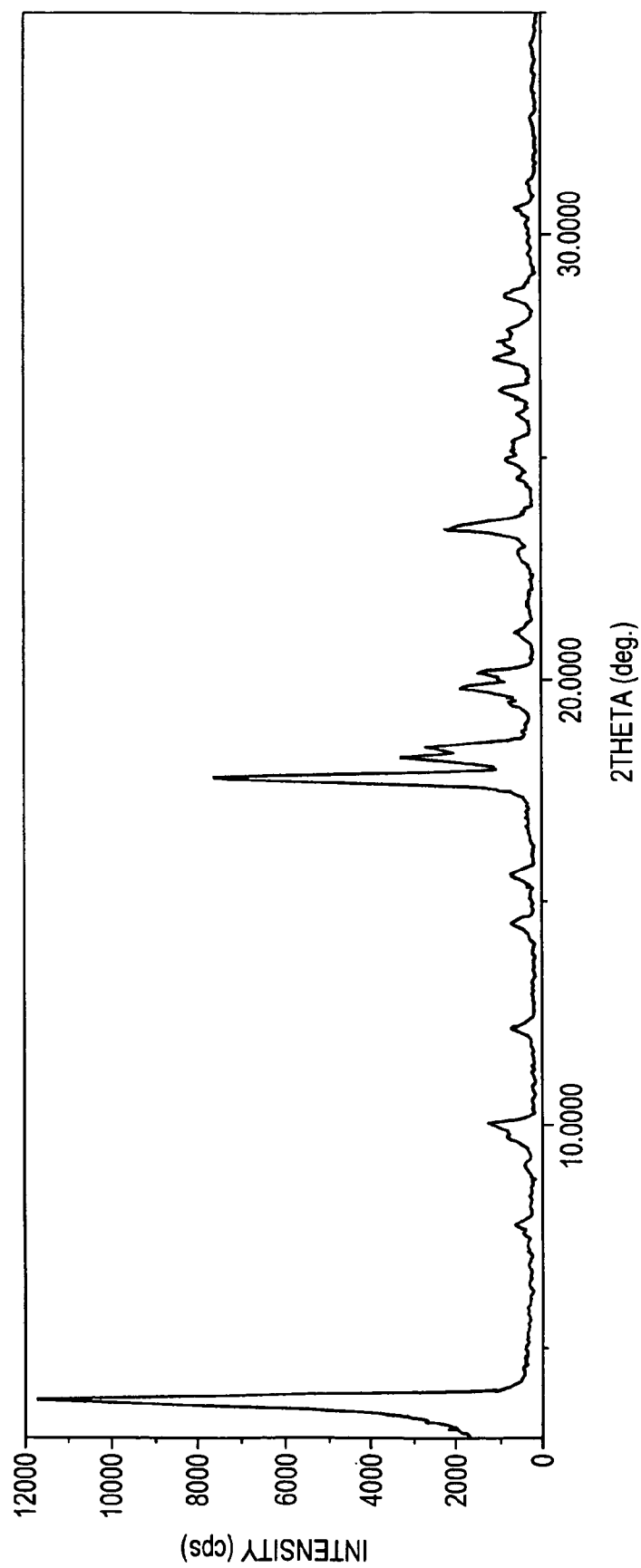
FIG. 3 shows the X-ray diffraction pattern of 2-amino-1-((phosphonoxy)methyl)-3-(3-((4-((2-pyridinyloxy)methyl)phenyl)methyl)-5-isoxazolyl)-pyridinium anhydrous form (type 3) obtained in Example 4 of the present invention.
Figure 4:
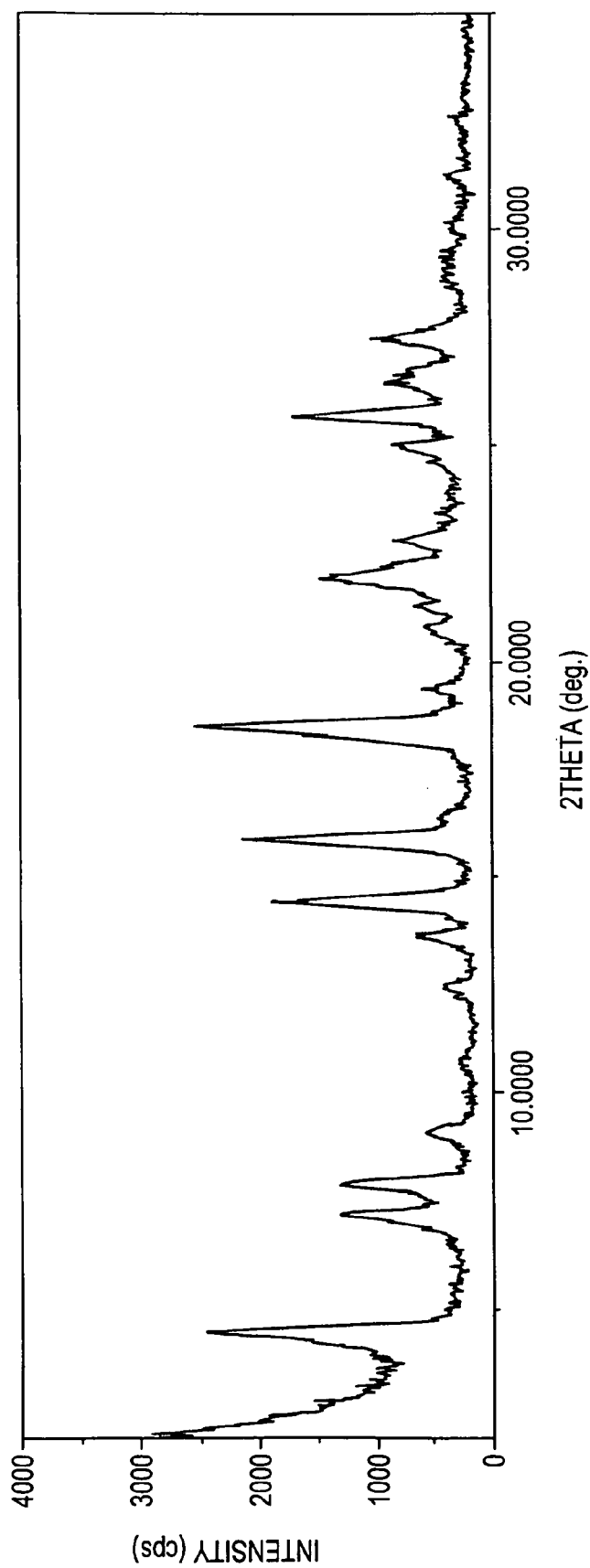
FIG. 4 shows the X-ray diffraction pattern of 2-amino-1-((phosphonoxy)methyl)-3-(3-((4-((2-pyridinyloxy)methyl)phenyl)methyl)-5-isoxazolyl)-pyridinium hydrate obtained in Example 5 of the present invention.
Figure 5:
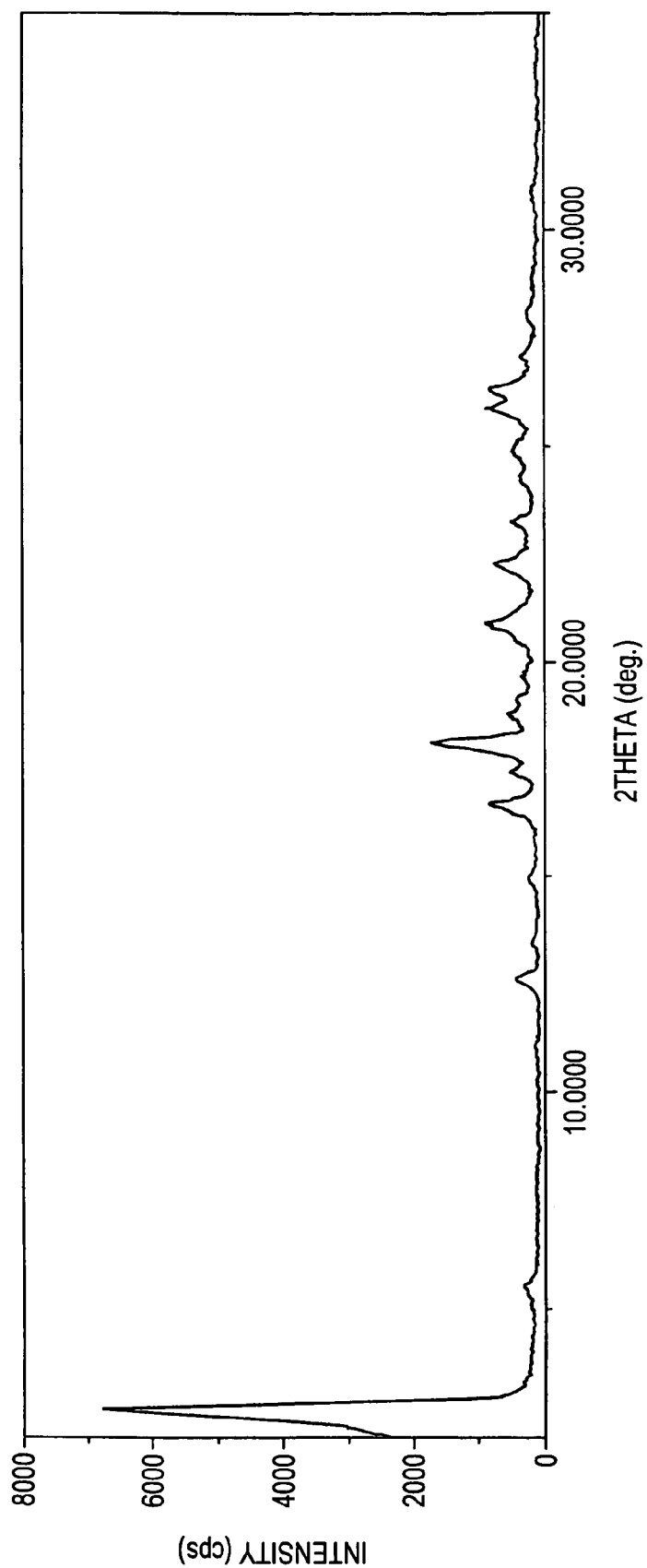
FIG. 5 shows the X-ray diffraction pattern of 2-amino-1-((phosphonoxy)methyl)-3-(3-((4-((2-pyridinyloxy)methyl)phenyl)methyl)-5-isoxazolyl)-pyridinium acetic acid solvate obtained in Example 6 of the present invention.
Figure 6:
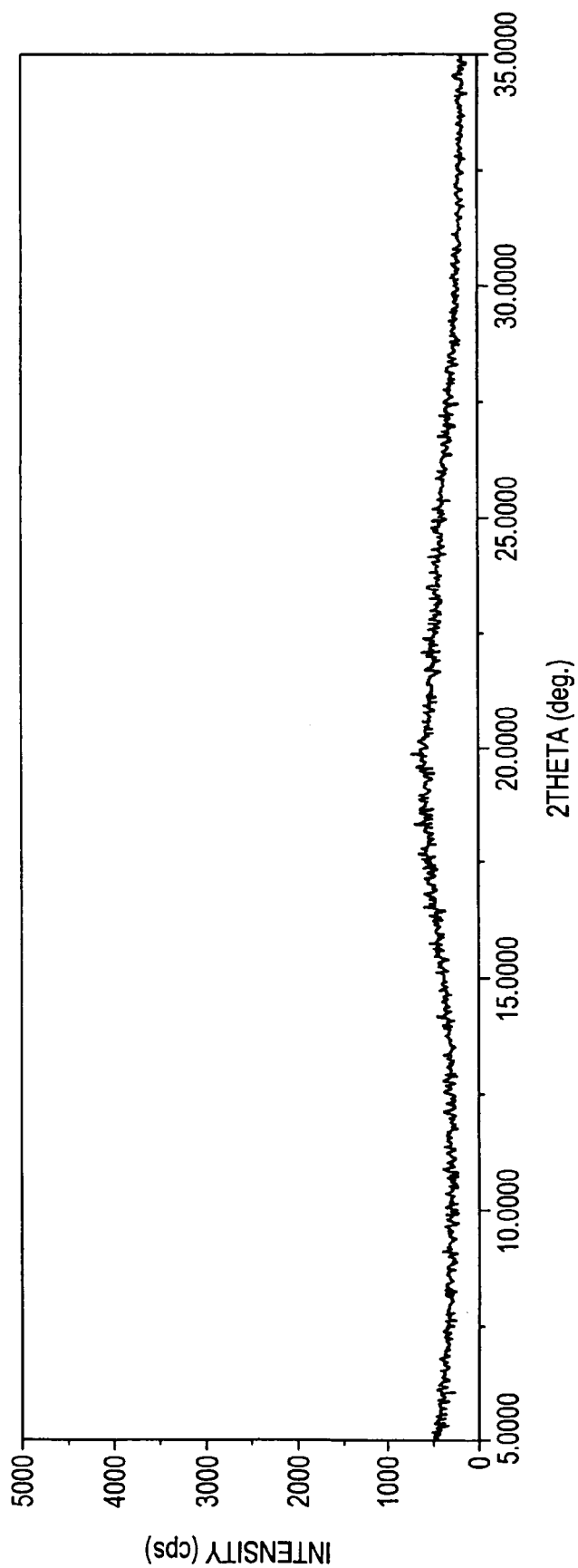
FIG. 6 shows the X-ray diffraction pattern of 2-amino-1-((phosphonoxy)methyl)-3-(3-((4-((2-pyridinyloxy)methyl)phenyl)methyl)-5-isoxazolyl)-pyridinium amorphous obtained in Example 7 of the present invention.
Figure 7:
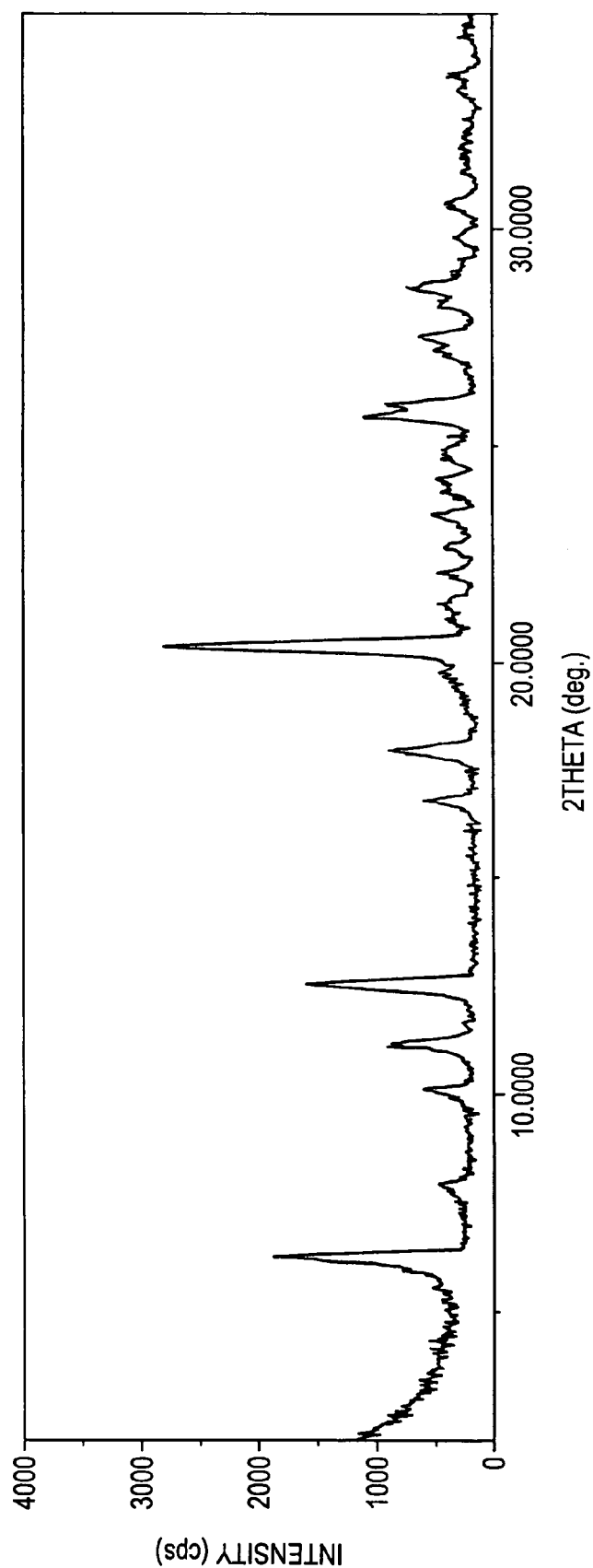
FIG. 7 shows the X-ray diffraction pattern of 2-amino-1-((phosphonoxy)methyl)-3-(3-((4-((2-pyridinyloxy)methyl)phenyl)methyl)-5-isoxazolyl)-pyridinium monohydrochloride obtained in Example 8 of the present invention.
Figure 8:
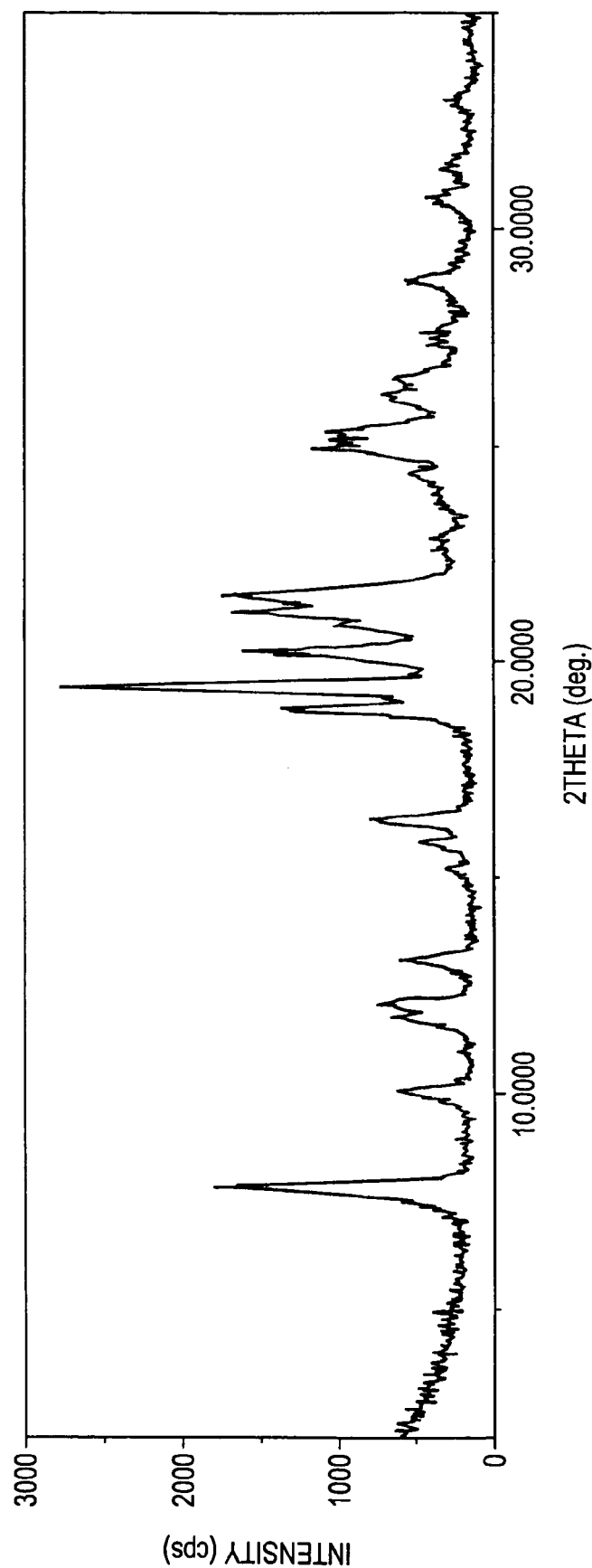
FIG. 8 shows the X-ray diffraction pattern of 2-amino-1-((phosphonoxy)methyl)-3-(3-((4-((2-pyridinyloxy)methyl)phenyl)methyl)-5-isoxazolyl)-pyridinium hemisulfate obtained in Example 10 of the present invention.
Figure 9:
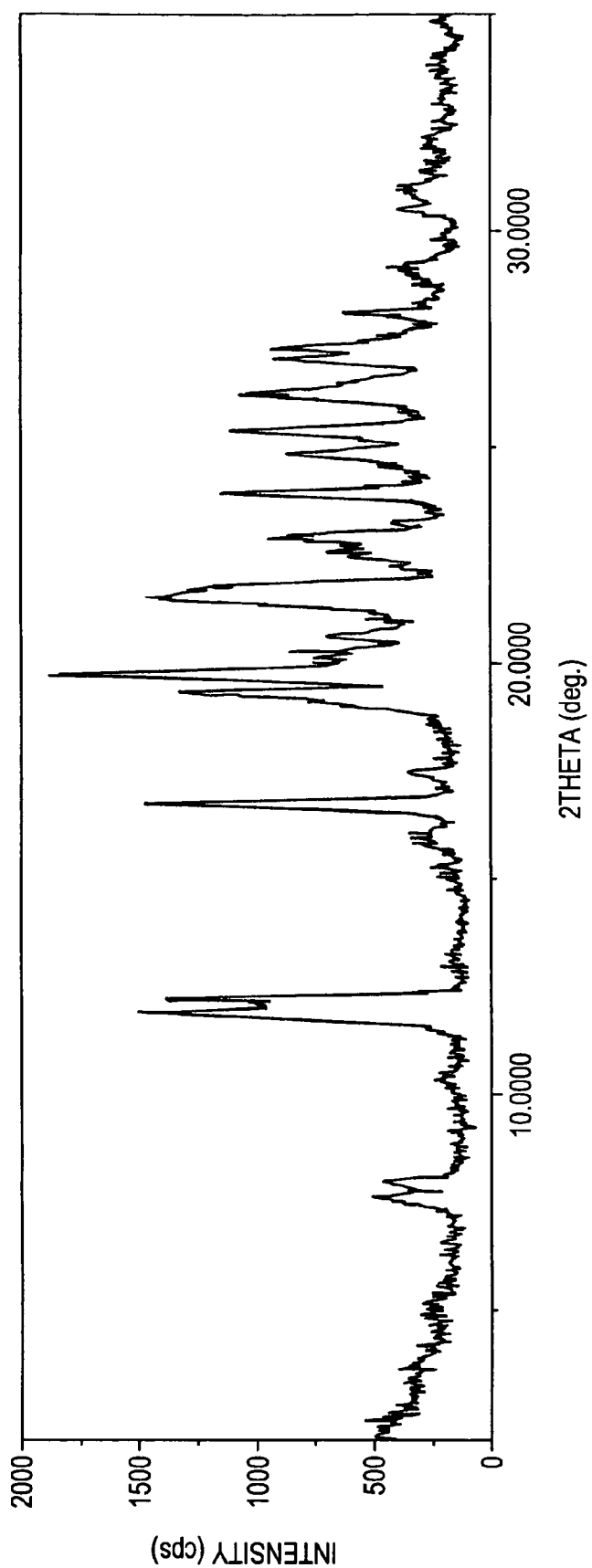
FIG. 9 shows the X-ray diffraction pattern of 2-amino-1-((phosphonoxy)methyl)-3-(3-((4-((2-pyridinyloxy)methyl)phenyl)methyl)-5-isoxazolyl)-pyridinium mononitrate obtained in Example 11 of the present invention.
Figure 10:
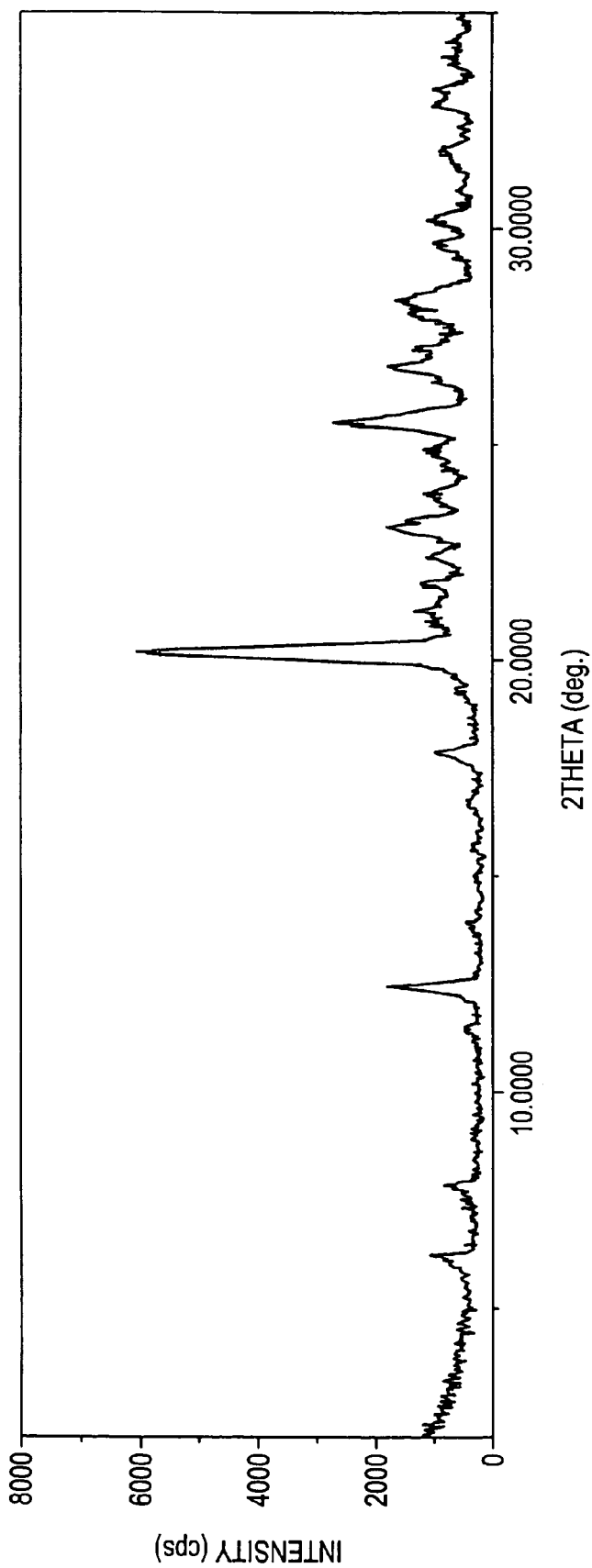
FIG. 10 shows the X-ray diffraction pattern of 2-amino-1-((phosphonoxy)methyl)-3-(3-((4-((2-pyridinyloxy)methyl)phenyl)methyl)-5-isoxazolyl)-pyridinium monohydrobromide obtained in Example 12 of the present invention.
Figure 11:
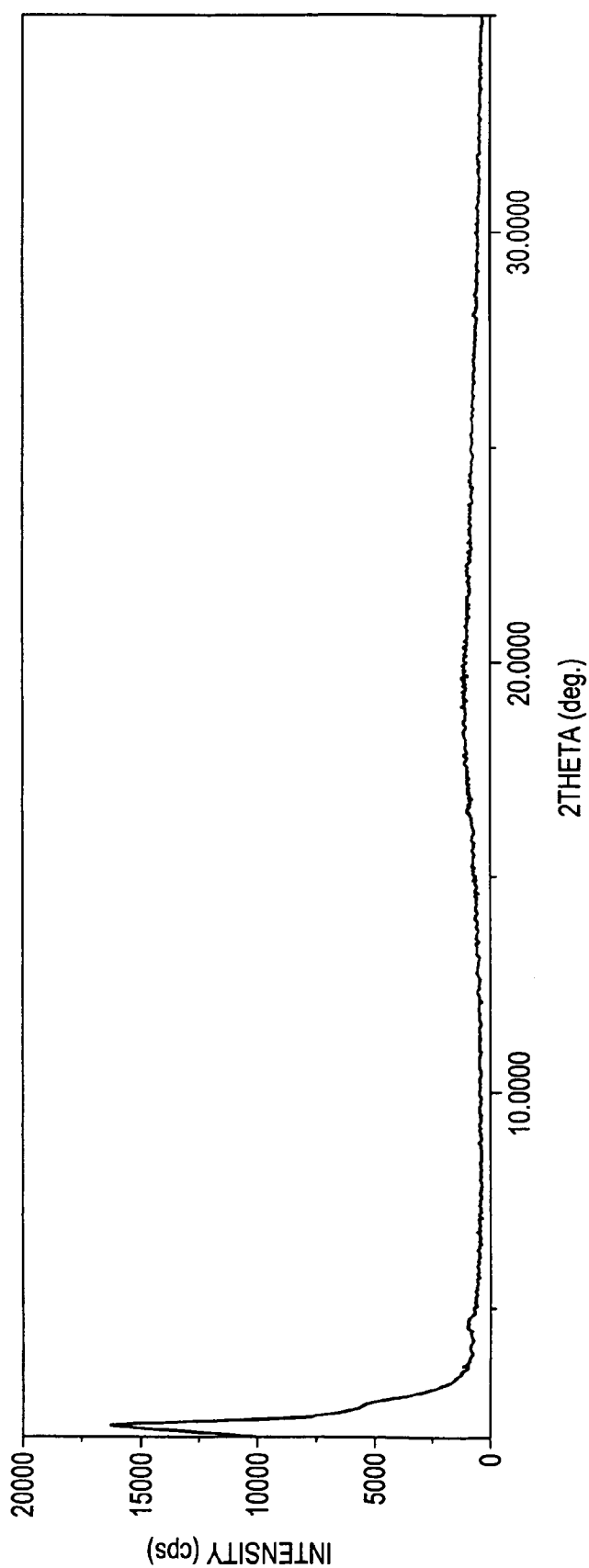
FIG. 11 shows the X-ray diffraction pattern of 2-amino-1-((phosphonoxy)methyl)-3-(3-((4-((2-pyridinyloxy)methyl)phenyl)methyl)-5-isoxazolyl)-pyridinium sodium salt obtained in Example 13 of the present invention.
Figure 12:
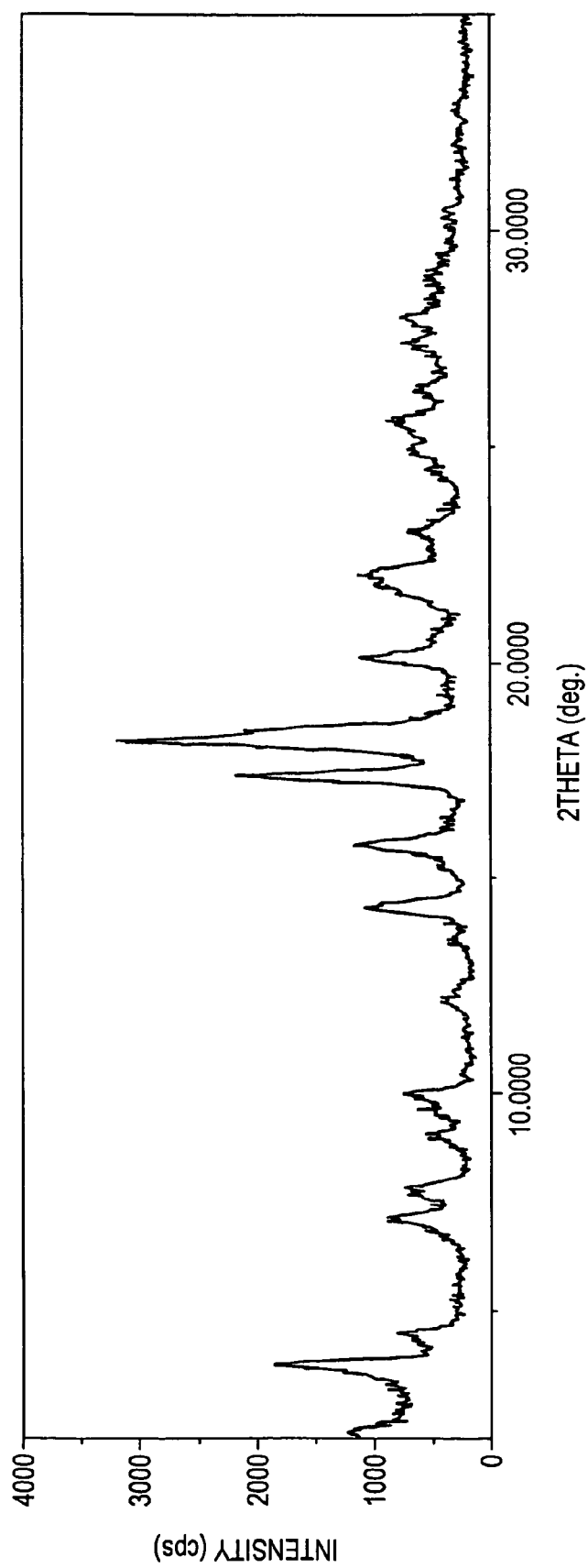
FIG. 12 shows the X-ray diffraction pattern of 2-amino-1-((phosphonoxy)methyl)-3-(3-((4-((2-pyridinyloxy)methyl)phenyl)methyl)-5-isoxazolyl)-pyridinium hemicalcium salt obtained in Example 14 of the present invention.
Figure 13:
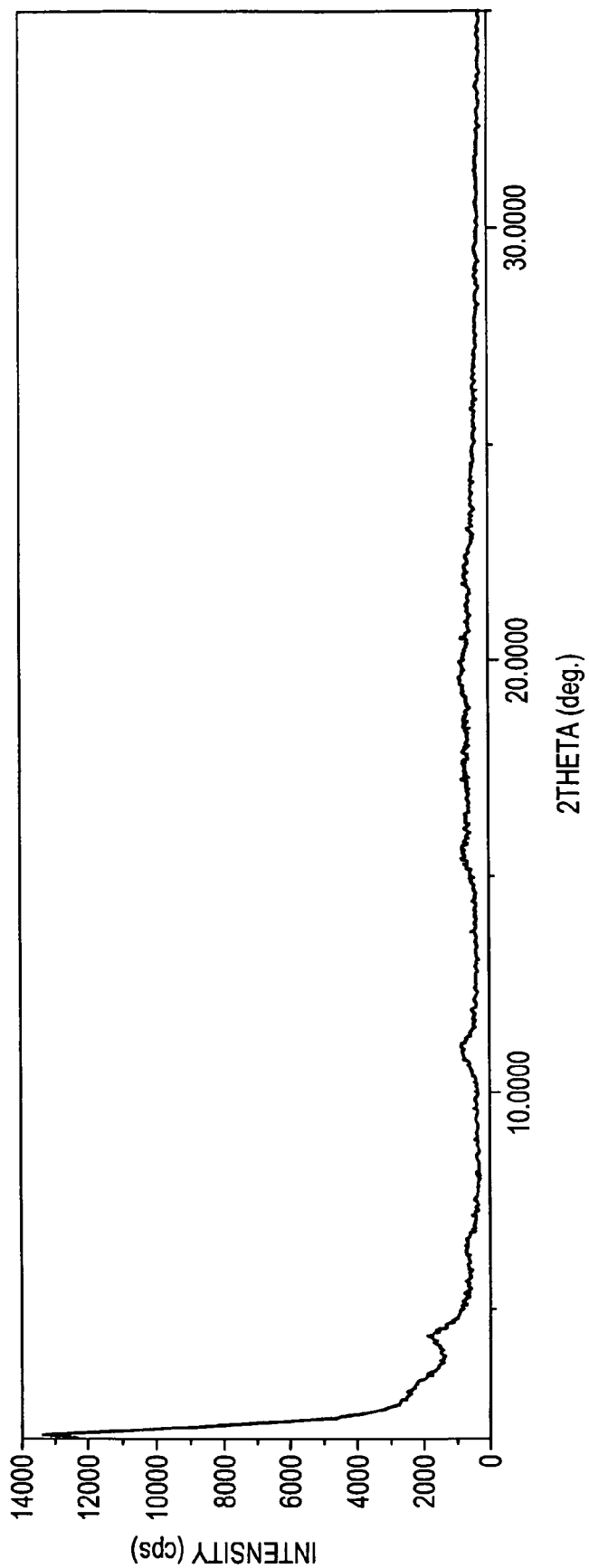
FIG. 13 shows the X-ray diffraction pattern of 2-amino-1-((phosphonoxy)methyl)-3-(3-((4-((2-pyridinyloxy)methyl)phenyl)methyl)-5-isoxazolyl)-pyridinium lithium salt obtained in Example 15 of the present invention.
Figure 14:
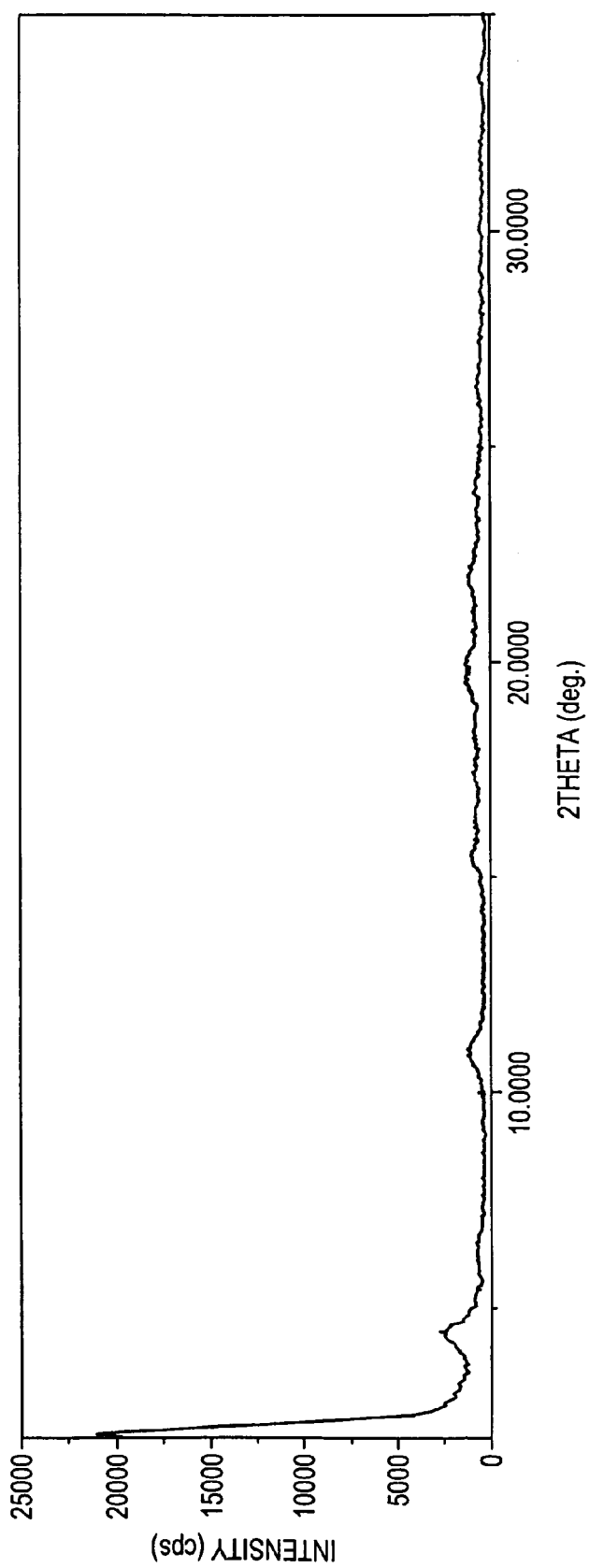
FIG. 14 shows the X-ray diffraction pattern of 2-amino-1-((phosphonoxy)methyl)-3-(3-((4-((2-pyridinyloxy)methyl)phenyl)methyl)-5-isoxazolyl)-pyridinium potassium salt obtained in Example 16 of the present invention.

The present invention is explained below in more detail by reference to the symbols and the terms used herein being defined and the following examples. The present invention is not limited to the following embodiments, however, and various modifications can be made without departing from the gist thereof.

Herein, a structural formula of a compound sometimes represents a certain isomer for convenience of description. However, compounds according to the present invention may include all possible isomers, such as structurally possible geometric isomers, optical isomers generated due to the presence of asymmetric carbons, stereoisomers, tautomers, and mixtures of isomers, and are not limited to formulae being used for the convenience of description, and may be either one of two isomers or a mixture of both isomers. Thus, the compounds according to the present invention may be either optically active compounds having an asymmetric carbon atom in their molecules or their racemates, and are not restricted to either of them but include both. Furthermore, the compounds according to the present invention may exhibit crystalline polymorphism, but likewise are not restricted to any one of these, but may be in any one of these crystal forms or exist as a mixture of two or more crystal forms. The compounds according to the present invention also include both anhydrous and solvates such as hydrated forms.

The term "$C_{1-6}$ alkyl group" used in the present specification refers to a straight-chain or branched-chain alkyl group with 1 to 6 carbon atoms which is a monovalent group induced by removal of any one hydrogen atom from an aliphatic hydrocarbon with 1 to 6 carbon atoms. Specifically, examples of "$C_{1-6}$ alkyl group" may include a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a neopentyl group, a 1-methylbutyl group, a 2-methylbutyl group, a 1,1-dimethylpropyl group, a 1,2-dimethylpropyl group, a n-hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,1,2,-trimethylpropyl group, a 1,2,2-trimethylpropyl group, a 1-ethyl-1-methylpropyl group, a 1-ethyl-2-methylpropyl group or the like, preferably a methyl group, an ethyl group, a n-propyl group, an isopropyl group, a n-butyl group, an isobutyl group, a sec-butyl group or a tert-butyl group or the like.

The term "$C_{2-6}$ alkenyl group" used in the present specification refers to a straight-chain or branched-chain alkenyl group with 2 to 6 carbon atoms which may contain 1 or 2 double bonds. Specifically, examples of "$C_{2-6}$ alkenyl group" may include an ethenyl group, a 1-propenyl group, a 2-propenyl group, a 1-butenyl group, a 2-butenyl group, a 3-butenyl group, a 2-methyl-1-propenyl group, a pentenyl group, a 3-methyl-2-butenyl group, a hexenyl group, a hexanedienyl group or the like, preferably an ethenyl group, a 1-propenyl group, a 2-propenyl group, a 1-butenyl group, a 2-butenyl group, a 3-butenyl group, a 2-methyl-1-propenyl group, a 3-methyl-2-butenyl group or the like.

The term "$C_{2-6}$ alkynyl group" used in the present specification refers to a straight-chain or branched-chain alkynyl chain with 2 to 6 carbon atoms which may contain 1 or 2 triple bonds. Specifically, examples of "$C_{2-6}$ alkynyl group" may include an ethynyl group, a 1-propynyl group, a 2-propynyl group, a 1-butynyl group, a 2-butynyl group, a 3-butynyl group, a pentynyl group, a hexynyl group, a hexanediynyl group or the like, preferably an ethynyl group, a 1-propynyl group, a 2-propynyl group, a 1-butynyl group, a 2-butynyl group, a 3-butynyl group or the like.

The term "$C_{3-8}$ cycloalkyl group" used in the present specification refers to a cyclic aliphatic hydrocarbon group with 3 to 8 carbon atoms. Specifically, examples of "$C_{3-8}$ cycloalkyl group" may include a cyclopropyl group, a cyclobutyl group, a cyclopentyl group, a cyclohexyl group, a cycloheptyl group, a cyclooctyl group or the like, preferably a cyclopropyl group, a cyclobutyl group, a cyclopentyl group, a cyclohexyl group or the like.

The term "$C_{1-6}$ alkoxy group" used in the present specification refers to a group in which an oxygen atom is bonded to terminus of the "$C_{1-6}$ alkyl group" defined above. Specifically, examples of "$C_{1-6}$ alkoxy group" may include a methoxy group, an ethoxy group, a n-propoxy group, an isopropoxy group, a n-butoxy group, an isobutoxy group, a sec-butoxy group, a tert-butoxy group, a n-pentyloxy group, an isopentyloxy group, a sec-pentyloxy group, a neopentyloxy group, a 1-methylbutoxy group, a 2-methylbutoxy group, a 1,1-dimethylpropoxy group, a 1,2-dimethylpropoxy group, a n-hexyloxy group, an isohexyloxy group, a 1-methylpentyloxy group, a 2-methylpentyloxy group, a 3-methylpentyloxy group, a 1,1-dimethylbutoxy group, a 1,2-dimethylbutoxy group, a 2,2-dimethylbutoxy group, a 1,3-dimethylbutoxy group, a 2,3-dimethylbutoxy group, a 3,3-dimethylbutoxy group, a 1-ethylbutoxy group, a 2-ethylbutoxy group, a 1,1,2-trimethylpropoxy group, a 1,2,2-trimethylpropoxy group, a 1-ethyl-1-methylpropxy group, a 1-ethyl-2-methylpropoxy group or the like, preferably a methoxy group, an ethoxy group, a n-propoxy group, an isopropoxy group, a n-butoxy group, an isobutoxy group, a sec-butoxy group, a tert-butoxy group or the like.

The term "hydroxyl $C_{1-6}$ alkyl group" used in the present specification refers to a group in which any of the hydrogen atoms in a "$C_{1-6}$ alkyl group" as defined above has been replaced with a hydroxyl group. Specifically, examples of "hydroxyl $C_{1-6}$ alkyl group" may include a hydroxymethyl group, a 1-hydroxyethyl group, a 2-hydroxyethyl group, a 1-hydroxy-n-propyl group, a 2-hydroxy-n-propyl group, a 3-hydroxy-n-propyl group, a 1-hydroxy-isopropyl group, a 2-hydroxy-isopropyl group, a 3-hydroxy-isopropyl group, a 1-hydroxy-tert-butyl group or the like, preferably a hydroxymethyl group, a 1-hydroxyethyl group, a 2-hydroxyethyl group or the like.

The term "cyano $C_1$ to $C_6$ alkyl group" used in the present specification refers to a group in which any hydrogen atom in the "$C_{1-6}$ alkyl group" defined above has been replaced with a cyano group. Specific examples of "cyano $C_1$ to $C_6$ alkyl group" include a cyanomethyl group, a 1-cyanoethyl group, a 2-cyanoethyl group, a 1-cyano-n-propyl group, a 2-cyano-n-propyl group, a 3-cyano-n-propyl group, a 1-cyano-isopropyl group, a 2-cyano-isopropyl group, a 3-cyano-isopropyl group, and a 1-cyano-tert-butyl group, preferably a cyanomethyl group, a 1-cyanoethyl group, a 2-cyanoethyl group, or the like.

The term "$C_{1-6}$ alkoxycarbonyl group" used in the present specification refers to a group in which a carbonyl group is bonded to terminus of the "$C_{1-6}$ alkoxy group" defined above. Specifically, examples of "$C_{1-6}$ alkoxycarbonyl group" may include a methoxycarbonyl group, an ethoxycarbonyl group, a n-propoxycarbonyl group, an isopropoxycarbonyl group or the like.

The term "$C_{1-6}$ alkoxycarbonyl $C_{1-6}$ alkyl group" used in the present specification refers to a group in which the "$C_{1-6}$ alkyl group" defined above is bonded to terminus of the "$C_{1-6}$ alkoxycarbonyl group" defined above. Specifically, examples of the "$C_{1-6}$ alkoxycarbonyl $C_{1-6}$ alkyl group" may include a methoxycarbonyl methyl group, a methoxycarbonyl ethyl group, an ethoxycarbonyl methyl group, an ethoxycarbonyl ethyl group or the like.

The term "$C_{6-10}$ aryl group" used in the present specification refers to an aromatic hydrocarbon cyclic group with 6 to 10 carbon atoms. Specifically, examples of "$C_{6-10}$ aryl group" may include a phenyl group, a 1-naphthyl group, a 2-naphthyl group, an indenyl group, an azulenyl group, a heptalenyl group or the like, preferably a phenyl group, a 1-naphthyl group, 2-naphthyl group or the like.

The term "$C_{1-6}$ alkoxy $C_{1-6}$ alkyl group" used in the present specification refers to a group in which any of the hydrogen atoms in a "$C_{1-6}$ alkyl group" as defined above has been replaced with a "$C_{1-6}$ alkoxy group" as defined above. Specifically, examples of "$C_{1-6}$ alkoxy $C_{1-6}$ alkyl group" may include a methoxymethyl group, an ethoxymethyl group, a n-propoxymethyl group, a methoxyethyl group, an ethoxyethyl group or the like.

The term "halogen atom" used in the present specification refers a fluorine atom, a chlorine atom, a bromine atom or an iodine atom.

The term "hetero atom" used in the present specification refers to a nitrogen atom, a sulfur atom or an oxygen atom.

The term "5- or 6-member heteroaryl ring" used in the present specification refers to an aromatic ring in which the number of atoms making up the ring is 5 or 6, and 1 or more hetero atoms are included in the atoms making up the ring. Specifically, examples of "5- or 6-member heteroaryl ring" may include a furan ring, a thiophene ring, a pyrrole ring, a pyridine ring, a pyrazine ring, a pyridazine ring, a pyrimidine ring, a triazole ring (a 1,2,3-triazole ring, a 1,2,4-triazole ring, etc.), a tetrazole ring (a 1H-tetrazole ring, a 2H-tetrazole ring, etc.), a thiazole ring, a pyrazole ring, an oxazole ring, an isoxazole ring, an isothiazole ring, an oxadiazole ring, a thiadiazole ring or the like.

The term "5- or 6-member heteroaryl group" used in the present specification refers to a monovalent group induced by removing 1 hydrogen atom from any position in an aromatic ring in which the number of atoms making up the ring is 5 or 6 and one or more hetero atoms are included in the atoms making up the ring. Specifically, examples of "5- or 6-member heteroaryl group" may include a furyl group (a 2-furyl group or a 3-furyl group, etc.), a thienyl group (a 2-thienyl group or a 3-thienyl group, etc.), a pyrrolyl group (a 1-pyrrolyl group, a 2-pyrrolyl group or a 3-pyrrolyl group, etc.), a pyridyl group (a 2-pyridyl group, a 3-pyridyl group, a 4-pyridyl group, etc.), a pyrazinyl group, a pyridazinyl group (a 3-pyridazinyl group or a 4-pyridazinyl group, etc.), a pyrimidinyl group (a 2-pyrimidinyl group, a 4-pyrimidinyl group or a 5-pyrimidinyl group, etc.), a triazolyl group (a 1,2,3-triazolyl group or a 1,2,4-triazolyl group, etc.), a tetrazolyl group (a 1H-tetrazolyl group or a 2H-tetrazolyl group, etc.), a thiazolyl group (a 2-thiazolyl group, a 4-thiazolyl group or a 5-thiazolyl group, etc.), a pyrazolyl group (a 3-pyrazolyl group or a 4-pyrazolyl group, etc.), an oxazolyl group (a 2-oxazolyl group, a 4-oxazolyl group or a 5-oxazolyl group, etc.), an isoxazolyl group (a 3-isoxazolyl group, a 4-isoxazolyl group or a 5-isoxazolyl group, etc.), an isothiazolyl group (a 3-isothiazolyl group, a 4-isothiazolyl group or a 5-isothiazolyl group, etc.), an oxadiazolyl group, a thiadiazolyl group or the like.

The term "5- or 6-member non-aromatic heterocyclic group" used in the present specification refers to a monovalent group induced by removing 1 hydrogen atom from any position in a non-aromatic ring in which the number of atoms making up the ring is 5 or 6 and 1 or more hetero atoms are included in the atoms making up the ring. Specifically, examples of "5- or 6-member non-aromatic heterocyclic group" may include a pyrrolidinyl group, a piperadinyl group, a piperidinyl group, a morpholinyl group, a tetrahydrofuryl group, a tetrahydropyranyl group or the like.

The term "di $C_{1-6}$ alkylamino group" used in the present specification refers to a group in which 2 hydrogen atoms of the amino group are replaced with the "$C_{1-6}$ alkyl groups" defined above being the same as or different from each other. Specifically, examples of the term "di $C_{1-6}$ alkylamino group" may include a N,N-dimethylamino group, a-N,N-diethylamino group, a N,N-di-n-propylamino group, a N, N-di-isopropylamino group, a N,N-di-n-butylamino group, a N,N-isobutylamino group, a N,N-di-sec-butylamino group, a N,N-di-tert-butylamino group, a N-ethyl-N-methylamino group, a N-n-propylamino-N-methylamino group, a N-isopropyl-N-methylamino group, a N-n-butyl-N-methylamino group, a N-isobutyl-N-methylamino group, a N-sec-butyl-N-methylamino group, a N-tert-butyl-N-methylamino group or the like, preferably a N,N-dimethylamino group, a N,N-diethylamino group, N-ethyl-N-methylamino group or the like.

The term "may have 1 or 2 substituents" used in the specification means that there may be 1 or 2 substituents in any combination in sites capable of substituting.

The term "$Q^-$" used in the present specification refers to a pharmaceutically acceptable anion, and as long as it originates from a pharmaceutically acceptable organic acid or inorganic acid, it is not limited to specific anions. Examples of these organic acids or inorganic acids may include the following. Specifically examples of the organic acids may include aliphatic, aromatic, and other such acids, such as methanesulfonic acid, benzenesulfonic acid, maleic acid, citric acid, succinic acid, fumaric acid, toluenesulfonic acid, trifluoromethanesulfonic acid, and the like. Examples of the inorganic acids may include hydrochloric acid, sulfuric acid, phosphoric acid, hydrofluoric acid, hydrobromic acid, hydriodic acid, and the like.

The term "$J^+$" used in the present specification refers to a pharmaceutically acceptable cation, and while not limited to the following cations. Specific examples thereof may include alkali metal ions such as sodium ions, potassium ions, lithium ions, and the like; alkali earth ions such as calcium ions, magnesium ions, and the like; alkylamines such as methylamine, ethylamine, cyclohexylamine, and the like; alkylamines that have been substituted with a hydroxyl group, such as diethanolamine, triethanolamine, tris(hydroxymethyl)-aminomethane and the like; amino acids such as lysine, arginine, histidine, and the like; and organic base-derived ammonium ions such as piperidine, morpholine, and the like.

$R^1$ represents a hydrogen atom, a halogen atom, an amino group, a $C_{1-6}$ alkyl group, a $C_{1-6}$ alkoxy group, a $C_{1-6}$ alkylamino group, a hydroxy $C_{1-6}$ alkylamino group, or a $C_{1-6}$ alkoxy $C_{1-6}$ alkyl group, with a hydrogen atom, an amino group, or a $C_{1-6}$ alkoxy $C_{1-6}$ alkyl group being particularly favorable, and with a methoxymethyl group being preferable as the $C_{1-6}$ alkoxy $C_{1-6}$ alkyl group.

$R^2$ represents a hydrogen atom, an amino group, or a di-$C_{1-6}$ alkylamino group, with a hydrogen atom or an amino group being preferable.

One of X and Y represents a nitrogen atom, and the other represents a nitrogen atom or an oxygen atom.

The partial structure represented by the following formula (II) including X and Y:

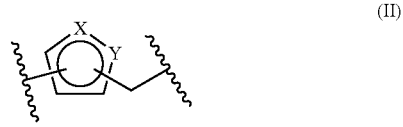

(II)

preferably has the structure represented below, in which each left end is bonded to the 3-position of a pyridine ring via a single bond, and the right end is bonded to an A ring via a methylene group:

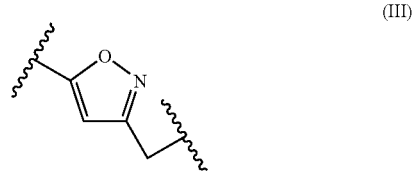

(III)

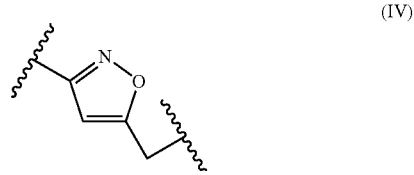

(IV)

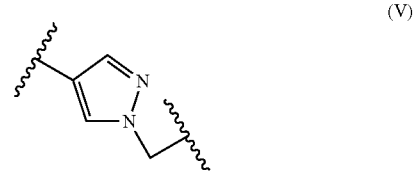

(V)

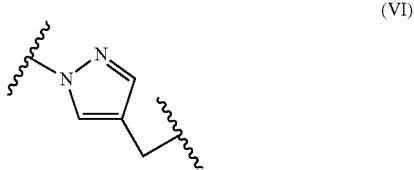

(VI)

For example, in the case of the partial structure of formula (III), the structure of the parent compound of the compound according to the present invention, that is, a compound prior to the introduction of a phosphonoxymethyl group, is represented by the following formula:

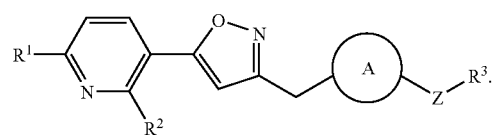

It is preferable when one of X and Y represents a nitrogen atom and the other represents an oxygen atom, or when both of X and Y represents nitrogen atoms, and when one of X and Y represents a nitrogen atom and the other represents an oxygen atom, the partial structure represented by the following formula (II) including X and Y

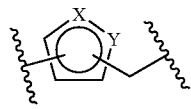
(II)

preferably has the structure represents the following formula (III) or (IV), in which each left end is bonded to the 3-position of a pyridine ring via a single bond, and the right end is bonded to an A ring via a methylene group:

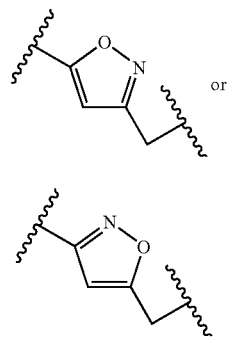
(III)

or (IV)

Also, when both of X and Y represent nitrogen atoms, the partial structure represented by the following formula (II) including X and Y

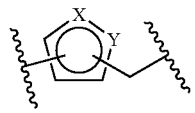
(II)

preferably has the structure represented the following formula (V) or (VI), in which each left end is bonded to the 3-position of a pyridine ring via a single bond, and the right end is bonded to an A ring via a methylene group:

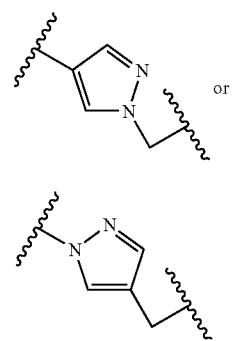
(V)

or (VI)

The ring A represents a 5- or 6-member heteroaryl ring or a benzene ring, which may have one or two halogen atoms or $C_{1-6}$ alkyl groups, and preferably represents a pyridine ring, a benzene ring, a furan ring, a thiophene ring, or a pyrrole ring, with a pyridine ring, a benzene ring, or a thiophene ring being more preferable, and a pyridine ring or a benzene ring being particularly preferable.

Z represents a single bond, a methylene group, an ethylene group, an oxygen atom, a sulfur atom, —$CH_2O$—, —$OCH_2$—, —NH—, —$NHCH_2$—, —$CH_2NH$—, —$CH_2S$—, or —$SCH_2$—, of which a methylene group, an oxygen atom, —$CH_2O$—, or —$OCH_2$— is preferred, with an oxygen atom, —$CH_2O$—, or —$OCH_2$— being particularly preferable.

$R^3$ represents a hydrogen atom or a halogen atom, or represents a $C_{1-6}$ alkyl group, a $C_{3-8}$ cycloalkyl group, a $C_{6-10}$ aryl group, or a 5- or 6-member heteroaryl group, each of which may have one or two substituents selected from a substituent group α.

[Substituent Group α]

a halogen atom, a cyano group, a $C_{1-6}$ alkyl group, a $C_{1-6}$ alkoxy group, a $C_{1-6}$ alkoxycarbonyl, a $C_{3-8}$ cycloalkyl group, a $C_{2-6}$ alkenyl group, and a $C_{2-6}$ alkynyl group.

Preferable examples of $R^3$ may include an n-butyl group, a cyclopropyl group, a phenyl group, a fluorophenyl group, a furyl group, a chlorofuryl group, a methylfuryl group, a thienyl group, a bromothienyl group, a methylthienyl group, a pyridyl group, and a methylpyridyl group, with an n-butyl group, a cyclopropyl group, a phenyl group, a fluorophenyl group, a pyridyl group, and a methylpyridyl group being particularly preferable.

Z and $R^3$ can be combined as necessary to configure substituents for the ring A. Preferable examples of $R^3$—Z— as substituents of the ring A thus configured may include a phenoxy group, a benzyloxy group, a 2-fluoro-benzyloxy group, a 3-fluoro-benzyloxy group, a 4-fluoro-benzyloxy group, a pyridin-2-yloxymethyl group, a 6-methyl-pyridin-2-yloxymethyl group, a pyridin-2-ylmethoxy group, a 6-methyl-pyridin-2-ylmethoxy group, a 4-methyl-pyridin-2-ylmethoxy group, a butoxymethyl group, and a cyclopropylmethoxy group.

The term "salt" used in the present specification refers to a salt with a compound or an atom capable of forming a monovalent counter ion or a divalent counter ion. Examples thereof may include salts of inorganic acid (for example, hydrochloric acid, hydrobromic acid, phosphoric acid, sulfuric acid, nitric acid and the like), and salts of organic acid (for example, methanesulfonic acid, ethanesulfonic acid, benzenesulfonic acid, p-toluenesulfonic acid, fumaric acid, maleic acid, succinic acid, citric acid, malic acid, trifluoroacetic acid and the like), or salts of inorganic bases (for example, sodium salt, potassium salt, calcium salt, lithium salt and the like), and salts of organic bases (for example, methylamine salt, ethylamine salt, tert-butylamine salt, cyclohexylamine salt, N-methyl-D-glucamine salt, lysine salt, piperidine salt, morpholine salt and the like). The term "salt" includes mono- and bis-salts. The salt of the compound according to the present invention includes solvates of this salt such as anhydrous form and hydrate of this salt.

The term "antifungal agent" used in the present specification refers to a preventive agent or a therapeutic agent for fungal infection.

The compounds according to the present invention can be formulated into tablets, powders, fine granules, granules, coated tablets, capsulates, syrups, troches, inhalants, suppositories, injections, ointments, eye ointments, tapes, eye drops, nose drops, ear drops, cataplasms, lotions or the like, by the conventional methods.

Such formulation can be achieved by using typical diluents, binders, lubricants, colorants, flavorants, and, as necessary, stabilizers, emulsifiers, absorbefacients, surfactants, pH modulators, preservatives, antioxidants or the like, and materials commonly used as ingredients of pharmaceutical preparations according to the conventional methods. For example, an oral preparation can be produced by combining a compound of the present invention or a pharmaceutically acceptable salt thereof with a diluent, and if required, a binder, a disintegrating agent, a lubricant, a colorant, a flavorant or the like, and formulating the mixture into powders, fine granules, granules, tablets, coated tablets, capsules or the like according to the conventional methods.

Examples of these materials may include animal and vegetable oils such as soy bean oil, beef tallow, and synthetic glyceride; hydrocarbons such as liquid paraffin, squalane, and solid paraffin; ester oils such as octyldodecyl myristate and iso-propyl myristate; higher alcohols such as cetostearyl alcohol and behenyl alcohol; silicone resins; silicone oils; surfactants such as polyoxyethylene fatty acids ester, sorbitan fatty acid ester, polyoxyethylene sorbitan fatty acid ester, polyoxyethylene hydrogenated castor oil, and polyoxyethylene polyoxypropylene block co-polymer; water-soluble polymers such as hydroxyethyl cellulose, polyacrylic acid, carboxyvinyl polymer, polyethylene glycol, polyvinylpyrrolidone, and methyl cellulose; lower alcohols such as ethanol and isopropanol; polyhydric alcohols such as glycerol, propylene glycol, dipropylene glycol, and sorbitol; sugars such as glucose and sucrose; inorganic powder such as anhydrous silicic acid, magnesium aluminum silicate, and aluminum silicate; and pure water. Examples of the diluents may include lactose, corn starch, white sugar, glucose, mannitol, sorbitol, crystalline cellulose, silicon dioxide or the like. Examples of the binders may include polyvinyl alcohol, polyvinyl ether, methylcellulose, ethylcellulose, gum Arabic, tragacanth, gelatin, shellac, hydroxypropyl methylcellulose, hydroxypropyl cellulose, polyvinylpyrrolidone, polypropylene glycol-polyoxyethylene block co-polymer, meglumine or the like. Examples of disintegrating agents may include starch, agar, gelatin powder, crystalline cellulose, calcium carbonate, sodium hydrogencarbonate, calcium citrate, dextrin, pectin, calcium carboxymethyl cellulose or the like. Examples of lubricants may include magnesium stearate, talc, polyethylene glycol, silica, hydrogenated vegetable oil or the like. Examples of colorants may include those pharmaceutically acceptable. Examples of flavorants may include cocoa powder, peppermint camphor, aromatic powder peppermint oil, Borneo camphor, cinnamon powder or the like.

Tablets and granules may be coated with sugar, or if required, other appropriate coatings can be made. Solutions, such as syrups or injectable preparations, to be administered can be formulated by combining a compound according to the present invention or a pharmaceutically acceptable salt thereof with a pH modulator, a solubilizing agent, an isotonizing agent or the like, and if required, with an auxiliary solubilizing agent, a stabilizer or the like, according to the conventional methods. Methods for manufacturing external preparations are not limited and such preparations can be manufactured by the conventional methods. Specifically, various materials typically used for manufacturing pharmaceuticals, quasi drugs, cosmetics or the like can be used as base materials for the external formulation. More specifically, examples of base materials to be used may include animal and vegetable oils, minerals oils, ester oils, wax, higher alcohols, fatty acids, silicone oil, surfactants, phospholipids, alcohols, polyhydric alcohols, water-soluble polymers, clay minerals, pure water or the like. Furthermore, external preparations of the present invention can contain, as required, pH modulators, antioxidants, chelating agents, antibacterial/antifungal agents, colorants, odoriferous substances or the like. But this does not limit the type of base materials that are to be used in the external preparations of the present invention. If required, the preparation may contain differentiation inducers, blood flow improving agents, antimicrobial agents, antiphologistics, cell activators, vitamins, amino acids, humectants, keratolytic agents or the like. The amount of the base materials listed above is adjusted within a concentration range used for producing typical external preparations.

When administering the compound according to the present invention, the forms of the compounds are not limited in particular, and the compound can be given orally or parenterally by the conventional method. For instance, the compound can be administered as a dosage form such as tablets, powders, granules, capsules, syrups, troches, inhalants, suppositories, injections, ointments, eye ointments, tapes, eye drops, nasal drops, ear drops, cataplasms and lotions.

Dose of a medicament according to the present invention can be selected appropriately according to symptom severity, age, sex, body weight, forms of administration, type of salts, specific type of disease or the like.

The does varies remarkably depending on the patient's disease, symptom severity, age and sex, drug susceptibility or the like. An oral preparation according to the present invention can be generally administered once or several time at a dose of from 1 to 10000 mg/adult/day, preferably from 10 to 2000 mg/adult/day. An injection according to the present invention can be generally administered at a dose of from 0.1 to 10000 mg/adult/day, preferably from 1 to 2000 mg/adult/day.

Typical Manufacture Method

The method for manufacturing the compounds represented by formulas (I), (IA), and (IB) (hereinafter referred to as compound (I), compound (IA), and compound (IB)) will now be described.

Typical Method for Manufacturing Phosphoric Ester
Manufacturing Method 1—Method for Manufacturing Compounds (I), (IA), and (IB)

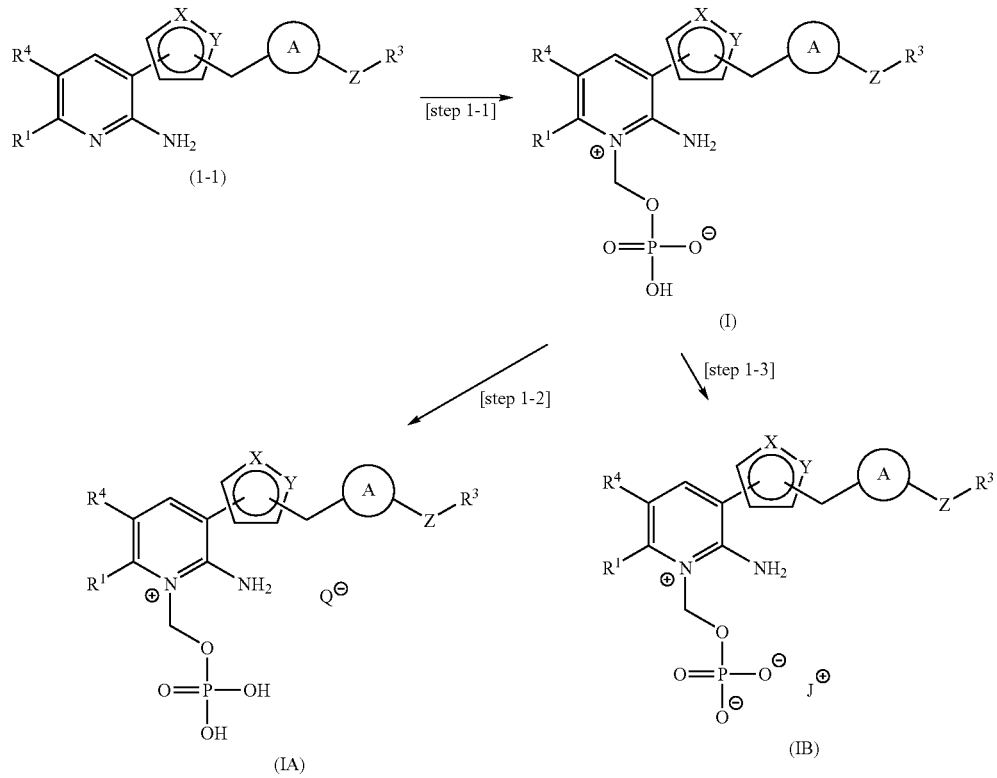

wherein ring A, $R^1$, $R^3$, $R^4$, X, Y, Z, $Q^-$ and $J^+$ have the same meanings as defined above.

Compound (1-1) can be manufactured by the methods described in the following reference examples, etc. Compound (1-1) can also be manufactured by the method described in U.S. Patent 2007/0105904 (A1).

[Step 1-1]

This step is a step wherein after compound (1-1) and phosphoric acid di-tert-butyl ester chloromethyl ester are reacted in the presence of sodium iodide, compound (I) is then obtained by acid treatment.

There are no particular restrictions on the solvent used when compound (1-1) and phosphoric acid di-tert-butyl ester chloromethyl ester are reacted in the presence of sodium iodide, as long as it can dissolve the starting materials to a certain extent without impeding the reaction. Examples of the solvents that can be used may include halogenated hydrocarbon-based solvents such as methylene chloride, chloroform, and the like; ether-based solvents such as tetrahydrofuran, diethyl ether, and the like; ester-based solvents such as ethyl acetate and the like; acetonitrile; tetramethylene sulfolane; and mixtures of these solvents. The use of ethyl acetate, tetrahydrofuran or acetonitrile is preferred. The phosphoric acid di-tert-butyl ester chloromethyl ester can be used in an amount of from 1 to 10 equivalents, and preferably from 1 to 2 equivalents, based on compound (1-1). The sodium iodide can be used in an amount of from 1 to 10 equivalents, and preferably from 1 to 2 equivalents, based on compound (1-1).

The reaction temperature is from 0 to 60° C., and preferably from 4° C. to room temperature. The reaction time is from 4 to 216 hours.

The acid used in the acid treatment may be organic acids such as trifluoroacetic acid or the like; or mineral acids such as hydrochloric acid or the like, with the use of hydrochloric acid, or trifluoroacetic acid being preferred. In the acid treatment, the acid may be added as is to the reaction solvent at a previous stage, or the solvent may first be concentrated under a reduced pressure, and the acid is then added after changing to a suitable solvent such as dichloromethane. The reaction temperature is from −10° C. to room temperature, and the reaction time is from 5 minutes to 2 hours.

[Step 1-2]

This step is a step wherein compound (I) is reacted with an acid to obtain compound (IA). There are no particular restrictions on the acid used in this reaction, so long as it is pharmaceutically acceptable. Examples thereof may include monobasic acids such as hydrochloric acid, hydrobromic acid, nitric acid, and the like; and dibasic acids such as sulfuric acid and the like. There are no particular restrictions on the solvent used in this reaction, so long as it can dissolve the starting materials to a certain extent without impeding the reaction. Examples of the solvents that can be used may include amide-based solvents such as N,N-dimethylformamide, N-methylpyrrolidinone, and the like; alcohol-based solvents such as methanol, ethanol, and the like; tetrahydrofuran; acetonitrile; water; and mixtures of these solvents. The monobasic acid is used in an amount of 1 equivalent based on compound (I), and a dibasic acid is used in an amount of from 1 or 0.5 equivalent based on compound (I). The reaction temperature is from 0° C. to room temperature, and the reaction time is from 5 minutes to 4 hours.

[Step 1-3]

This step is a step wherein compound (I) and a base are reacted to obtain compound (IB). There are no particular restrictions on the base used in this reaction, so long as it is pharmaceutically acceptable. Examples thereof may include inorganic bases such as sodium hydroxide, potassium hydroxide, and the like; and organic bases such as lysine and the like. There are no particular restrictions on the solvent used in this reaction, so long as it can dissolve the starting materials to a certain extent without impeding the reaction. Examples of the solvents that can be used may include amide-based solvents such as N,N-dimethylformamide, N-methylpyrrolidinone, and the like, alcohol-based solvents such as methanol, ethanol, and the like; tetrahydrofuran; acetonitrile; water; and mixtures of these solvents. The monoacid base is used in an amount of 1 equivalent based on compound (I), and a diacid base acid is used in an amount of 1 or 0.5 equivalent based on compound (I). The reaction temperature is from 0° C. to room temperature, and the reaction time is from 5 minutes to 4 hours.

EXAMPLES

The compounds according to the present invention can be manufactured, for example, by the methods described in the following examples, reference examples, and manufacturing examples. However, these are used for illustrative purposes, and the compounds according to the present invention are not in any case limited to the following specific examples.

Reference Example 1

3-(3-(4-(Pyridin-2-yloxymethyl)-benzyl)-isoxazol-5-yl)-pyridin-2-ylamine

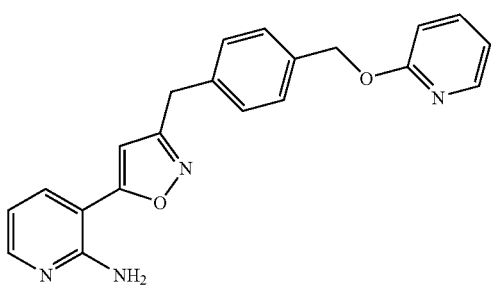 [SMILES: Nc1ncccc1-c1cc(Cc2ccc(COc3ccccn3)cc2)no1]

To a tetrahydrofuran solution (5 mL) of (4-(pyridin-2-yloxymethyl)-phenyl)-acetohydroxymoyl chloride (510 mg, 1.84 mmol) described in Manufacturing Example 1-1-5 and 3-ethynyl-pyridin-2-ylamine (150 mg, 1.27 mmol) described in Manufacturing Example 1-2-3 of International Publication WO 07/052,615 was added triethylamine (708 μL, 5.08 mmol) at room temperature, which was stirred for 95 minutes at room temperature. Water was added to the reaction solution at room temperature, and extracted with ethyl acetate. The organic layer was washed with a saturated saline and dried over anhydrous magnesium sulfate, and the solvent was then evaporated under a reduced pressure. The residue was purified by NH silica gel column chromatography (heptane:ethyl acetate=2:1) to obtain the title compound (120 mg, 26%).

$^1$H-NMR spectrum (CDCl$_3$) δ (ppm): 4.08 (2H, s), 5.37 (2H, s), 6.33 (1H, s), 6.45 (2H, brs), 6.79-6.82 (2H, m), 6.88-6.91 (1H, m), 7.30 (2H, d, J=8.1 Hz), 7.45 (2H, d, J=8.1 Hz), 7.57-7.61 (1H, m), 7.85 (1H, d, J=7.3 Hz), 8.03 (1H, d, J=5.5 Hz), 8.17 (1H, m).

The starting material, (4-(pyridin-2-yloxymethyl)-phenyl)-acetohydroxymoyl chloride was synthesized by the following method.

Manufacturing Example 1-1-1

(4-(Pyridin-2-yloxymethyl)-phenyl)-methanol

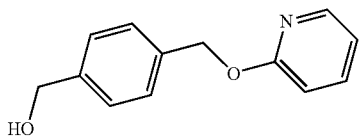 [SMILES: OCc1ccc(COc2ccccn2)cc1]

To a mixture of 1,4-benzenedimethanol (5.5 g, 40 mmol), 2-fluoropyridine (1.3 g, 13 mmol) and N,N-dimethylformamide (15 mL) was added sodium hydride (1.4 g, 40 mmol, 66% in oil) at 0° C., which was stirred for 20 minutes at room temperature and for 1 hour at 70° C. Water was added to the reaction mixture, and extracted with ethyl acetate. The organic layer was washed with a saturated saline, and the solvent was evaporated under a reduced pressure. The residue was purified by NH silica gel column chromatography (ethyl acetate:heptane=1:1) to obtain the title compound (1.9 g, 66%).

$^1$H-NMR spectrum (CDCl$_3$) δ (ppm): 4.71 (2H, s), 5.38 (2H, s), 6.81 (1H, td, J=0.9, 8.4 Hz), 6.89 (1H, ddd, J=0.9, 5.1, 7.1 Hz), 7.37-7.47 (4H, m), 7.59 (1H, ddd, J=2.0, 7.1, 8.3 Hz), 8.17 (1H, ddd, J=0.7, 2.0, 5.1 Hz).

Manufacturing Example 1-1-2

4-(Pyridin-2-yloxymethyl)-benzaldehyde

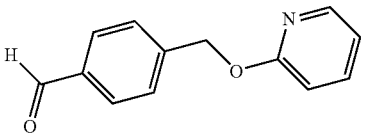 [SMILES: O=Cc1ccc(COc2ccccn2)cc1]

To a mixture of (4-(pyridin-2-yloxymethyl)-phenyl)-methanol (1.9 g, 8.6 mmol) described in Manufacturing Example 1-1-1 and methylene chloride (30 mL) was added manganese dioxide (15 g, 17 mmol) at room temperature, which was stirred overnight at this temperature. The reaction mixture was filtered through a Celite pad, and the solvent was evaporated under a reduced pressure. The residue was purified by silica gel column chromatography (ethyl acetate:heptane=1:4), to obtain the title compound (770 mg, 42%).

¹H-NMR spectrum (CDCl₃) δ (ppm): 5.48 (2H, s), 6.85 (1H, d, J=8.2 Hz), 6.90-6.93 (1H, m), 7.60-7.64 (3H, m), 7.89 (2H, d, J=8.1 Hz), 8.16 (1H, dd, J=1.3, 4.9 Hz), 10.0 (1H, s).

Manufacturing Example 1-1-3

2-(4-((E)-2-Nitro-vinyl)-benzyloxy)-pyridine

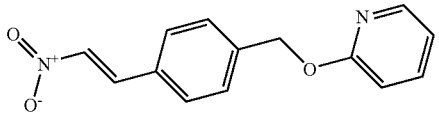 [SMILES: O=[N+]([O-])/C=C/c1ccc(COc2ccccn2)cc1]

A mixture of 4-(pyridin-2-yloxymethyl)-benzaldehyde (23.4 g, 110 mmol) described in Manufacturing Example 1-1-2, nitromethane (33.6 g, 550 mmol), ammonium acetate (17.0 g, 220 mmol), and acetic acid (200 mL) was stirred for 1 hour and 45 minutes at 100° C. A small amount of water was added thereto while the reaction solution was stirred under an ice cooling, and the precipitated solids were collected by filtration, so as to obtain title compound (21.0 g, 74.5%).

¹H-NMR spectrum (DMSO-d₆) δ (ppm): 5.41 (2H, s), 6.91 (1H, dd, J=0.8, 8.4 Hz), 6.99-7.10 (1H, m), 7.53 (2H, d, J=8.0 Hz), 7.72-7.79 (1H, m), 7.86 (2H, d, J=8.0 Hz), 8.13 (1H, d, J=10 Hz), 8.15-8.20 (1H, m), 8.23 (1H, d, J=10 Hz).

Manufacturing Example 1-1-4

2-(4-(2-Nitro-ethyl)-benzyloxy)-pyridine

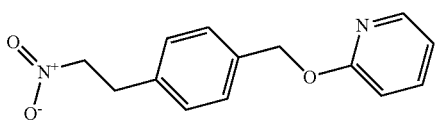 [SMILES: O=[N+]([O-])CCc1ccc(COc2ccccn2)cc1]

To a solution of 2-(4-((E)-2-nitro-vinyl)-benzyloxy)-pyridine (21.0 g, 81.9 mmol) described in Manufacturing Example 1-1-3, acetic acid (21 mL), and dimethyl sulfoxide (200 mL) was added sodium borohydride (4.96 g, 131 mmol) at room temperature while cooling suitably. After the addition of the sodium borohydride, the ice bath was removed, followed by stirring for 15 minutes at room temperature. The reaction solution was separated into water and ethyl acetate. The ethyl acetate layer was washed with water twice and with saline once, and this product was dried over anhydrous magnesium sulfate and the solvent was evaporated under a reduced pressure. The residue was purified by NH silica gel column chromatography (ethyl acetate:heptane=1:3) to obtain the title compound (16.3 g, 77.1%).

¹H-NMR spectrum (DMSO-d₆) δ (ppm): 3.23 (2H, t, J=6.8 Hz), 4.85 (2H, t, J=6.8 Hz), 5.32 (2H, s), 6.82-6.88 (1H, m), 6.96-7.01 (1H, m), 7.28 (2H, d, J=8.0 Hz), 7.38 (2H, d, J=8.0 Hz), 7.69-7.74 (1H, m), 8.15-8.19 (1H, m).

Manufacturing Example 1-1-5

4-(Pyridin-2-yloxymethyl)-phenyl-acetohydroxymoyl chloride

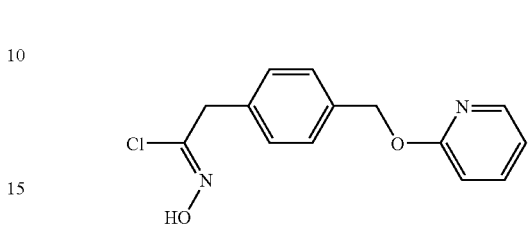

Lithium wire (323 mg, 46.6 mmol) was added to and dissolved in methanol (75 mL). To this solution was added 2-(4-(2-nitro-ethyl)-benzyloxy)-pyridine (6.0 g, 23.3 mmol)) described in Manufacturing Example 1-1-4, and the reaction solution was concentrated under a reduced pressure. Toluene was added to the residue, and this solvent was concentrated under a reduced pressure. A solution of the resulting residue in methylene chloride (90 mL) and tetrahydrofuran (45 mL) was cooled to −78° C., and titanium(IV) chloride (8.15 mL, 74.4 mmol) was added thereto. As soon as the addition of the titanium(IV) chloride was complete, the reaction solution was stirred for 10 minutes at 0° C., and then for 30 minutes at room temperature. The reaction solution was put into an ice water and extracted with ethyl acetate. The organic layer was dried over anhydrous magnesium sulfate, and the magnesium sulfate was filtered off. The filtrate was passed through a glass filter (eluted with ethyl acetate) spread with neutral silica gel. The eluate thus obtained was concentrated under a reduced pressure. A small amount of ethyl acetate was added to the residue, and the precipitated solids were collected by filtration, so as to obtain the title compound (1.86 g, 28.8%).

¹H-NMR spectrum (DMSO-d₆) δ (ppm): 3.82 (2H, s), 5.33 (2H, s), 6.84-6.89 (1H, m), 6.97-7.01 (1H, m), 7.25 (2H, d, J=8.4 Hz), 7.41 (2H, d, J=8.4 Hz), 7.70-7.76 (1H, m), 8.15-8.18 (1H, m), 11.7 (1H, s).

The title compound of Manufacturing Example 1-1-5 can also be synthesized by another method.

Manufacturing Example 1-2-1

2-(4-Bromo-benzyloxy)-pyridine

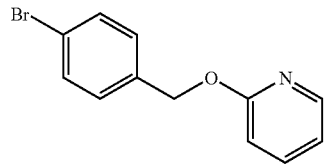 [SMILES: Brc1ccc(COc2ccccn2)cc1]

To a N,N-dimethylformamide solution (125 mL) of 4-bromobenzyl alcohol (25 g, 130 mmol) was added potassium tert-butoxide (15.8 g, 141 mmol) at room temperature, which was stirred for 10 minutes at 54° C. To this reaction solution was added 2-fluoropyridine (15 mL, 154 mmol) at a temperature ranging from 40° C. to 58° C., which was stirred for another 30 minutes at 65° C. The reaction solution was cooled to room temperature, water and ethyl acetate were added thereto, which was separated. The aqueous layer was further extracted with ethyl acetate twice. The ethyl acetate layers were combined, washed with water three times and saline once, and was then dried over anhydrous magnesium sulfate and filtered. The filtrate was concentrated under a reduced pressure. Diethyl ether was added to the residue, and this was concentrated under a reduced pressure, so as to obtain a crude product of the title compound (34 g).

$^1$H-NMR spectrum (DMSO-d$_6$) δ (ppm): 5.33 (2H, s), 6.87-6.90 (1H, m), 6.98-7.02 (1H, m), 7.38-7.44 (2H, m), 7.55-7.60 (2H, m), 7.71-7.76 (1H, m), 8.15-8.18 (1H, m)

Manufacturing Example 1-2-2

4-(Pyridin-2-yloxymethyl)-benzaldehyde

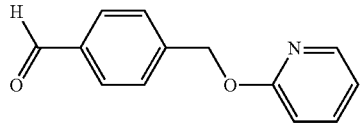 [SMILES: O=Cc1ccc(COc2ccccn2)cc1]

To a tetrahydrofuran solution (120 mL) of 2-(4-bromo-benzyloxy)pyridine (34 g, 128 mmol) described in Manufacturing Example 1-2-1 was added n-butyl lithium (50 mL, 2.6 m, hexane solution 134 mmol) dropwise at −78° C. After stirring for 30 minutes, N,N-dimethylformamide (10 mL, 134 mmol)) was added dropwise at −78° C. to the reaction solution, which was stirred at room temperature. Water and ethyl acetate were added thereto, which was separated. The ethyl acetate layer was washed with water twice and saline once. The aqueous layers were combined and extracted with ethyl acetate. The ethyl acetate layer thus obtained was washed with water twice and saline once. The previously obtained ethyl acetate layer and the ethyl acetate layer obtained this time were combined, dried over anhydrous magnesium sulfate, and filtered. This filtrate was concentrated under a reduced pressure, so as to obtain a crude product of the title compound (26.8 g).

Manufacturing Example 1-2-3

2-(4-((E)-2-Nitro-vinyl)-benzyloxy)-pyridine

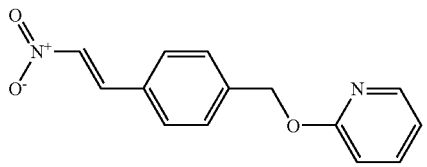 [SMILES: O=[N+]([O-])/C=C/c1ccc(COc2ccccn2)cc1]

A mixture of 4-(pyridin-2-yloxymethyl)-benzaldehyde (26.8 g, 126 mmol)) described in Manufacturing Example 1-2-2, nitromethane (34 mL, 630 mmol), ammonium acetate (19 g, 252 mmol), and acetic acid (90 mL) was stirred for 1 hour and 30 minutes at 100° C. Ethyl acetate and water were added thereto, which was separated. The organic layer was washed with water five times and saturated sodium bicarbonate water once, dried over anhydrous magnesium sulfate, and filtered. This filtrate was concentrated under a reduced pressure, so as to obtain a crude product of the title compound (31 g).

Manufacturing Example 1-2-4

2-(4-(2-Nitro-ethyl)-benzyloxy)-pyridine

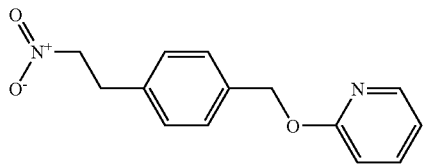

To a dimethyl sulfoxide solution (150 mL) of acetic acid (7.4 mL) and 2-(4-((E)-2-nitro-vinyl)-benzyloxy)-pyridine (30.8 g, 120 mmol)) described in Manufacturing Example 1-2-3 was added sodium borohydride (2.45 g, 64.8 mmol) at 30° C. or lower. The reaction solution was stirred for 40 minutes at room temperature. Water, ethyl acetate, and diethyl ether were added at 30° C. or lower to the reaction solution, to separate the reaction solution into water and an organic layer. The aqueous layer was extracted with ethyl acetate. The previously obtained organic layer and the ethyl acetate layer obtained this time were combined, washed with water three times and saline once, dried over anhydrous magnesium sulfate, and filtered. This filtrate was concentrated under a reduced pressure. The residue was purified by NH silica gel column chromatography (ethyl acetate:heptane=1:4) to obtain the title compound (15.2 g).

Manufacturing Example 1-2-5

4-(Pyridin-2-yloxymethyl)-phenyl-acetohydroxymoyl chloride

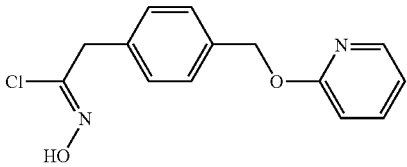 [SMILES: O/N=C(\Cl)Cc1ccc(COc2ccccn2)cc1]

To a methanol solution (80 mL) of 2-(4-(2-nitro-ethyl)-benzyloxy)-pyridine (15.2 g, 59 mmol)) described in Manufacturing Example 1-24 was added lithium methoxide (4.49 g, 118 mmol), which was stirred for 3 minutes. The reaction solution was concentrated under a reduced pressure. Toluene was added to the residue, and the solvent was concentrated under a reduced pressure. A solution of methylene chloride (100 mL) and tetrahydrofuran (50 mL) of the residue thus obtained was cooled to −66° C., and titanium(IV) chloride (20.8 mL, 189 mmol) was added thereto while stirring. The reaction solution was stirred for 10 minutes at 0° C., and then stirred for 30 minutes at room temperature. The reaction solution was poured into an ice water and stirred for 30 minutes at room temperature. Ethyl acetate and diethyl ether were added to the reaction solution, which was separated. The organic layer was washed with water three times and saline once. The aqueous layers were combined, and extracted with ethyl acetate twice. The ethyl acetate layers were combined and washed with water three times and saline once. The previously obtained organic layer and the ethyl acetate layer obtained this time were combined, dried over anhydrous magnesium sulfate and sodium sulfate, and filtered. This filtrate was concentrated under a reduced pressure, so as to obtain a crude product of the title compound (11.5 g).

The title compound of Reference Example 1 can also be synthesized by the following other methods 1 to 3.

Other Method 1 of Reference Example 1

3-(3-(4-(Pyridin-2-yloxymethyl)-benzyl)-isoxazol-5-yl)-pyridin-2-ylamine

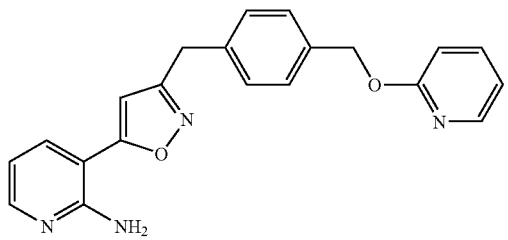 [SMILES: Nc1ncccc1-c1cc(Cc2ccc(COc3ccccn3)cc2)no1]

To a mixture of zinc chloride (8.82 g) and tetrahydrofuran (130 mL) were added 3-ethynyl-pyridin-2-ylamine (3.00 g, 98% purity) described in Manufacturing Example 1-2-3 of International Publication WO 07/052,615 and 4-(pyridin-2-yloxymethyl)-phenyl-acetohydroxymoyl chloride (17.4 g, 94% purity) described in Manufacturing Example 1-2-5 at 0° C. The reaction mixture was warmed to room temperature, and triethylamine (9.02 mL) was added dropwise while maintaining the internal temperature to 28° C. or lower by using a water bath. The reaction mixture was stirred for 20 minutes at room temperature, and then stirred for 1 hour at 35° C. The reaction mixture was brought to room temperature, an ammonium chloride aqueous solution and ethyl acetate were added to the reaction mixture, and then an ammonia aqueous solution was added to adjust the pH to approximately 8, and extraction was performed. The organic layer was washed with saturated saline and dried over anhydrous magnesium sulfate, and the solvent was evaporated under a reduced pressure. The residue was purified by NH silica gel column chromatography (heptane:ethyl acetate=3:2), then crystallization was performed using a mixed solvent of tert-butyl methyl ether and heptane, so as to obtain the title compound (5.32 g).

$^1$H-NMR spectrum (CDCl$_3$) δ (ppm): 4.07 (2H, s), 5.37 (4H, brs), 6.25 (1H, s), 6.71 (1H, dd, J=4.8, 7.7 Hz), 6.79-6.81 (1H, m), 6.89 (1H, ddd, J=0.8, 5.0, 7.0 Hz), 7.30 (2H, d, J=7.9 Hz), 7.44 (2H, d, J=8.1 Hz), 7.58 (1H, ddd, J=2.0, 7.1, 8.4 Hz), 7.70 (1H, dd, J=1.8, 7.7 Hz), 8.14 (1H, dd, J=1.8, 4.9 Hz), 8.17-8.18 (1H, m).

In the Other Method 1 of Reference Example 1, the starting material, 4-(pyridin-2-yloxymethyl)-phenyl-acetohydroxymoyl chloride, was synthesized by the following method.

Manufacturing Example 1-3-1

Methyl 3-(4-(pyridin-2-yloxymethyl)-phenyl)-oxiran-2-carboxylate

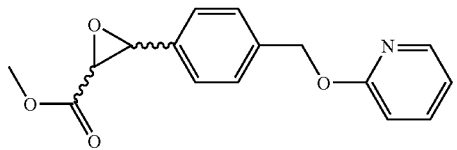 [SMILES: COC(=O)C1OC1c1ccc(COc2ccccn2)cc1]

To a mixture of 4-(pyridin-2-yloxymethyl)-benzaldehyde (24.8 g) described in Manufacturing Example 1-1-2 and tetrahydrofuran (160 mL) was added methyl chloroacetate (10.2 mL) at −15° C., and then sodium methoxide (23.7 mL, 28% methanol solution) was added thereto at the same temperature. The reaction mixture was stirred for 1 hour at 0° C., and then stirred for 2 hours at room temperature. The reaction mixture was added to 800 mL of an ice water containing acetic acid (6 mL), and the reaction mixture was warmed to room temperature. Ethyl acetate was added to the reaction mixture for extraction, and then the organic layer was separated, washed with saturated saline, and dried over anhydrous magnesium sulfate. The solvent was evaporated under a reduced pressure to obtain the title compound (30.2 g).

$^1$H-NMR spectrum (CDCl$_3$) δ (ppm): 3.51 (1H, d, J=1.8 Hz), 3.83 (3H, s), 4.11 (1H, d, J=1.8 Hz), 5.38 (2H, s), 6.81 (1H, td, J=0.9, 8.4 Hz), 6.89 (1H, ddd, J=0.9, 5.1, 7.1 Hz), 7.29-7.31 (2H, m), 7.47 (2H, d, J=8.2 Hz), 7.59 (1H, ddd, J=2.0, 7.1, 8.4 Hz), 8.17 (1H, ddd, J=0.8, 2.0, 5.1 Hz).

Manufacturing Example 1-3-2

Sodium 3-(4-(pyridin-2-yloxymethyl)-phenyl)-oxiran-2-carboxylate

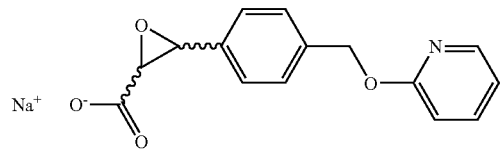 [SMILES: [Na+] ; O=C([O-])C1OC1c1ccc(COc2ccccn2)cc1]

To a mixture of methyl 3-(4-(pyridin-2-yloxymethyl)-phenyl)-oxiran-2-carboxylate (19.9 g) described in Manufacturing Example 1-3-1 and ethanol (300 mL) were added sodium methoxide (14.2 mL, 28% methanol solution), water (1.3 mL), and tetrahydrofuran (100 mL) in that order at 0° C., which was stirred for 1 hour at room temperature. Diethyl ether (200 mL) was added to the reaction mixture, and the precipitated solids were collected by filtration, so as to obtain the title compound (14.3 g).

$^1$H-NMR spectrum (CD$_3$OD) δ (ppm): 3.31 (1H, d, J=1.8 Hz), 3.88 (1H, d, J=1.8 Hz), 5.33 (2H, s), 6.84 (1H, td, J=0.9, 8.2 Hz), 6.94 (1H, ddd, J=0.9, 5.1, 7.1 Hz), 7.29-7.31 (2H, m), 7.42 (2H, d, J=8.2 Hz), 7.68 (1H, ddd, J=2.0, 7.1, 8.4 Hz), 8.12 (1H, ddd, J=0.7, 2.0, 5.1 Hz).

Manufacturing Example 1-3-3

4-(Pyridin-2-yloxymethyl)-phenyl-acetaldehyde

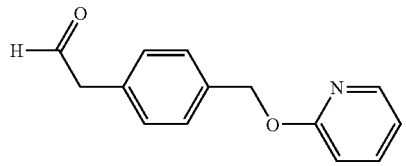 [SMILES: O=CCc1ccc(COc2ccccn2)cc1]

A mixture of sodium 3-(4-(pyridin-2-yloxymethyl)-phenyl)-oxiran-2-carboxylate (9.95 g) described in Manufacturing Example 1-3-2, toluene (200 mL), water (120 mL), and acetic acid (16 mL) was stirred for 90 minutes at 73° C. The reaction mixture was cooled to room temperature, ethyl acetate was added to the reaction mixture for extraction, and the organic layer was separated, washed with saturated saline, and dried over anhydrous magnesium sulfate. The solvent was evaporated under a reduced pressure to obtain the title compound (6.82 g).

¹H-NMR spectrum (CDCl₃) δ (ppm): 3.70 (2H, d, J=2.2 Hz), 5.38 (2H, s), 6.81 (1H, td, J=0.8, 8.2 Hz), 6.89 (1H, ddd, J=0.9, 5.1, 7.1 Hz), 7.24 (2H, d, J=8.1), 7.48 (2H, d, J=8.1 Hz), 7.59 (1H, ddd, J=2.0, 7.1, 8.4 Hz), 8.18 (1H, ddd, J=0.6, 2.0, 5.0 Hz), 9.75 (1H, t, J=2.4).

Manufacturing Example 1-3-4

4-(Pyridin-2-yloxymethyl)-phenyl-acetaldehyde oxime (E/Z mixture)

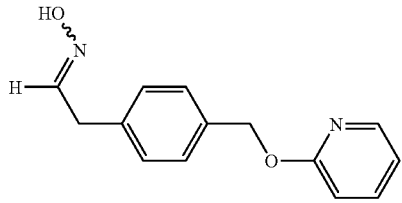 [SMILES: ON=CCc1ccc(COc2ccccn2)cc1]

To a mixture of hydroxylamine sulfate (19.7 g) and water (250 mL) was added a 1N aqueous sodium hydroxide (240 mL) at 0° C., which was stirred for 15 minutes at the same temperature. To the reaction mixture was then added a mixture of 4-(pyridin-2-yloxymethyl)-phenyl)-acetaldehyde (27.3 g) described in Manufacturing Example 1-3-3 and methanol (250 mL) dropwise, which was stirred overnight at room temperature. The precipitated solids were collected by filtration, so as to obtain the title compound (20.3 g) as a mixture of E and Z isomers.

¹H-NMR spectrum (CDCl₃) δ (ppm): 3.54 (2H, d, J=6.2 Hz), 3.74 (2H, d, J=5.3 Hz), 5.36 (2H+2H, s), 6.79-6.81 (1H+1H, m), 6.87-6.90 (1H+2H, m), 7.22-7.24 (2H+2H, m), 7.42-7.44 (2H+2H, m), 7.53 (1H, t, J=6.3 Hz), 7.56-7.61 (1H+1H, m), 8.17-8.18 (1H+1H, m) (underbar=E or Z).

Manufacturing Example 1-3-5

4-(Pyridin-2-yloxymethyl)-phenyl-acetohydroxymoyl chloride

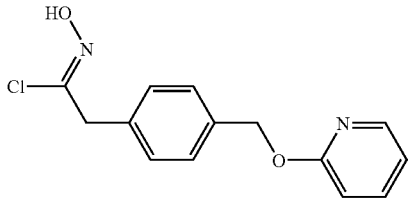 [SMILES: O/N=C(\Cl)Cc1ccc(COc2ccccn2)cc1]

To a mixture of 4-(pyridin-2-yloxymethyl)-phenyl-acetaldehyde oxime (E/Z mixture) (132 mg) described in Manufacturing Example 1-3-4 and N,N-dimethylformamide (2 mL) was added N-chlorosuccinimide (72.8 mg) at room temperature. Hydrochloric acid gas was then blown into the reaction mixture at the same temperature, which was stirred for 90 minutes at the same temperature. Ethyl acetate and water were added to the reaction mixture for extraction, and then the organic layer was separated, washed with saturated saline, and dried over anhydrous magnesium sulfate. The solvent was evaporated under a reduced pressure, and the resulting residue was washed with a mixed solvent of diethyl ether and heptane, so as to obtain the title compound (123 mg).

¹H-NMR spectrum (CDCl₃) δ (ppm): 3.81 (2H, s), 5.36 (2H, s), 6.81 (1H, d, J=8.2 Hz), 6.88-6.91 (1H, m), 7.28 (2H, d, J=8.1), 7.43 (2H, d, J=8.1 Hz), 7.57-7.62 (1H, m), 8.17-8.19 (1H, m).

Other Method 2 of Reference Example 1

3-(3-(4-(Pyridin-2-yloxymethyl)-benzyl)-isoxazol-5-yl)-pyridin-2-ylamine

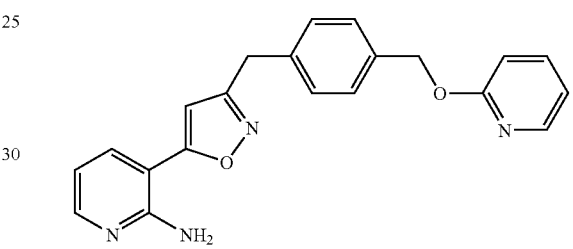

To a dichloromethane solution (120 mL) of di-tert-butyl (3-(3-(4-((pyridin-2-yloxy)methyl)benzyl)isoxazol-5-yl)pyridin-2-yl)imide dicarbonate (11.8 g, approximately 70% purity) described in Manufacturing Example 1-4-2 was added trifluoroacetic acid (40 mL) at 0° C., which was stirred for 14 hours at room temperature. Saturated sodium bicarbonate water was added at 20° C. or lower to the reaction solution, extraction was performed with ethyl acetate, and then this product was purified by NH silica gel column chromatography (heptane:ethyl acetate=1:1). The solvent was concentrated under a reduced pressure and to the resulting residue was added tert-butyl methyl ether, followed by filtering solids, and the title compound (7.29 g) was obtained.

¹H-NMR spectrum (DMSO-d₆) δ (ppm): 4.04 (2H, s), 5.32 (2H, s), 6.26 (2H, brs), 6.69 (1H, dd, J=4.8, 8.0 Hz), 6.81 (1H, s), 6.83-6.87 (1H, m), 6.97-7.00 (1H, m), 7.33 (2H, d, J=8.0 Hz), 7.40 (2H, d, J=8.0 Hz), 7.69-7.74 (1H, m), 7.87 (1H, dd, J=2.0, 7.6 Hz), 8.08 (1H, dd, J=2.0, 7.6 Hz), 8.15-8.17 (1H, m).

The starting material, di-tert-butyl (3-(3-(4-((pyridin-2-yloxy)methyl)benzyl)isoxazol-5-yl)pyridin-2-yl)imide dicarbonate was synthesized by the following method. Manufacturing Example 1-4-1: Di-tert-butyl (3-ethynylpyridin-2-yl)imide dicarbonate

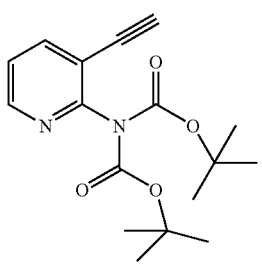 [SMILES: C#Cc1cccnc1N(C(=O)OC(C)(C)C)C(=O)OC(C)(C)C]

3-Ethynyl-pyridin-2-ylamine (6.34 g) described in Manufacturing Example 1-2-3 of International Publication WO 07/052,615, di-tert-butyl dicarbonate (58.5 g), triethylamine (27.1 g), 4-dimethylaminopyridine (655 mg), and tetrahydrofuran (254 mL) were stirred for 18 hours at room temperature. Silica gel was added to the reaction solution, and the solvent was concentrated under a reduced pressure. The silica gel thus obtained was purified by silica gel chromatography (heptane:ethyl acetate=3:1) to obtain the title compound (15 g) as a white solid.

$^1$H-NMR spectrum (DMSO-$d_6$) δ (ppm): 1.32 (18H, s), 4.59 (1H, s), 7.39-7.44 (1H, m), 7.99-8.03 (1H, m), 8.46-8.48 (1H, m).

Manufacturing Example 1-4-2

Di-tert-butyl (3-(3-(4-((pyridin-2-yloxy)methyl)benzyl)isoxazol-5-yl)pyridin-2-yl)imide dicarbonate

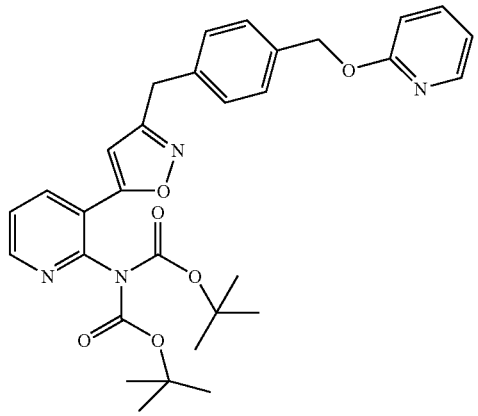 [SMILES: CC(C)(C)OC(=O)N(C(=O)OC(C)(C)C)c1ncccc1-c1cc(Cc2ccc(COc3ccccn3)cc2)no1]

To a tetrahydrofuran solution (200 mL) of di-tert-butyl (3-ethynylpyridin-2-yl)imide dicarbonate (12 g) described in Manufacturing Example 1-4-1,2-(4-(2-nitro-ethyl)-benzyloxy)-pyridine (19.4 g) described in Manufacturing Example 1-1-4, and 4-dimethylaminopyridine (230 mg) was added di-tert-butyl dicarbonate (28.8 g) over a period of 8 hours and in four batches, at room temperature while stirring. Upon completion of the addition, the reaction mixture was stirred for another 22 hours at room temperature. Silica gel was added to the reaction solution and the solvent was concentrated under a reduced pressure. The silica gel thus obtained was purified by silica gel chromatography (heptane:ethyl acetate=3:1, and then 2:1) to obtain an oily substance (11.8 g containing approximately 70% the target substance) containing the title compound.

Di-tert-butyl (3-(3-(4-((pyridin-2-yloxy)methyl)benzyl)isoxazol-5-yl)pyridin-2-yl)imide dicarbonate of Manufacturing Example 1-4-2 can also be synthesized by the following Other Method 1 or 2.

Manufacturing Example 1-5-1

Di-tert-butyl (3-(3-(4-((pyridin-2-yloxy)methyl)benzyl)isoxazol-5-yl)pyridin-2-yl)imide dicarbonate (Other Method 1 of Manufacturing Example 1-4-2)

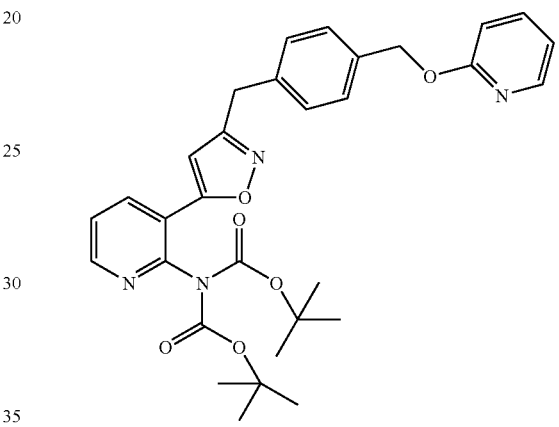

To a tetrahydrofuran solution (20 mL) of di-tert-butyl(3-ethynylpyridin-2-yl)imide dicarbonate (2.0 g) described in Manufacturing Example 1-4-1,2-(4-(2-nitro-ethyl)-benzyloxy)-pyridine (2.44 g) described in Manufacturing Example 1-14, and triethylamine (0.086 μL) was added phenyl isocyanate (2.8 mL) over a period of 5.5 hours and in four batches, at 50° C. while stirring. Upon completion of the addition, the reaction mixture was stirred for another 2 hours at 50° C. NH-silica gel was added to the reaction solution and the solvent was concentrated under a reduced pressure. The NH-silica gel thus obtained was purified by NH-silica gel chromatography (heptane:ethyl acetate=3:1). The solution thus obtained was concentrated under a reduced pressure and purified by silica gel chromatography (heptane:ethyl acetate=3:1, and then 2:1) to obtain the title compound (2.2 g) as an oily substance.

$^1$H-NMR spectrum (DMSO-$d_6$) δ (ppm): 1.18 (18H, s), 4.07 (2H, s), 5.32 (2H, s), 6.58 (1H, s), 6.83-6.86 (1H, m), 6.96-7.01 (1H, m), 7.29 (2H, d, J=8.0 Hz), 7.40 (2H, d, J=8.0 Hz), 7.58 (1H, dd, J=4.8, 7.6 Hz), 7.69-7.74 (1H, m), 8.15-8.18 (1H, m), 8.34 (1H, dd, J=2.0, 7.6 Hz), 8.59 (1H, dd, J=2.0, 5.2 Hz).

Manufacturing Example 1-6-1

Di-tert-butyl (3-(3-(4-((pyridin-2-yloxy)methyl)benzyl)isoxazol-5-yl)pyridin-2-yl)imide dicarbonate
(Other Method 2 of Manufacturing Example 1-4-2)

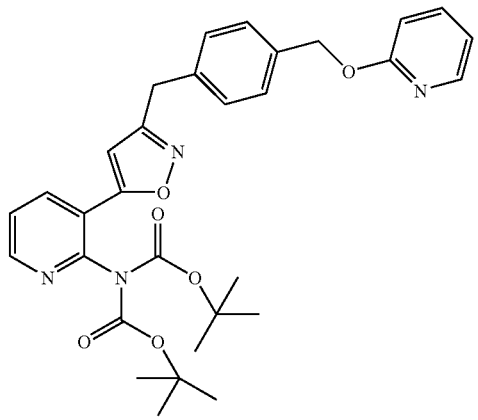 [SMILES: CC(C)(C)OC(=O)N(C(=O)OC(C)(C)C)c1ncccc1-c1cc(Cc2ccc(COc3ccccn3)cc2)no1]

4-Methylen-2-oxo-4H-pyrido[2,3-d][1,3]oxazin-1-carboxylic acid tert-butyl ester (1.48 g) described in Manufacturing Example 1-6-2,2-(4-(2-nitro-ethyl)-benzyloxy)-pyridine (2.9 g) described in Manufacturing Example 1-1-4, di-tert-butyl dicarbonate (6.14 g), 4-dimethylaminopyridine (68.6 mg), and tetrahydrofuran (50 mL) were stirred for 2 hours at room temperature. Silica gel was added to the reaction solution, and the solvent was concentrated under a reduced pressure. The silica gel thus obtained was purified by silica gel chromatography (heptane:ethyl acetate=3:1, then 1:1, and then 1:2) to obtain the title compound (2.1 g) as an oily substance.
$^1$H-NMR spectrum (DMSO-$d_6$) δ (ppm): 1.18 (18H, s), 4.07 (2H, s), 5.32 (2H, s), 6.58 (1H, s), 6.83-6.86 (1H, m), 6.96-7.01 (1H, m), 7.29 (2H, d, J=8.0 Hz), 7.40 (2H, d, J=8.0 Hz), 7.58 (1H, dd, J=4.8, 7.6 Hz), 7.69-7.74 (1H, m), 8.15-8.18 (1H, m), 8.34 (1H, dd, J=2.0, 7.6 Hz), 8.59 (1H, dd, J=2.0, 5.2 Hz).

The starting material, 4-methylen-2-oxo-4H-pyrido[2,3-d][1,3]oxazin-1-carboxylic acid tert-butyl ester, was synthesized by the following method.

Manufacturing Example 1-6-2

4-Methylen-2-oxo-4H-pyrido[2,3-d][1,3]oxazin-1-carboxylic acid tert-butyl ester

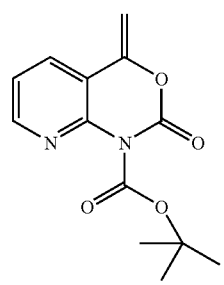 [SMILES: C=C1OC(=O)N(C(=O)OC(C)(C)C)c2ncccc21]

1-(2-Amino-pyridin-3-yl)-ethanone (990 mg), di-tert-butyl dicarbonate (7.92 g), 4-dimethylaminopyridine (88.8 mg), triethylamine (4.95 mL), and tetrahydrofuran (16.5 mL) were stirred for 24 hours at room temperature. Silica gel was added to the reaction solution, and the solvent was concentrated under a reduced pressure. The silica gel thus obtained was purified by silica gel chromatography (heptane:ethyl acetate=2:1) to obtain the title compound (1.48 g) as an oily substance.
$^1$H-NMR spectrum (DMSO-$d_6$) δ (ppm): 1.56 (9H, s), 5.01 (1H, d, J=3.6 Hz), 5.45 (1H, d, J=3.6 Hz), 7.28 (1H, dd, J=4.8, 8.0 Hz), 8.25 (1H, dd, J=1.6, 8.0 Hz), 8.36 (1H, dd, J=1.6, 4.8 Hz).

Other Method 3 of Reference Example 1

3-(3-(4-(Pyridin-2-yloxymethyl)-benzyl)-isoxazol-5-yl)-pyridin-2-ylamine

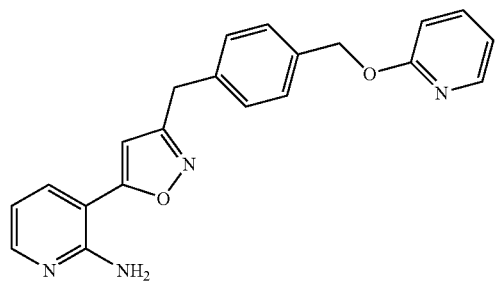 [SMILES: Nc1ncccc1-c1cc(Cc2ccc(COc3ccccn3)cc2)no1]

A mixture of 2-(4-(5-iodo-isoxazol-3-ylmethyl)-benzyloxy)-pyridine (200 mg) described in Manufacturing Example 1-8-2,2-N-butoxycarbonyl-3-pyridineboronic acid (134 mg) described in Manufacturing Example 1-7-2, sodium carbonate (82 mg), tetrakis(triphenylphosphine) palladium (59 mg), 1,2-dimethoxyethane (6 mL), and water (1 mL) was stirred under a nitrogen atmosphere for 2 hours at 80° C. This mixture was cooled to room temperature, and ethyl acetate and water were added. The organic layer was separated, washed with water and saturated saline, dried over anhydrous magnesium sulfate, and then filtered. After the filtrate was adsorbed to silica gel, it was purified by silica gel column chromatography (heptane:ethyl acetate=4:1 to 1:1 to ethyl acetate) to obtain the title compound (116 mg).

The starting material, 2-N-butoxycarbonyl-3-pyridineboronic acid, was synthesized by the following method.

Manufacturing Example 1-7-1

Pyridin-2-yl-carbamic acid tert-butyl ester

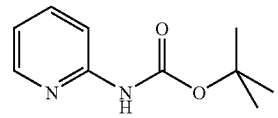

To a solution of tert-butyl alcohol (650 mL) and di-tert-butyl carbonate (24 g) was added 2-aminopyridine (9.4 g) slowly. This mixture was stirred for 24 hours at room temperature. This reaction solution was concentrated under a reduced pressure, and the residue was purified by silica gel chromatography (heptane:ethyl acetate=1:1) to obtain the title compound (18 g).

¹H-NMR spectrum (DMSO-d₆) δ (ppm): 1.47 (9H, s), 6.99-7.03 (1H, m), 7.70-7.74 (1H, m), 7.77-7.80 (1H, m), 8.23-8.24 (1H, m), 9.72 (1H, brs).

Manufacturing Example 1-7-2

2-N-butoxycarbonyl-3-pyridineboronic acid

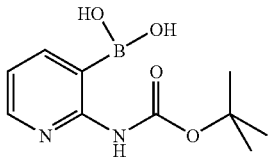 [SMILES: CC(C)(C)OC(=O)Nc1ncccc1B(O)O]

A tetrahydrofuran solution (400 mL) of pyridin-2-yl-carbamic acid tert-butyl ester (16 g) described in Manufacturing Example 1-7-1 and N,N,N',N'-tetramethylethylenediamine (25 g) was cooled to −70° C., n-butyl lithium (78 mL, 2.64 m heptane solution) was then added dropwise over a period of 1 hour, which was stirred for 10 minutes. This mixture was warmed to a temperature between −10° C. and −6° C., which was stirred for 2 hours at that temperature. The solution was again cooled to −70° C., and triisobutyl borate (58 g) was added dropwise over a period of 1 hour. This mixture was warmed to 0° C., and then a saturated ammonium chloride aqueous solution was added thereto. Ether was added to the yellow solid thus produced, which was stirred, and the solid was then collected by filtration and washed with ether and water. This solid was dried under a reduced pressure, so as to obtain the title compound (14 g).

¹H-NMR spectrum (DMSO-d₆) δ (ppm): 1.32-1.41 (9H, m), 6.80-6.84 (1H, m), 7.95-8.13 (2H, m).

In the Other Method 3 of Reference Example 1, the starting material, 2-(4-(5-iodo-isoxazol-3-ylmethyl)-benzyloxy)-pyridine, was synthesized by the following method.

Manufacturing Example 1-8-1

2-(4-(5-Tri-n-butylstannyl-isoxazol-3-ylmethyl)-benzyloxy)-pyridine

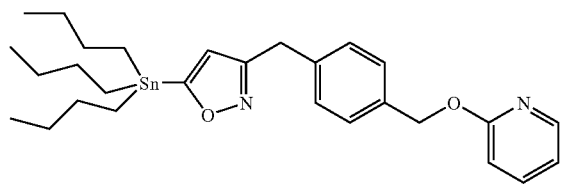 [SMILES: CCC[CH2][Sn]([CH2]CCC)([CH2]CCC)[c]1cc(Cc2ccc(COc3ccccn3)cc2)no1]

To a tetrahydrofuran solution (90 mL) of tri-n-butylethynyltin (3 g), 2-(4-(2-nitro-ethyl)-benzyloxy)-pyridine (4.9 g) described in Manufacturing Example 1-1-4, and 4-dimethylaminopyridine (116 mg) was added a tetrahydrofuran solution (30 mL) of di-tert-butyl dicarbonate (7.3 g), which was stirred for 15 hours at room temperature. Ethyl acetate and water were added to this mixture. The organic layer was separated, washed with water and saturated saline, dried over anhydrous magnesium sulfate, and filtered. The filtrate was adsorbed to silica gel, and then purified by silica gel column chromatography (heptane:ethyl acetate=4:1) to obtain the title compound (5.3 g).

¹H-NMR spectrum (DMSO-d₆) δ (ppm): 0.81-0.85 (9H, m), 1.08-1.12 (6H, m), 1.23-1.30 (6H, m), 1.46-1.54 (6H, m), 4.00 (2H, s), 5.30 (2H, s), 6.40 (1H, s), 6.83-6.86 (1H, m), 6.97-7.00 (1H, m), 7.25-7.26 (2H, m), 7.36-7.38 (2H, m), 7.69-7.74 (1H, m), 8.15-8.17 (1H, m).

Manufacturing Example 1-8-2

2-(4-(5-Iodo-isoxazol-3-ylmethyl)-benzyloxy)-pyridine

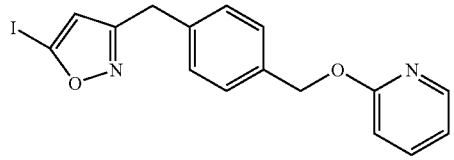 [SMILES: Ic1cc(Cc2ccc(COc3ccccn3)cc2)no1]

To a tetrahydrofuran solution (15 mL) of 2-(4-(5-tri-n-butylstannyl-isoxazol-3-ylmethyl)-benzyloxy)-pyridine (5.1 g) described in Manufacturing Example 1-8-1 was added iodine (2.5 g) at 0° C. This mixture was stirred at this temperature for 20 minutes. A 10% sodium thiosulfate aqueous solution and ethyl acetate were added to this mixture. The organic layer was separated, washed with saturated saline, dried over anhydrous magnesium sulfate, and then filtered. The filtrate was concentrated, and the residue was purified by silica gel column chromatography (heptane:ethyl acetate=10:1 to 4:1) to obtain the title compound (2.4 g).

¹H-NMR spectrum (DMSO-d₆) δ (ppm): 3.99 (2H, s), 5.31 (2H, s), 6.66 (1H, s), 6.84-6.87 (1H, m), 6.97-7.00 (1H, m), 7.26 (2H, d, J=8 Hz), 7.39 (2H, d, J=8 Hz), 7.70-7.74 (1H, m), 8.16-8.17 (1H, m).

Another method for the manufacturing example of 3-(3-(4-(pyridin-2-yloxymethyl)-benzyl)-isoxazol-5-yl)-pyridin-2-ylamine described in Reference Example 1 will now be described.

Reference Example 2

Synthesis of tert-butyl (3-acetylpyridin-2-yl)carbamate

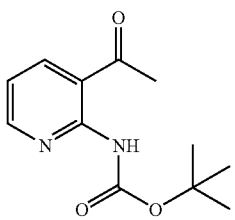 [SMILES: CC(=O)c1cccnc1NC(=O)OC(C)(C)C]

A mixture of 1-(2-aminopyridin-3-yl)ethanone (50 g, 368 mmol), di-tert-butyldicarbonate (120 g, 552 mmol) and tert-butanol (200 mL) was stirred at 90° C. for three hours under a nitrogen atmosphere. After cooling, the solvent was evaporated under a reduced pressure, n-heptane (500 mL) was added to the residue and the precipitated solid was filtered to obtain the title compound (77 g) as a yellow solid.

$^1$H-NMR Spectrum (CDCl$_3$) δ (ppm): 1.54 (9H, s), 2.64 (3H, s), 7.03 (1H, dd, J=4.8, 8.0 Hz), 8.16 (1H, dd, J=2.0, 8.0 Hz), 8.63 (1H, dd, J=2.0, 4.8 Hz), 10.82 (1H, brs).

Reference Example 3

Synthesis of ethyl 5-(2-aminopyridin-3-yl)isoxazol-3-carboxylate

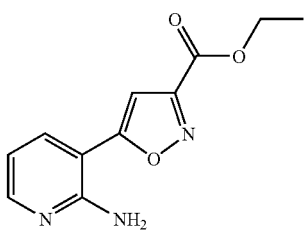 [SMILES: CCOC(=O)c1cc(-c2cccnc2N)on1]

To a solution of tert-butyl (3-acetyl pyridin-2-yl)carbamate (600 mg, 2.29 mmol) and diethyl oxalate (669 mg, 4.58 mmol) in toluene (5.0 mL) was added potassium tert-butoxide (514 mg, 4.58 mmol) at room temperature under a nitrogen atmosphere, which was stirred for two hours. After addition of toluene (5.0 mL) and stirring for one hour, potassium tert-butoxide (257 mg, 2.29 mmol) was added thereto and the solution was stirred for two hours. To the reaction mixture were added hydroxylamine hydrochloride (477 mg, 6.87 mmol) and ethanol (10 mL), which was stirred for one hour, water (1.0 mL) was added thereto and the solution was stirred overnight at room temperature. Water (30 mL) was added thereto and the solution was extracted with ethyl acetate. After the organic layer was washed with saturated sodium chloride water and dried over anhydrous magnesium sulfate, the solution was concentrated. The concentrated residue was dissolved in N,N-dimethyl formamide (5 mL), triethylamine (192 mg) was added thereto, and the solution was stirred at 80° C. for six hours. After cooling, water was added thereto, and the solution was extracted with ethyl acetate. After the organic layer was washed with saturated sodium chloride water and dried over anhydrous magnesium sulfate, the solvent was evaporated under a reduced pressure to obtain the title compound (443 mg) as a white solid.

$^1$H-NMR Spectrum (CDCl$_3$) δ (ppm): 1.45 (3H, t, J=7.2 Hz), 4.49 (2H, q, J=7.2 Hz), 5.40 (2H, brs), 6.79 (1H, dd, J=5.2, 7.6 Hz), 6.91 (1H, s), 7.81 (1H, dd, J=2.0, 7.6 Hz), 8.21 (1H, dd, J=2.0, 5.2 Hz).

Reference Example 4

Synthesis of [5-(2-aminopyridin-3-yl)isoxazol-3-yl]methanol

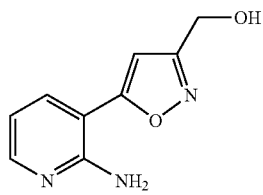 [SMILES: Nc1ncccc1-c1cc(CO)no1]

To a suspension of ethyl 5-(2-aminopyridin-3-yl)isoxazol-3-carboxylate (381 mg, 1.63 mmol) in tetrahydrofuran (3.8 mL) and ethanol (3.8 mL) was added sodium borohydride (201 mg, 4.89 mmol) at 0° C. under a nitrogen atmosphere, which was stirred at 0° C. for one hour and at 20° C. for 21 hours. Under an ice water bath cooling, to the reaction mixture was added 2N hydrochloric acid (2.46 mL, 4.89 mmol) dropwise, which was stirred at 0° C. for 10 minutes and at room temperature for 30 minutes. Under the ice water bath cooling, after an aqueous solution of 5% sodium bicarbonate was added dropwise to adjust basic, the solution was extracted with ethyl acetate. After the organic layer was dried over anhydrous magnesium sulfate, the solvent was evaporated under a reduced pressure. The residue was suspended in tetrahydrofuran (1.4 mL), to the reaction mixture was added sodium borohydride (67 mg, 1.63 mmol) at 0° C., which was washed thereto down with methanol (1.4 mL). After stirring at room temperature for one hour, the solution was stirred at 60° C. for five hours. Under an ice water bath cooling, to the reaction mixture was added 1N hydrochloric acid (1.63 mL, 1.63 mmol) dropwise, which was stirred at 0° C. for 10 minutes and at room temperature for 30 minutes. Under the ice water bath cooling, after adding 1N aqueous sodium hydroxide dropwise to adjust basic, the solution was extracted with ethyl acetate. After the organic layer was dried over anhydrous magnesium sulfate, the solvent was evaporated under a reduced pressure to obtain the title compound (258 mg) as a pale yellow solid.

$^1$H-NMR Spectrum (DMSO-d$_6$) δ (ppm): 4.56 (2H, d, J=5.6 Hz), 5.54 (1H, t, J=5.6 Hz), 6.27 (2H, brs), 6.72 (1H, dd, J=4.8, 7.6 Hz), 6.90 (1H, s), 7.90 (1H, dd, J=2.0, 7.6 Hz), 8.10 (1H, dd, J=2.0, 4.8 Hz).

Reference Examples 5 to 10 are other synthesis methods to Reference Examples 3 and 4.

Reference Example 5

Synthesis of N-(3-acetylpyridin-2-yl)-2,2-dimethylpropanamide

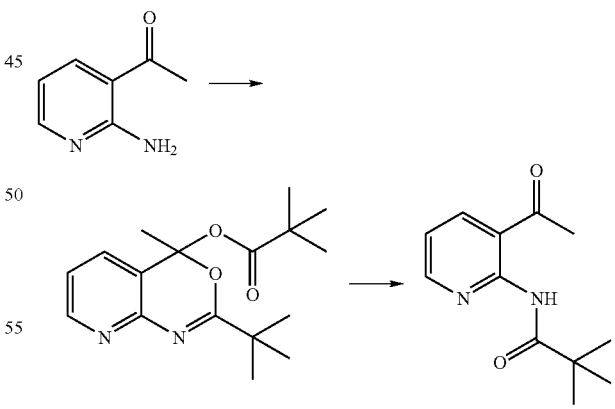

To a mixture of 1-(2-aminopyridin-3-yl)ethanone (272 mg, 2 mmol), 4-dimethylaminopyridine (24 mg, 0.2 mmol), triethylamine (0.64 mL, 4.6 mmol) and toluene (2 mL) was added pivaloyl chloride (0.52 mL, 4.2 mmol) dropwise at room temperature, which was stirred at room temperature for one hour and at 60° C. for five hours. After formation of 2-tert-butyl-4-methyl-4H-pyrido[2,3-d][1,3]oxazin-4-yl pivalate was confirmed, to the reaction mixture were added water (2 mL) and 5N hydrochloric acid (0.8 mL), which was stirred at room temperature for 30 minutes. After the reaction mixture was separated, to the aqueous layer was added 5N aqueous sodium hydroxide (1 mL) and extracted with toluene. The solvent was evaporated under a reduced pressure and the precipitated solid was filtered to obtain the title compound (415 mg).

$^1$H-NMR Spectrum (CDCl$_3$) δ (ppm): 1.33 (9H, s), 2.64 (3H, s), 7.10 (1H, dd, J=4.8, 8.0 Hz), 8.17 (1H, dd, J=2.0, 7.6 Hz), 8.64 (1H, dd, J=2.0, 4.8 Hz).

2-tert-butyl-4-methyl-4H-pyrido[2,3-d][1,3]oxazin-4-yl pivalate $^1$H-NMR Spectrum (CDCl$_3$) δ (ppm): 1.09 (9H, s), 1.32 (9H, s), 2.05 (3H, s), 7.14 (1H, dd, J=4.8, 7.6 Hz), 7.71 (1H, dd, J=2.0, 7.6 Hz), 8.51 (1H, dd, J=2.0, 4.8 Hz).

Reference Examples 6 to 7 are other synthesis methods to Reference Example 5.

Reference Example 6

Synthesis of 2-tert-butyl-4H-pyrido[2,3-d][1,3]oxazin-4-one

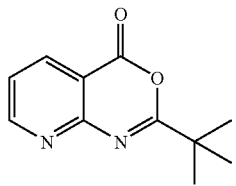

To a mixture of 2-aminonicotinic acid (13.8 g, 100 mmol), 4-dimethylaminopyridine (1.2 g, 10 mmol), triethylamine (55.8 mL, 400 mmol) and N-methylpyrrolidone (140 mL, 42 mmol) was added pivaloyl chloride (24.1 g, 200 mmol) dropwise at 0° C., and after the drop wise addition was finished, which was stirred overnight at room temperature. To the reaction mixture was added water, extracted with toluene, and the organic layer was washed with water and saturated sodium chloride water. After the solution was dried over anhydrous magnesium sulfate and filtered, the solvent was evaporated under a reduced pressure. To the residue was added n-heptane, which was suspended and stirred at 0° C., which was filtered to obtain the title compound (16.6 g).

$^1$H-NMR Spectrum (CDCl$_3$) δ (ppm): 1.45 (9H, s), 7.48 (1H, dd, J=4.8, 8.0 Hz), 8.52 (1H, dd, J=2.0, 7.6 Hz), 8.97 (1H, dd, J=2.0, 4.8 Hz).

Reference Example 7

Synthesis of N-(3-acetylpyridin-2-yl)-2,2-dimethylpropanamide

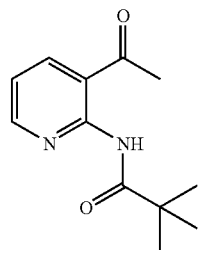 [SMILES: CC(=O)c1cccnc1NC(=O)C(C)(C)C]

To a mixture of 2-tert-butyl-4H-pyrido[2,3-d][1,3]oxazin-4-one (10.2 g, 50 mmol) and tetrahydrofuran (50 mL) was added methyl magnesium bromide (0.97 m tetrahydrofuran solution, 100 mL, 97 mmol) dropwise at −78° C., after the dropwise addition was finished, which was stirred at −78° C. for 30 minutes. To the reaction mixture were added a saturated aqueous solution of ammonium chloride and water, which was extracted with ethyl acetate, and the organic layer was washed with an aqueous solution of ammonium chloride. The solvent was evaporated under a reduced pressure and the precipitated solid was filtered to obtain the title compound (9.1 g)

$^1$H-NMR Spectrum (CDCl$_3$) δ (ppm): 1.33 (9H, s), 2.64 (3H, s), 7.10 (1H, dd, J=4.8, 8.0 Hz), 8.17 (1H, dd, J=2.0, 7.6 Hz), 8.64 (1H, dd, J=2.0, 4.8 Hz).

Reference Example 8

Synthesis of ethyl 5-{2-[(2,2-dimethylpropanoyl)amino]pyridin-3-yl}isoxazol-3-carboxylate

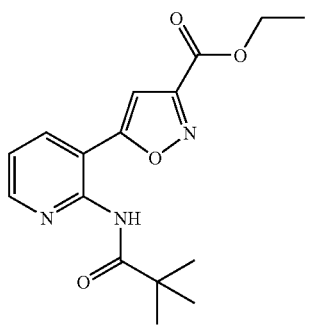 [SMILES: CCOC(=O)c1cc(-c2cccnc2NC(=O)C(C)(C)C)on1]

To a mixture of N-(3-acetyl pyridin-2-yl)-2,2-dimethyl-propanamide (8.08 g, 36.7 mmol), diethyl oxalate (10.0 mL, 73.4 mmol) and ethanol (36 mL) was added potassium tert-butoxide (8.23 g, 73.4 mmol) at −25° C., which was stirred at −25° C. for one hour. The reaction mixture was added water (72 mL), which was stirred at room temperature, toluene (36 mL) was added, separated, and the obtained aqueous layer was further washed with toluene (36 mL). To the solution were added 5N hydrochloric acid (14 mL) and hydroxylamine hydrochloride (5.10 g, 73.4 mmol), which was stirred at room temperature for 30 minutes. To the reaction mixture was added 5N aqueous sodium hydroxide (14 mL), which was extracted with toluene, the solvent was evaporated under a reduced pressure. To the obtained residue were added ethanol (35 mL) and triethylamine (5 mL), which was stirred at 80° C. to 85° C. for six hours. To the reaction mixture was added n-heptane (105 mL) and the precipitated solid was filtered to obtain the title compound (6.90 g).

$^1$H-NMR Spectrum (DMSO-d$_6$) δ (ppm): 1.19 (9H, s), 1.32 (3H, t), 4.37 (4H, q), 7.12 (1H, s), 7.46 (1H, dd, J=4.8, 8.0 Hz), 8.25 (1H, dd, J=2.0, 8.0 Hz), 8.58 (1H, dd, J=2.0, 4.8 Hz), 10.03 (1H, s).

Reference Example 9

Synthesis of N-{3-[3-(hydroxymethyl)isoxazol-5-yl]pyridin-2-yl}-2,2 dimethylpropanamide

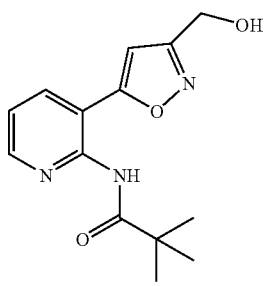 [SMILES: CC(C)(C)C(=O)Nc1ncccc1-c1cc(CO)no1]

To a mixture of ethyl 5-{2-[(2,2-dimethylpropanoyl)amino]pyridin-3-yl}isoxazol-3-carboxylate (111 g, 350 mmol), ethanol (110 mL) and tetrahydrofuran (350 mL) was added sodium borohydride (13.2 g, 350 mmol) at room temperature, which was stirred at room temperature for 6 hours. To the reaction mixture were added water (350 mL) and 5N hydrochloric acid (90 mL), which was stirred at room temperature for 30 minutes, 5N aqueous sodium hydroxide (110 mL) was added thereto, the solution was extracted with a mixture of ethyl acetate and tetrahydrofuran, and the organic layer was washed with water and saturated sodium chloride water. The solvent was evaporated under a reduced pressure to obtain the title compound (83.8 g) as a yellow solid, partially contaminated with [5-(2-aminopyridin-3-yl)isoxazol-3-yl]methanol.

$^1$H-NMR Spectrum (DMSO-$d_6$) δ (ppm): 1.20 (9H, s), 4.52 (2H, d, J=6.0 Hz), 5.53 (1H, t, J=6.0 Hz), 6.70 (1H, s), 7.44 (1H, dd, J=4.8, 8.0 Hz), 8.19 (1H, dd, J=5.6, 7.6 Hz), 8.53 (1H, dd, J=2.0, 4.8 Hz), 9.89 (1H, brs).

Reference Example 10

Synthesis of [5-(2-aminopyridin-3-yl)isoxazol-3-yl]methanol

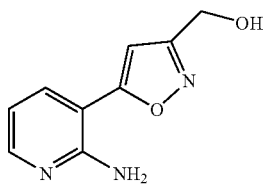

To a mixture of N-{3-[3-(hydroxymethyl)isoxazol-5-yl]pyridin-2-yl}-2,2 dimethylpropanamide (82.8 g) obtained in Reference Example 9 and methanol (350 mL) was added 5N aqueous sodium hydroxide (350 mL) at room temperature, which was stirred at 57 to 60° C. for 14 hours. To the reaction mixture was added acetic acid (100 mL) and the precipitated solid was filtered to obtain the title compound (42.2 g) as a grayish white solid.

$^1$H-NMR Spectrum (DMSO-$d_6$) δ (ppm): 4.54 (2H, s), 5.57 (1H, brs), 6.25 (2H, brs), 6.71 (1H, dd, J=4.8, 8.0 Hz), 6.90 (1H, s), 7.90 (1H, dd, J=1.6, 7.6 Hz), 8.09 (1H, dd, J=1.6, 4.8 Hz).

Reference Examples 11 to 13 are other synthesis methods to Reference Examples 5 to 10.

Reference Example 11

Synthesis of N-(3-acetylpyridin-2-yl)-2,2-dimethylpropanamide

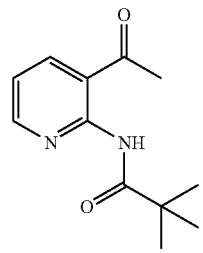 [SMILES: CC(=O)c1cccnc1NC(=O)C(C)(C)C]

After 1-(2-aminopyridin-3-yl)ethanone (40.0 kg, 294 mol) was added to a 1500 L reactor, which was washed thereto down with toluene (approximately 15 kg). Then, after toluene was added until there was 347 kg of toluene in total, pivaloyl chloride (53.1 kg, 1.5 m/M) was added thereto. Triethylamine (23.8 kg, 0.8 m/M) was added thereto dropwise at an internal temperature of 30° C. or lower and the solution was stirred at an internal temperature of from 20 to 30° C. for one hour or longer. After triethylamine (23.8 kg, 0.8 m/M) was again added dropwise at an internal temperature of 30° C. or lower, the solution was stirred at an internal temperature of from 20 to 30° C. for two hours or longer, it was confirmed by HPLC that the reaction had ended.

Under a brine cooling, water (100 L) was added dropwise at an internal temperature of 30° C. or lower, then, 35% hydrochloric acid (49.0 kg, 1.6 m/M) was added thereto dropwise at an internal temperature of 30° C. or lower. After the reaction solution was stirred for five minutes, the solution was left standing still for 15 minutes or longer and lower layer (a) was separated into a poly container. After water (100 L) was added thereto and the solution was stirred for five minutes, the solution was left standing still for 15 minutes or longer. After lower layer (c) was separated into a poly container and upper layer (d) was removed, lower layer (a) and lower layer (c) were returned into the 1500 L reactor. Under the brine cooling, ethyl acetate (289 kg) was added thereto, then, after an aqueous solution of 48.7% sodium hydroxide (43.4 kg, 1.8 m/M) was added dropwise at an internal temperature of 30° C. or lower and the solution was stirred for five minutes, it was confirmed with a UNIV test paper that a pH of the lower layer was from 8 to 9. After being left standing still for 15 minutes or longer, lower layer (e) and upper layer (f) were each separated and lower layer (e) was returned into the 1500 L reactor. After ethyl acetate (144 kg) was added thereto and the solution was stirred for five minutes, the solution was left standing still for 15 minutes or longer and lower layer (g) and upper layer (h) were each separated. After lower layer (g) was returned into the 1500 L reactor, ethyl acetate (144 kg) was added thereto and the solution was stirred for five minutes, the solution was left standing still for 15 minutes or longer. After removing lower layer (i), upper layer (f) and upper layer (h) were returned into the 1500 L reactor and which was washed thereto down with ethyl acetate (approximately 15 kg).

The organic layer returned into the 1500 L reactor was concentrated under a reduced pressure (50° C. hot water), and concentration was stopped once at the point of time when the concentrate reached approximately 200 L. The concentrate was removed into SUS containers and the inside of the reactor was washed out with toluene (17 kg). Approximately half of the amount of the removed concentrate was placed in a 300 L reactor and washed thereto down with toluene (9 kg). The concentrate was further concentrated under a reduced pressure (50° C. hot water), and when the amount of distillation from the condenser decreased, the remaining concentrate was placed in the 300 L reactor and which was washed thereto down with toluene (9 kg). Concentration under a reduced pressure was restarted (50° C. to 70° C. hot water). At the point of time when there was almost no distillation, water cooling was started and toluene (52 kg) was added thereto at an internal temperature of 50° C. or lower. Concentration under a reduced pressure was restarted (50 to 80° C. hot water). Concentration was stopped at the point of time when distillation was no longer observed at an external temperature of 80° C. and a reduced pressure level of −0.090 mPa or greater, and ethanol (61 kg) was added thereto at an internal temperature of from 20 to 30° C.

Under a nitrogen atmosphere, the ethanol solution inside the can was removed into a SUS container, and the can was washed out with ethanol (13 kg). After the removed solution was added into the 1500 L reactor, which was washed thereto down with ethanol (13 kg) to obtain an ethanol solution of the title compound (containing 69.4 kg of the target compound; yield: 107.3%).

HPLC conditions: column: YMC-Pack Pro C18 (5 μm, 150×4.6 mm I.D., YMC), mobile phase: acetonitrile/water/ammonium acetate=300/700/1 to 900/100/1 (v/v/w).

Reference Example 12

Synthesis of ethyl 5-{2-[(2,2-dimethylpropanoyl)amino]pyridin-3-yl}isoxazol-3-carboxylate

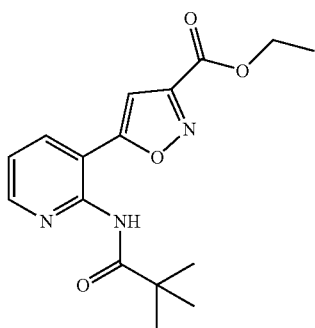 [SMILES: CCOC(=O)c1cc(-c2cccnc2NC(=O)C(C)(C)C)on1]

Under a nitrogen gas stream, diethyl oxalate (64.4 kg, 1.5 m/M) was added to the ethanol solution of N-(3-acetyl pyridin-2-yl)-2,2-dimethylpropanamide (294 mol, assuming that the yield of the previous step was 100%) in the 1500 L reactor. Brine circulation was started and a pre-cooled ethanol solution of 22% potassium tert-butoxide (212.5 kg, 1.45 m/M) was added dropwise thereto at an internal temperature of 10° C. or lower. After stirring at an internal temperature of from −5 to 10° C. for 30 minutes or longer, it was confirmed by HPLC that the reaction had ended.

Next, hydroxylamine hydrochloride (40.8 kg, 2.0 m/M) was added thereto at an internal temperature of 10° C. or lower, and the solution was stirred at an internal temperature of 10° C. or lower for one hour or longer. Next, prepared and cooled beforehand, hydrous ethanol (ethanol (15.3 kg)/water (5.2 kg)) was added dropwise thereto at an internal temperature of 20° C. or lower while watching for heating, and water (582 L) was added dropwise at an internal temperature of 30° C. or lower. Switching to hot water (28° C.) circulation, ethyl 4-{2-[(2,2-dimethylpropanoyl)amino]pyridin-3-yl}-2-(hydroxyimino)-4-oxobutanoate (approximately 10 g) was added thereto at an internal temperature of from 20 to 30° C. After confirming the precipitation of solid visually, the suspension was stirred overnight at an internal temperature of from 15 to 25° C. After confirming by HPLC that the reaction had ended, and an aqueous solution of 48.7% sodium hydroxide was added dropwise thereto at an internal temperature of from 10 to 25° C. until a pH of the solution was from 6.50 to 7.00 (18.1 kg used). After stirring at an internal temperature of from 10 to 20° C. for three hours or longer, solid-liquid separation was carried out with a centrifuge divided into six times. At each centrifugation, after washing the cake with hydrous ethanol (ethanol (2.4 kg)/water (12 kg)) prepared beforehand, the cake was washed with water until a color of the wash was colorless transparent (approximately 200 L). After centrifugal separation was continued further for 30 minutes or longer, and a wet solid was removed into a poly bag. Next, in a shelf dryer, under 45 to 50° C. hot water circulation, the wet solid was dried under a reduced pressure to obtain a solid (71.52 kg).

Next, the solid obtained above (71.45 kg) was added to the 1500 L reactor and washed thereto down with ethanol (approximately 7 kg). Then, ethanol was added up to 226 kg in total and triethylamine (21.6 kg, 1 m/M) was added thereto. Hot water (75° C.) circulation was started, the solution was stirred at an internal temperature of from 70 to 75° C. for 14 to 16 hours, and it was confirmed by HPLC that the reaction had ended. Next, n-heptane (488.7 kg) was added dropwise thereto at an internal temperature of from 55 to 75° C. Thereafter, ethyl 5-{2-[(2,2-dimethylpropanoyl)amino]pyridin-3-yl}isoxazol-3-carboxylate (approximately 5 g) was added thereto at an internal temperature of from 50 to 53° C., and it was confirmed visually that a solid precipitated at an internal temperature of from 45 to 50° C. Then, after the temperature of hot water was decreased gradually, cooling to an internal temperature of 15° C. or lower, further, by brine or cold water cooling, the solution was stirred overnight at an internal temperature of from 0 to 10° C. Using a filtration apparatus, the suspension was filtered and washed with a mixed solution of n-heptane/ethanol (n-heptane (70 kg)/ethanol (10 kg)), followed by n-heptane (80 kg). After drying was carried out in nitrogen for 15 minutes or longer subsequent, a wet solid was removed to a SUS container. In a shelf dryer under 45 to 50° C. hot water circulation, the wet solid was dried under a reduced pressure to obtain the title compound (54.55 kg; yield: 58.6%).

$^1$H-NMR Spectrum (DMSO-d$_6$) δ (ppm): 1.19 (9H, s), 1.32 (3H, t), 4.37 (4H, q), 7.12 (1H, s), 7.46 (1H, dd, J=4.8, 8.0 Hz), 8.25 (1H, dd, J=2.0, 8.0 Hz), 8.58 (1H, dd, J=2.0, 4.8 Hz), 10.03 (1H, s).

HPLC conditions: column: YMC-Pack Pro C18 (5 μm, 150×4.6 mm I.D., YMC), mobile phase: acetonitrile/water/ammonium acetate=300/700/1 to 900/100/1 (v/v/w).

Reference Example 13

Synthesis of [5-(2-aminopyridin-3-yl)isoxazol-3-yl]methanol

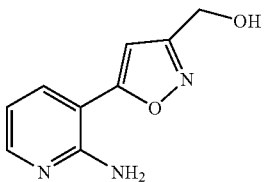

Under a nitrogen gas stream, ethyl 5-{2-[(2,2-dimethylpropanoyl)amino]pyridin-3-yl}isoxazol-3-carboxylate (54.5 kg, 172 mol) was added to a 1500 L reactor and washed thereto down with methanol (4.9 kg). Then, methanol was added thereto until there was 108 kg of methanol in total and triethylamine (8.7 kg, 0.5 m/M) was added consecutively. After hot water (60° C.) circulation was started, the solution was stirred at an internal temperature of from 50 to 60° C. for two hours or longer, and it was confirmed by HPLC (Condition 1) that the reaction had ended.

Next, water cooling was started and tetrahydrofuran (121 kg) was added thereto at an internal temperature of 30° C. or lower. Switching to brine cooling, under a nitrogen gas stream, at an internal temperature of from 0 to 10° C., sodium borohydride (7.15 kg, 1.1 m/M) was added thereto, split over 5 hours or longer. After addition of sodium borohydride was finished, the jacket was switched to cold water (4.0° C.) circulation, and the solution was stirred overnight at an internal temperature of from 0 to 10° C. On the next day, at an internal temperature of from 0 to 10° C., sodium borohydride (1.30 kg, 0.2 m/M) was added thereto, split over one hour or longer. The jacket was switched to cold water, the internal temperature was heated up to from 20 to 30° C. over three hours or longer, and further, the stirring was carried out overnight at an internal temperature of from 20 to 30° C. On the next day, how the reaction was progressing was checked by HPLC, and since the reaction almost did not progress, the solution was cooled again and sodium borohydride (1.30 kg, 0.2 m/M) was split-added at an internal temperature of from 0 to 10° C. After stirring at an internal temperature of from 0 to 10° C. for one hour or longer, the jacket was switched to cold water circulation and heated up to an internal temperature of from 15 to 25° C. over two hours or longer. After stirring for one hour or longer, it was confirmed by HPLC (Condition 1) that the reaction had ended, and the solution was stirred overnight.

The next day, after an aqueous solution of 48.7% sodium hydroxide (71 kg, 5 m/M) was added dropwise thereto at an internal temperature of 50° C. or lower, in continuation, water (133 L) was added dropwise thereto at an internal temperature of 50° C. or lower. Hot water (50 to 80° C.) circulation was started, after stirring at an internal temperature of from 50 to 60° C. for 20 hours or longer, it was confirmed by HPLC (Condition 2) that the reaction had ended.

Next, under a water cooling, water (73 L) was added dropwise thereto. After switching to cold water (15° C.) cooling, [5-(2-aminopyridin-3-yl)isoxazol-3-yl]methanol was added thereto at an internal temperature of from 15 to 30° C., and precipitation of solid was confirmed, water (218 L) was added dropwise thereto, then, under a brine cooling, 35% hydrochloric acid (115 kg) was added dropwise thereto at an internal temperature of from 15 to 30° C., and which was washed there to down with water (3 L). After stirring at an internal temperature of from 15 to 30° C. for five minutes or longer, it was confirmed that a pH of the reaction solution was from 4.00 to 5.00 with a pH meter, and the solution was stirred at an internal temperature of from 15 to 30° C. for one hour or longer. Then, an aqueous solution of 48.7% sodium hydroxide (17.1 kg employment) was added dropwise thereto until a pH of the solution was from 7.00 to 8.00, and the solution was left standing still overnight. On the next day, after stirring and pressure reduction were started and distillation from the condenser was confirmed, hot water (40° C.) circulation was started. Concentration was carried out for one hour or longer under the conditions of hot water (35 to 45° C.), 68 cm Hg or greater level of reduced pressure, and 30° C. or higher internal temperature. The reduced pressure was released under a nitrogen and the solid attached to the reactor wall was washed thoroughly with water (approximately 20 L). The solution was stirred at an internal temperature of from 15 to 30° C. for three hours or longer and was left standing still overnight. On the next day, the internal temperature was confirmed to be within a range of from 15 to 25° C., the slurry solution was solid-liquid separated with a centrifuge, divided in two stages. At each centrifugation, the solid was washed with water (approximately 200 L), after draining, centrifugal separation was carried out for one hour and then the wet solid was taken out into a poly bag. Then, in a shelf dryer, under 45 to 50° C. hot water circulation, the solid was dried under a reduced pressure to obtain the title compound (26.57 kg, yield: 80.9%).

$^1$H-NMR Spectrum (DMSO-d$_6$) δ (ppm): 4.54 (2H, s), 5.57 (1H, brs), 6.25 (2H, brs), 6.71 (1H, dd, J=4.8, 8.0 Hz), 6.90 (1H, s), 7.90 (1H, dd, J=1.6, 7.6 Hz), 8.09 (1H, dd, J=1.6, 4.8 Hz).

HPLC condition 1: column: YMC-Pack Pro C18 (5 μm, 150×4.6 mm I.D., YMC), mobile phase: acetonitrile/water/ammonium acetate=300/700/1 to 900/100/1 (v/v/w).

HPLC condition 2: column: YMC-Pack ODS-AQ (5 μm, 150×4.6 mm I.D., YMC), mobile phase: acetonitrile/water/85% phosphoric acid/sodium 1-octane sulfonate=161.3/838.7/1/1.1 to 900/100/1/1.1 (v/v/v/w).

Reference Examples 14 to 15 are other synthesis methods to Reference Example 10.

Reference Example 14

Synthesis of [5-(2-aminopyridin-3-yl)isoxazol-3-yl]methanol oxalate

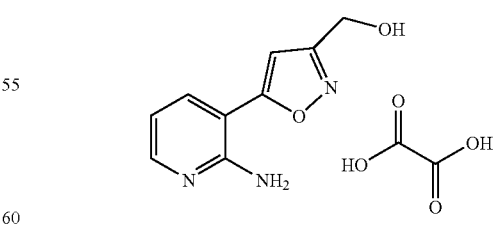

To a mixture of ethyl 5-{2-[(2,2-dimethylpropanoyl)amino]pyridin-3-yl}isoxazol-3-carboxylate (3.17 g, 10 mmol), ethanol (3 mL) and tetrahydrofuran (10 mL) was added sodium borohydride (0.38 g, 10 mmol) at room temperature, which was stirred overnight under a ice cooling to room temperature. The reaction mixture was divided equally into five, among which one was added to 5N aqueous sodium hydroxide (2 mL), which was stirred overnight at 55° C. To the reaction mixture was added water, which was extracted with a mixture of methyl-tert-butylether and tetrahydrofuran, and oxalic acid (0.18 g, 2 mmol) was added to the organic layer. The precipitated solid was filtered to obtain the title compound (0.39 g) as a white solid.

¹H-NMR Spectrum (DMSO-d₆) δ (ppm): 4.54 (2H, s), 6.31 (2H, brs), 6.72 (1H, dd, J=4.8, 8.0 Hz), 6.89 (1H, s), 7.90 (1H, dd, J=2.0, 8.0 Hz), 8.09 (1H, dd, J=2.0, 4.8 Hz).

Reference Example 15

Synthesis of [5-(2-aminopyridin-3-yl)isoxazol-3-yl]methanol

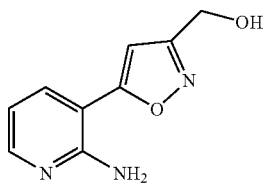 [SMILES: Nc1ncccc1-c1cc(CO)no1]

To a mixture of [5-(2-aminopyridin-3-yl)isoxazol-3-yl]methanol oxalate (0.39 g) and water (2 mL) was added 5N aqueous sodium hydroxide (0.5 mL) at room temperature and the precipitated solid was filtered to obtain the title compound (0.18 g) as a white solid.

¹H-NMR Spectrum (DMSO-d₆) δ (ppm): 4.54 (2H, s), 5.57 (1H, brs), 6.25 (2H, brs), 6.71 (1H, dd, J=4.8, 8.0 Hz), 6.90 (1H, s), 7.90 (1H, dd, J=1.6, 7.6 Hz), 8.09 (1H, dd, J=1.6, 4.8 Hz).

Reference Example 16

Synthesis of 3-[3-(chloromethyl)isoxazol-5-yl]pyridin-2-amine

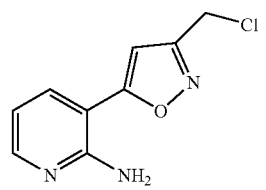 [SMILES: Nc1ncccc1-c1cc(CCl)no1]

To a mixture of [5-(2-aminopyridin-3-yl)isoxazol-3-yl]methanol (0.19 g, 1 mmol) and N,N-dimethyl acetamide (1 mL) was added a mixture of thionyl chloride (0.15 mL, 2 mmol), benzotriazole (0.26 g, 2.2 mmol) and tetrahydrofuran (1 mL) under an ice cooling, which was stirred at room temperature for 30 minutes. To the reaction mixture were added water and 5N aqueous sodium hydroxide to adjust basic, then extracted with ethyl acetate, and the organic layer was washed with saturated sodium chloride water. The solvent was evaporated under a reduced pressure to obtain the title compound (0.21 g) as a pale yellow solid.

¹H-NMR Spectrum (DMSO-d₆) δ (ppm): 4.84 (2H, s), 6.31 (2H, brs), 6.72 (1H, dd, J=4.8, 8.0 Hz), 7.04 (1H, s), 7.91 (1H, dd, J=1.6, 7.6 Hz), 8.11 (1H, dd, J=1.2, 4.8 Hz).

Reference Example 17

Synthesis of di-tert-butyl {3-[3-(chloromethyl)isoxazol-5-yl]pyridin-2-yl}imidodicarbonate

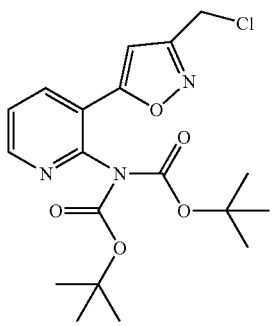 [SMILES: CC(C)(C)OC(=O)N(C(=O)OC(C)(C)C)c1ncccc1-c1cc(CCl)no1]

To a mixture of 3-[3-(chloromethyl)isoxazol-5-yl]pyridin-2-amine (420 mg, 2.01 mmol), 4-dimethyl aminopyridine (26.8 mg, 0.220 mmol), and tetrahydrofuran (2.1 mL) was added di-tert-butyldicarbonate (924 mg, 4.24 mmol) at room temperature, which was stirred. After 25 hours, to the reaction solution was added water and extracted with toluene, then the organic layer was washed with 5% sodium chloride water and the solvent was evaporated under a reduced pressure to obtain the title compound (880 mg) as a pale yellow oily product.

¹H-NMR Spectrum (CDCl₃) δ (ppm): 1.33 (18H, s), 4.63 (2H, s), 6.66 (1H, s), 7.45 (1H, dd, J=4.8, 8.0 Hz), 8.30 (1H, dd, J=2.0, 8.0 Hz), 8.62 (1H, dd, J=2.0, 4.8 Hz).

Reference Examples 18 to 21 are other synthesis methods to Reference Examples 9 to 10 and Reference Examples 16 to 17.

Reference Example 18

Synthesis of tert-butyl {3-[3-(hydroxymethyl)isoxazol-5-yl]pyridin-2-yl}carbamate

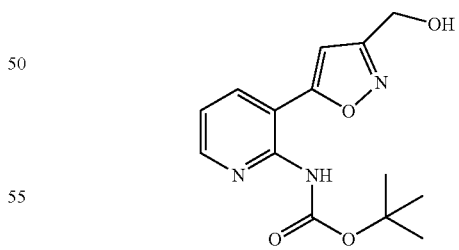

To a mixture of ethyl 5-{2-[(2,2-dimethylpropanoyl)amino]pyridin-3-yl}isoxazol-3-carboxylate (1.59 g, 5 mmol), di-tert-butyl dicarbonate (1.31 g, 6 mmol), and tetrahydrofuran (5 mL) was added 4-dimethylaminopyridine (61 mg, 0.5 mmol) at room temperature, which was stirred at room temperature for one hour and then stirred at 60° C. for six hours. To the reaction mixture were added ethanol (2.5 mL) and sodium borohydride (0.57 g, 15 mmol), which was stirred at 0° C. for 30 minutes and then stirred overnight at room temperature. To the reaction mixture was added water, extracted with ethyl acetate, and the organic layer was washed with water and saturated sodium chloride water. After drying over anhydrous magnesium sulfate and filtering, the solvent was evaporated under a reduced pressure to obtain the title compound (1.60 g).

$^1$H-NMR Spectrum (CDCl$_3$) δ (ppm): 1.47 (9H, s), 4.83 (2H, s), 6.63 (1H, s), 7.17 (1H, dd, J=4.8, 8.0 Hz), 7.58 (1H, s), 7.97 (1H, dd, J=2.0, 8.0 Hz), 8.51 (1H, dd, J=2.0, 4.8 Hz).

Reference Example 19

Synthesis of tert-butyl {3-[3-(chloromethyl)isoxazol-5-yl]pyridin-2-yl}carbamate

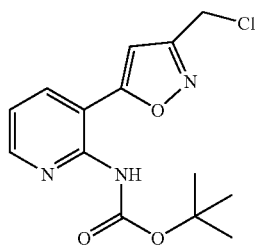 [SMILES: CC(C)(C)OC(=O)Nc1ncccc1-c1cc(CCl)no1]

Under a nitrogen atmosphere, benzotriazole (3.55 g, 29.5 mmol) was dissolved in N,N-dimethylacetamide (10 mL), and thionyl chloride (2.06 mL, 26.8 mmol) was added dropwise thereto under an ice water cooling to prepare a solution of thionyl chloride-benzotriazole (1:1.1) in N,N-dimethylacetamide.

Under a nitrogen atmosphere, tert-butyl {3-[3-(hydroxymethyl)isoxazol-5-yl]pyridin-2-yl}carbamate (781 mg, 2.68 mmol) was dissolved in N,N-dimethylacetamide (2.7 mL). To the solution was added the above solution of thionyl chloride-benzotriazole (1:1.1) in N,N-dimethylacetamide (6 mL, 14.4 mmol) dropwise under an ice water cooling, which was stirred at the same temperature for one hour and then stirred at room temperature. After one hour and 20 minutes, under the ice water cooling, a solution of thionyl chloride-benzotriazole (1:1.1) in N,N-dimethylacetamide (2.2 mL, 5.12 mmol) was added dropwise thereto, and the solution was stirred at room temperature for one hour. Under the ice water cooling, to the reaction solution were added 1N aqueous sodium hydroxide and tert-butylmethylether to adjust basic and then extracted. The organic layer was washed sequentially with 0.5N aqueous sodium hydroxide and 5% sodium chloride water, dried over anhydrous magnesium sulfate and then the solvent was evaporated under a reduced pressure to obtain a crude body of the title compound (953 mg) as a pale yellow oily product.

$^1$H-NMR Spectrum (CDCl$_3$) δ (ppm): 1.47 (9H, s), 4.65 (2H, s), 6.67 (1H, s), 7.20 (1H, dd, J=4.8, 8.0 Hz), 7.44 (1H, brs), 8.01 (1H, dd, J=2.0, 8.0 Hz), 8.52 (1H, dd, J=2.0, 4.8 Hz).

Reference Example 20

Synthesis of di-tert-butyl {3-[3-(chloromethyl)isoxazol-5-yl]pyridin-2-yl}imidodicarbonate

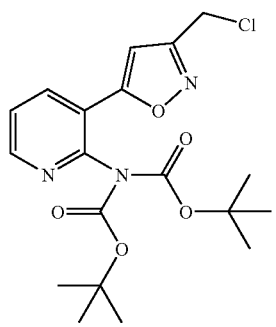 [SMILES: CC(C)(C)OC(=O)N(C(=O)OC(C)(C)C)c1ncccc1-c1cc(CCl)no1]

A crude matter of tert-butyl {3-[3-(chloromethyl)isoxazol-5-yl]pyridin-2-yl}carbamate (1.13 g, 3.17 mmol) was dissolved in tetrahydrofuran (7.0 mL), di-tert-butyl dicarbonate (761 mg, 3.49 mmol) was added thereto under an ice water cooling and washed thereto down with THF (3.0 mL). Then, after 4-dimethylaminopyridine (39.1 mg, 0.317 mmol) was added thereto, the solution was stirred at room temperature. After five hours, under the ice water cooling, to the reaction solution were added ethyl acetate and 5% sodium chloride water and extracted. After the organic layer was washed with 5% sodium chloride water and dried over anhydrous magnesium sulfate, the solvent was evaporated under a reduced pressure. The residue was purified by silica gel column chromatography to obtain the title compound (1.14 g) as a pale yellow solid.

$^1$H-NMR Spectrum (CDCl$_3$) δ (ppm): 1.33 (18H, s), 4.63 (2H, s), 6.66 (1H, s), 7.45 (1H, dd, J=4.8, 8.0 Hz), 8.30 (1H, dd, J=2.0, 8.0 Hz), 8.62 (1H, dd, J=2.0, 4.8 Hz).

Reference Example 21

Synthesis of di-tert-butyl {3-[3-(chloromethyl)isoxazol-5-yl]pyridin-2-yl}imidodicarbonate

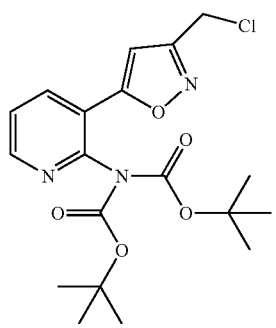 [SMILES: CC(C)(C)OC(=O)N(C(=O)OC(C)(C)C)c1ncccc1-c1cc(CCl)no1]

Under a nitrogen gas stream, [5-(2-aminopyridin-3-yl)isoxazol-3-yl]methanol (26.00 kg, 136.0 mol) and 1,3-dimethyl-2-imidazolidinone (143 kg, 5.5 w/w, a portion was set aside for thorough wash) were added to a 500 L reactor 1 and stirring was started. The solution was stirred at an internal temperature of from 35 to 45° C. for one hour or longer and cooled after dissolution of [5-(2-aminopyridin-3-yl)isoxazol-3-yl]methanol. At an internal temperature of from 5 to 25° C., thionyl chloride (19.40 kg, 163.1 mol, 1.2 m/M) was added dropwise thereto. After the dropwise addition was finished, thionyl chloride was thoroughly washed down with the set aside 1,3-dimethyl-2-imidazolidinone, the solution was stirred an internal temperature of from 5 to 25° C. for 12 hours or longer. After the end of the reaction was confirmed by HPLC analysis, an aqueous solution of approximately 36% sodium hydroxide (mixed solution between an aqueous solution of 48% sodium hydroxide (15.9 kg; 190.8 mol, 1.4 m/M as sodium hydroxide) and water (5.3 kg, 0.2 w/w)) was added dropwise thereto at an internal temperature of from 0 to 25° C., and then ethyl acetate (164 kg, 6.31 w/w) and water (74.2 kg, 2.85 w/w) were added dropwise at an internal temperature of from 15 to 35° C. In addition, after an aqueous solution of approximately 8% sodium hydroxide (mixed solution between a solution of 48% sodium hydroxide (13.6 kg; 163.2 mol, 1.20 m/M as sodium hydroxide) and water (68.0 kg, 2.6 w/w)) was added dropwise thereto at an internal temperature of from 0 to 25° C. and the internal temperature was adjusted to 15 to 30° C., the solution was stirred at the same temperature range for 30 minutes or longer and left standing still for 30 minutes or longer. The lower layer and the upper layer were removed separately, each of the respective ½ weights was added to the 500 L reactor 1 and a 500 L reactor 2.

Post-processing of the 500 L reactor 1 was carried out as described below. After stirring was started and water (52 kg, 2 w/w) was added thereto, an aqueous solution of approximately 8% sodium hydroxide (mixed solution between an aqueous solution of 48% sodium hydroxide (11.3 kg; 135.6 mol, 1.0 m/M as sodium hydroxide) and water (56.5 kg, 2.17 w/w)) was added dropwise little by little at an internal temperature of from 0 to 25° C. to adjust a pH of the lower layer to from 7.00 to 8.50 (actual value: pH7.84). At this time, 35.55 kg of the aqueous solution of approximately 8% sodium hydroxide was used. Then, after the internal temperature was adjusted to 15 to 30° C. and the solution was stirred for 30 minutes or longer, the solution was left standing still overnight. On the next day, after the pH was confirmed again to be pH 7.59, the upper layer and the lower layer were respectively separated, only the lower layer was returned to the 500 L reactor 1, and then ethyl acetate (82 kg, 3.15 w/w) was added thereto. After stirring at an internal temperature of from 15 to 30° C. for five minutes, the solution was left standing still for 30 minutes or longer, and the lower layer (pH7.55) was eliminated. To the upper layer that was left in the reactor were added the separated upper layer and 5% sodium chloride water (mixed solution between sodium chloride (3.3 kg, 0.13 w/w) and water (618 kg, 2.38 w/w)), which was stirred at an internal temperature of from 15 to 30° C. for five minutes, then left standing still for 30 minutes or longer and the lower layer (pH8.23) was eliminated. Furthermore, water (65 kg, 2.5 w/w) was added thereto, the solution was stirred at an internal temperature of from 15 to 30° C. for five minutes and then left standing still overnight, and the lower layer (pH7.04) was eliminated.

The post-processing of the 500 L reactor 2 was conducted concurrently with the operations for the 500 L reactor 1, the same procedure was carried out.

Next, the upper layer of the 500 L reactor 2 was transferred to the 500 L reactor 1, and the solution was concentrated under a reduced pressure at 45 to 55° C. hot water and −0.070 to −0.085 mPa level of the reduced pressure until the content solution was approximately 200 L. Ethyl acetate (141 kg, 5.42 w/w) was added therein, and the solution was concentrated again under a reduced pressure with the same conditions. After this operation was repeated further twice, before and after the 4$^{th}$ time addition of ethyl acetate (141 kg, 5.42 w/w), the 3-[3-(chloromethyl)isoxazol-5-yl]pyridin-2-amine content in the solution was checked by HPLC analysis, the 3-[3-(chloromethyl)isoxazol-5-yl]pyridin-2-amine content (23.35 kg, 111.4 mol) in the solution and the yield thereof (81.9%) were calculated. Then, concentration under a reduced pressure was carried out once more with the same conditions until the 3-[3-(chloromethyl)isoxazol-5-yl]pyridin-2-amine content was 10.0 to 13.0% to obtain a solution of 3-[3-(chloromethyl)isoxazol-5-yl]pyridin-2-amine in ethyl acetate.

Under a nitrogen gas stream, the solution of 3-[3-(chloromethyl)isoxazol-5-yl]pyridin-2-amine in ethyl acetate (containing the total amount obtained in the previous step, 23.35 kg (111.4 mol)) inside the 500 L reactor 1 was stirred, di-tert-butyl dicarbonate (53.47 kg, 245.0 mol, 2.2 m/M) was added thereto at an internal temperature of from 15 to 25° C. and which was washed thereto down with ethyl acetate (2 kg). A solution of 4-dimethyl aminopyridine in ethyl acetate (mixed solution of 4-dimethylaminopyridine (0.409 kg, 3.35 mol, 0.03 m/M) and ethyl acetate (8 kg)) prepared beforehand was added therein, and after washing down with ethyl acetate (1 kg), the solution was stirred at an internal temperature of from 10 to 30° C. for 22 hours or longer. After checking the end of the reaction by HPLC analysis, 1,3-dimethyl-2-imidazolidinone (50 kg, 2.12 w/w) was added thereto. The solution was concentrated under a reduced pressure at 45 to 55° C. hot water circulation, until −0.092 mPa or greater level of the reduced pressure and liquid distillation weakened, and after checking by GC analysis that the ethyl acetate content was 7.0%, the reactor was cooled to an internal temperature of 30° C. or lower, and the solution was left standing still overnight. On the next day, to the concentration residue was added methanol (111 kg, 4.74 w/w), which was stirred for 10 minutes or longer, and it was confirmed that no solid had precipitated, the solution was divided into two fractions. Next, the solutions divided into two fractions were added respectively to the 500 L reactors 1 and 2, and respectively washed thereto down with methanol (9 kg each, 0.4 w/w each). In so doing, as a result of analyzing by HPLC the solution prior to the two fraction division (225.65 kg), the target di-tert-butyl {3-[3-(chloromethyl)isoxazol-5-yl]pyridin-2-yl}imidodicarbonate content was 19.37%, and the weight of di-tert-butyl {3-[3-(chloromethyl)isoxazol-5-yl]pyridin-2-yl}imidodicarbonate contained was 43.71 kg (106.6 mol, yield: 95.7%).

For the 500 L reactor 1 the processing was as described below. After stirring was started, at an internal temperature of from 35 to 45° C., water (35 kg, 1.5 w/w) was added dropwise thereto over 30 minutes or longer, and di-tert-butyl {3-[3-(chloromethyl)isoxazol-5-yl]pyridin-2-yl}imidodicarbonate (0.010 kg) was added thereto at an internal temperature of from 35 to 40° C. After stirring at an internal temperature of from 35 to 40° C. for 30 minutes or longer, precipitation of solid was checked, and the solution was stirred further at the same temperature range for one hour or longer. Then, after water (three times 35 kg, 1.5 w/w each) was added dropwise thereto over 30 minutes or longer at an internal temperature of from 35 to 45° C., the reactor was cooled to an internal temperature of from 5 to 15° C. over 3 hours or longer, and the solution was stirred at the same temperature range for 12 hours or longer. Solid-liquid separation was carried out with a centrifuge dividing into two times, and the cake was washed with hydrous methanol (mixed solution of methanol (each time 7 kg, 0.3 w/w) and water (each time 27 kg, 1.14 w/w)). After washing was finished, centrifugal separation was carried out for 30 minutes or longer to obtain a wet solid of the title compound (25.80 kg). This wet solid was loaded into a mixing type vacuum dryer and vacuum dried at an external temperature from 45 to 55° C. for 24 hours or longer to obtain the title compound (21.09 kg) as a pale yellow solid.

The operation for the 500 L reactor 2 was carried out concurrently with the above, the same operations were performed to obtain the title compound (21.22 kg) as a pale yellow solid.

Accordingly, the title compound (42.31 kg, yield: 92.7%) was obtained.

$^1$H-NMR Spectrum (CDCl$_3$) δ (ppm): 1.33 (18H, s), 4.63 (2H, s), 6.66 (1H, s), 7.45 (1H, dd, J=4.8, 8.0 Hz), 8.30 (1H, dd, J=2.0, 8.0 Hz), 8.62 (1H, dd, J=2.0, 4.8 Hz).

HPLC conditions: column: YMC-Pack Pro C18 (5 μm, 150×4.6 mm I.D., YMC), mobile phase: acetonitrile/water/ammonium acetate=300/700/1 to 900/100/1 (v/v/w).

GC Conditions: column: DB-624 (30 m, 0.53 mm I.D., Film 3 μm, Agilent).

Reference Example 22

Ethyl 5-{2-[(2,2-dimethyl propoxycarbonyl)amino]pyridin-3-yl}isoxazol-3-carboxylate

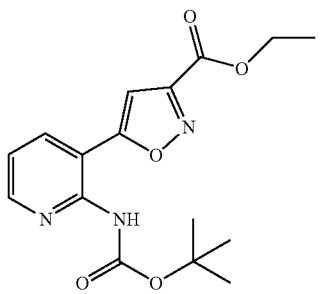 [SMILES: CCOC(=O)c1cc(-c2cccnc2NC(=O)OC(C)(C)C)on1]

To a mixture of 4-methylen-2-oxo-4H-pyrido[2,3-d][1,3]oxazin-1-carboxylic acid tert-butyl ester (2.71 g, 10.37 mmol), which was synthesized according to the methods described in the pamphlet of the International Publication WO 08/136,279, Specifications, Preparation Example 3-3-1, triethylamine (4.2 mL, 30 mmol) and tetrahydrofuran (30 mL) was added ethyl 2-chloro-2-(hydroxyimino)acetate (4.5 g, 30 mmol) at 0° C. over two hours and then stirred at room temperature for 14 hours. To the reaction mixture was added water, extracted with ethyl acetate and the organic layer was washed with water and saturated sodium chloride water. After drying over magnesium sulfate and filtering, the solvent was evaporated under a reduced pressure. The residue was suspended and washed with a 1:1 mixture of n-hexane and ethyl acetate to obtain the title compound (1.56 g).

$^1$H-NMR Spectrum (CDCl$_3$) δ (ppm): 1.44 (3H, t, J=6.8 Hz), 1.46 (9H, s), 4.47 (4H, q, J=7.2 Hz), 6.95 (1H, s), 7.22 (1H, dd, J=4.8, 8.0 Hz), 7.42 (1H, bs), 8.05 (1H, dd, J=2.0, 8.0 Hz), 8.52 (1H, dd, J=2.0, 4.8 Hz).

Reference Example 23

Ethyl 5-{2-[bis(2,2-dimethylpropoxy-carbonyl)amino]pyridin-3-yl}isoxazol-3-carboxylate

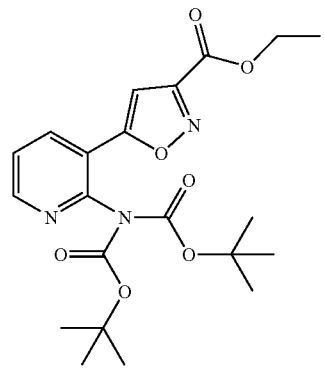 [SMILES: CCOC(=O)c1cc(-c2cccnc2N(C(=O)OC(C)(C)C)C(=O)OC(C)(C)C)on1]

To a mixture of ethyl 5-{2-[(2,2-dimethylpropoxycarbonyl)amino]pyridin-3-yl}isoxazol-3-carboxylate (1.46 g, 4.38 mmol), di-tert-butyl dicarbonate (1.46 g, 6.69 mmol) and tetrahydrofuran (25 mL) was added 4-dimethylaminopyridine (30 mg, 0.25 mmol) at room temperature, which was stirred at room temperature for 14 hours. To the reaction mixture was added water, extracted with ethyl acetate, and the organic layer was washed with water and saturated sodium chloride water. After drying over magnesium sulfate and filtering, the solvent was evaporated under a reduced pressure and the residue was purified by silica gel column chromatography (hexane:ethyl acetate=3:1 then 1:1) to obtain the title compound (1.96 g).

$^1$H-NMR Spectrum (CDCl$_3$) δ (ppm): 1.36 (18H, s), 1.46 (3H, t, J=6.8 Hz), 4.47 (4H, q, J=6.8 Hz), 6.93 (1H, s), 7.46 (1H, dd, J=4.8, 7.6 Hz), 8.29 (1H, d, J=7.6 Hz), 8.64 (1H, d, J=4.8 Hz).

Reference Example 24

Di-tert-butyl {3-[3-(hydroxymethyl)isoxazol-5-yl]pyridin-2-yl}imidodicarbonate

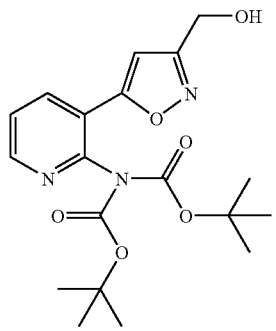 [SMILES: CC(C)(C)OC(=O)N(C(=O)OC(C)(C)C)c1ncccc1-c1cc(CO)no1]

To a mixture of ethyl 5-{2-[bis(2,2-dimethylpropoxycarbonyl)amino]pyridin-3-yl}isoxazol-3-carboxylate (1.73 g, 4 mmol), ethanol (5 mL) and tetrahydrofuran (5 mL) was added sodium borohydride (0.15 g, 4 mmol) at 0° C., which was stirred at room temperature for one hour. Sodium borohydride (0.15 g, 4 mmol) was further added thereto and the solution was stirred at room temperature for three hours. To the reaction mixture was added water, extracted with ethyl acetate and the organic layer was washed with water and saturated sodium chloride water. After drying over anhydrous magnesium sulfate and filtering, the solvent was evaporated under a reduced pressure. The residue was added with a mixture of n-hexane-ethyl acetate (1:1), suspended and stirred, and then filtered to obtain the title compound (1.02 g).

$^1$H-NMR Spectrum (CDCl$_3$) δ (ppm): 1.33 (18H, s), 4.81 (2H, s), 6.60 (1H, s), 7.43 (1H, dd, J=4.8, 8.0 Hz), 8.27 (1H, dd, J=2.0, 8.0 Hz), 8.60 (1H, dd, J=2.0, 4.8 Hz).

Reference Example 25

Di-tert-butyl {3-[3-(bromomethyl)isoxazol-5-yl]pyridin-2-yl}imidodicarbonate

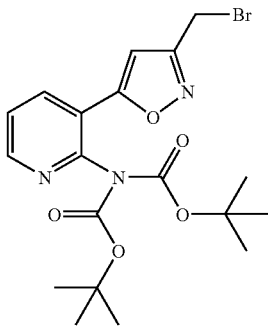 [SMILES: CC(C)(C)OC(=O)N(C(=O)OC(C)(C)C)c1ncccc1-c1cc(CBr)no1]

To a mixture of di-tert-butyl {3-[3-(hydroxymethyl)isoxazol-5-yl]pyridin-2-yl}imidodicarbonate (0.78 g, 2 mmol), triethylamine (1.95 mL, 14 mmol) and 1,2-dimethoxyethane (10 mL) was added phosphorus tribromide (0.37 mL, 4 mmol) dropwise at 0° C., which was stirred at room temperature for two hours, and then stirred at 50° C. for 30 minutes. The reaction mixture was cooled to 0° C., then water was added thereto and extracted with ethyl acetate, and the organic layer was washed with saturated sodium chloride water. After drying over anhydrous magnesium sulfate and filtering, the solvent was evaporated under a reduced pressure, the residue was purified by silica gel column chromatography to obtain the title compound (0.14 g).

$^1$H-NMR Spectrum (CDCl$_3$) δ (ppm): 1.33 (18H, s), 4.45 (2H, s), 6.63 (1H, s), 7.43 (1H, dd, J=4.8, 8.0 Hz), 8.28 (1H, dd, J=2.0, 8.0 Hz), 8.61 (1H, dd, J=2.0, 4.8 Hz).

Reference Example 26

Synthesis of 2-[(4-bromobenzyl)oxy]pyridine

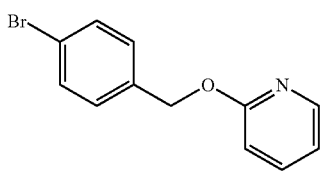

To a solution of 4-bromobenzyl alcohol (18 g, 94.3 mmol) in dimethylsulfoxide (85 mL) was added potassium tert-butoxide (11.5 g, 99 mmol) little by little under a nitrogen atmosphere at room temperature, which was stirred for 10 minutes. To this solution was added 2-fluoropyridine (12.3 g, 123 mmol) dropwise over 30 minutes under a water bath cooling. After stirring at room temperature for two hours, ethyl acetate and 5% sodium chloride water were added, and extracted. After the organic layer was washed sequentially with water and 5% sodium chloride water, the solvent was evaporated under a reduced pressure to obtain the title compound (24.3 g) as a yellow oily product.

$^1$H-NMR Spectrum (CDCl$_3$) δ (ppm): 5.33 (2H, s), 6.87-6.70 (1H, m), 6.98-7.02 (1H, m), 7.38-7.44 (2H, m), 7.55-7.60 (2H, m), 7.71-7.76 (1H, m), 8.15-8.18 (1H, m).

Reference Example 27 is the other synthesis method to Reference Example 26.

Reference Example 27

Synthesis of 2-[(4-bromobenzyl)oxy]pyridine

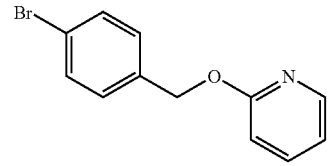 [SMILES: Brc1ccc(COc2ccccn2)cc1]

Under a nitrogen atmosphere, to a solution of 4-bromobenzyl alcohol (600 g, 3.21 mol) and 2-fluoropyridine (343 g, 3.53 mol) in tetrahydrofuran (1069 mL) was added a solution of potassium tert-butoxide (396 g, 3.53 mol) in tetrahydrofuran (3208 mL) (63 min, 9.2 to 20.5° C.) dropwise under a 7° C. cooling. After stirring at 22° C. for three hours, an aqueous solution of 5% sodium bicarbonate (prepared from sodium bicarbonate: 160 g and water: 3208 mL) was added thereto dropwise (20 min, 21.0 to 23.9° C.). Then, heptane (3220 mL) was added thereto and extracted, the organic layer was washed with water (800 mL). The organic layer was concentrated under a reduced pressure (to approximately 3200 mL), ethanol (1604 mL) was added thereto and concentrated under a reduced pressure (to approximately 3200 mL). Then, to the layer was added heptane (3200 mL), concentrated under a reduced pressure, heptane (3200 mL) was further added thereto and concentrated under a reduced pressure to obtain a solution of the title compound in heptane (2603 g, containing 789 g of the target product) as a brown oily product (yield: 93.2%).

$^1$H-NMR Spectrum (CDCl$_3$) δ (ppm): 5.33 (2H, s), 6.87-6.70 (1H, m), 6.98-7.02 (1H, m), 7.38-7.44 (2H, m), 7.55-7.60 (2H, m), 7.71-7.76 (1H, m), 8.15-8.18 (1H, m).

Reference Example 28

Synthesis of {4-[(pyridin-2-yloxy)methyl]phenyl}boronic acid

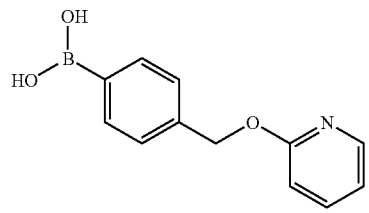 [SMILES: OB(O)c1ccc(COc2ccccn2)cc1]

Under a nitrogen atmosphere, a solution of 2-[(4-bromobenzyl)oxy]pyridine (50 g, 190 mmol) in tetrahydrofuran (200 mL) was cooled to −78° C. and a 2.6 m n-butyllithium hexane solution (88 mL, 228 mmol) was added thereto dropwise. After stirring for 45 minutes, trimethoxy borane (29.6 g, 285 mmol) was added thereto dropwise at the same temperature. After 30 minutes, a saturated aqueous solution of ammonium chloride and water were added thereto for quenching, and the solution was extracted with ethyl acetate. After the organic layer was washed with a mixture of saturated aqueous solution of ammonium chloride and saturated sodium chloride water and dried over anhydrous sodium sulfate, the solvent was evaporated under a reduced pressure. To the residue was added acetonitrile (200 mL), followed by suspending and stirring at 70° C. for 30 minutes, then, cooled, and stirred overnight at 4° C. The precipitated solid was filtered to obtain the title compound (11.2 g) as a white solid.

$^1$H-NMR Spectrum (CDCl$_3$) δ (ppm): 4.62 (2H, s), 5.42 (2H, s), 6.83 (1H, d, J=8.4 Hz), 6.87-6.92 (1H, m), 7.50 (2H, d, J=8.0 Hz), 7.57-7.62 (1H, m), 7.75 (2H, d, J=8.0 Hz), 8.16-8.19 (1H, m).

Reference Example 29

Synthesis of 2-{[4-(5,5-dimethyl-1,3,2-dioxaborinan-2-yl)benzyl]oxy}pyridine

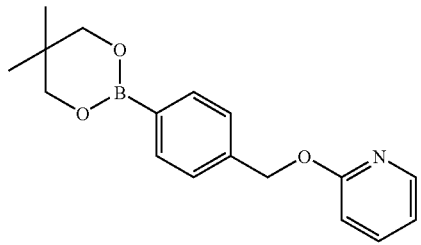 [SMILES: CC1(C)COB(c2ccc(COc3ccccn3)cc2)OC1]

To a solution of 2-[(4-bromobenzyl)oxy]pyridine (789 g, 2.99 mol) in heptane (2603 g) were added heptane (939 mL) and tetrahydrofuran (1199 mL), which was cooled slowly with dry ice/ethanol bath under a nitrogen atmosphere, while stirring. After 45 minutes, cooling was stopped and 2-[(4-bromobenzyl)oxy]pyridine (0.9 g) was added thereto at an internal temperature of −12° C. Cooling was resumed, with cooling at −20° C./h. Approximately 3 hours later, 1.66 m n-butyllithium hexane solution (1980 mL, 3.29 mol) was added thereto dropwise (80 min, −67.0 to 61.4° C.). After stirring for 0.5 hours, at the same temperature, triisopropoxy borane (674 g, 3.56 mol) was added thereto dropwise (134 min, −68.2 to 60.3° C.). At the same temperature, after stirring for 0.5 hours, switching to an ice water bath cooling, the solution was stirred overnight (external temperature: 0° C.). On the next day, water (5600 mL) was added thereto dropwise, the solution was transferred to a separator vessel and was extracted into the aqueous layer (pH: 11.2). Ethyl acetate (4800 mL) was added thereto and concentrated hydrochloric acid (approximately 280 mL) was added thereto dropwise (at an internal temperature of 20° C. or lower) while stirring, to adjust the solution to pH: 7.1. The organic layer was separated and washed with 5% sodium chloride water (approximately 900 g) and then concentrated under a reduced pressure. To the residue was added isopropyl alcohol (3300 mL), concentrated under a reduced pressure, isopropyl alcohol (3300 mL) was further added thereto and concentrated under a reduced pressure to obtain a solution of {4-[(pyridin-2-yloxy)methyl]phenyl}boronic acid (646 g) in isopropyl alcohol (2671 g) (yield: 94.4%). The obtained solution was heated to 60° C., which was added to a container containing 2,2-dimethyl-1,3-propanediol (354 g, 3.41 mol) while eliminating insoluble matter by suction-filtration, and then which was washed thereto down with isopropyl alcohol (685 mL). After confirming dissolution, the solution was stirred at a bath temperature of 20° C. and crystal precipitation was observed at an internal temperature of 28.8° C. After 1.5 hours, the bath temperature was set to −20° C., and the solution was stirred overnight. The precipitated crystal was filtered, and the crystal was washed with a small amount of isopropyl alcohol cooled to 0° C. The crystal was dried under a reduced pressure to obtain the title compound (779 g) as a white crystal (yield: 92.2%).

$^1$H-NMR Spectrum (DMSO-d$_6$) δ (ppm): 0.94 (6H, s), 3.74 (4H, s), 5.35 (2H, s), 6.87 (1H, d, J=8.4 Hz), 6.96-7.00 (1H, m), 7.39 (2H, d, J=8.0 Hz), 7.67-7.74 (3H, m), 8.14-8.17 (1H, m).

Reference Example 30

Synthesis of di-tert-butyl[3-(3-{4-[(pyridin-2-yloxy)methyl]benzyl}isoxazol-5-yl)pyridin-2-yl]imidodicarbonate

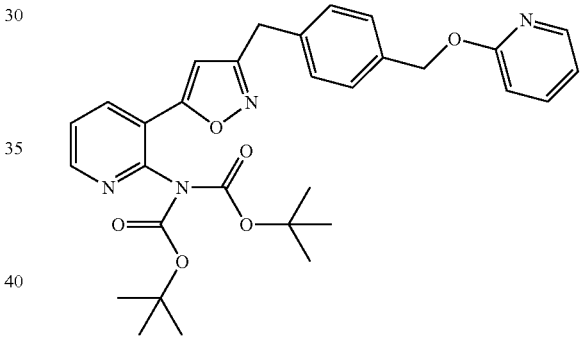

Under nitrogen atmosphere, to a mixture of di-tert-butyl {3-[3-(chloromethyl)isoxazol-5-yl]pyridin-2-yl}imidodicarbonate (164 mg, 0.40 mmol), {4-[(pyridin-2-yloxy)methyl]phenyl}boronic acid (138 mg, 0.60 mmol), cesium carbonate (391 mg, 1.20 mmol), copper (1) iodide (3.9 mg, 5 mol %) and 1,2-dimethoxyethane (2.0 mL) was added [1,1'-bis(diphenylphosphino)ferrocene]dichloropalladium (II) dichloromethane complex (16.4 mg, 5 mol %), which was stirred at 80° C. for 1.5 hours. {4-[(Pyridin-2-yloxy)methyl]phenyl}boronic acid (46 mg, 0.20 mmol) was added thereto and the solution was further stirred for 4.5 hours. After cooling, ethyl acetate and 5% sodium chloride solution were added thereto, insoluble matter was filtered out, then, the filtrate was transferred to a separatory funnel and separated. After the organic layer was washed with 5% sodium chloride water and dried over anhydrous magnesium sulfate, the solvent was evaporated under a reduced pressure. The residue was purified by silica gel column chromatography to obtain the title compound (173 mg) as a pale yellow oily product.

$^1$H-NMR Spectrum (CDCl$_3$) δ (ppm): 1.23 (9H, s), 4.05 (2H, s), 5.34 (2H, s), 6.32 (1H, s), 6.76-6.79 (1H, m), 6.86-6.90 (1H, m), 7.28 (2H, d, J=8.0 Hz), 7.38-7.43 (3H, m), 7.55-7.60 (1H, m), 8.15-8.18 (1H, m), 8.27 (1H, dd, J=2.0, 8.0 Hz), 8.57 (1H, dd, J=2.0, 7.6 Hz).

Reference Example 31

3-(3-(4-Pyridin-2-yloxymethyl)-benzyl)-isoxazol-5-yl)-pyridin-2-ylamine

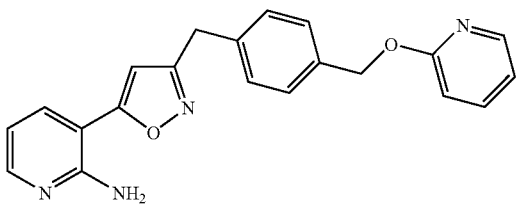 [SMILES: Nc1ncccc1-c1cc(Cc2ccc(COc3ccccn3)cc2)no1]

Di-tert-butyl[3-(3-{4-[(pyridin-2-yloxy)methyl]benzyl}isoxazol-5-yl)pyridin-2-yl]imidodicarbonate (28.8 mg, 51.6 μmol) was dissolved in acetonitrile (0.6 mL), concentrated hydrochloric acid (60 μL, 690 μmol) was added thereto dropwise under an ice water cooling, which was stirred at the same temperature for one hour. Concentrated hydrochloric acid (140 μL, 1.61 mmol) was further added thereto dropwise and the solution was stirred at the same temperature for one hour and at 20° C. for 3.5 hours. Under an ice water cooling, to the reaction solution were added 0.5N aqueous sodium hydroxide and ethyl acetate and extracted. After the organic layer was washed with 5% sodium chloride water and dried over anhydrous magnesium sulfate, the solvent was evaporated under a reduced pressure to obtain the title compound (18.3 mg) as a pale yellow oily product.

$^1$H-NMR Spectrum (CDCl$_3$) δ (ppm): 4.07 (2H, s), 5.37 (2H, s), 5.42 (2H, brs), 6.25 (1H, s), 6.71 (1H, dd, J=5.2, 7.6 Hz), 6.80 (1H, d, J=8.4 Hz), 6.87-6.91 (1H, m), 7.30 (2H, d, J=7.6 Hz), 7.44 (2H, d, J=7.6 Hz), 7.56-7.61 (1H, m), 7.70 (1H, dd, J=2.0, 7.6 Hz), 8.14 (1H, dd, J=2.0, 4.8 Hz), 8.16-8.19 (1H, m).

Reference Examples 32 to 33 are other synthesis methods to Reference Examples 30 to 31.

Reference Example 32

Synthesis of di-tert-butyl[3-(3-{4-[(pyridin-2-yloxy)methyl]benzyl}isoxazol-5-yl)pyridin-2-yl]imidodicarbonate

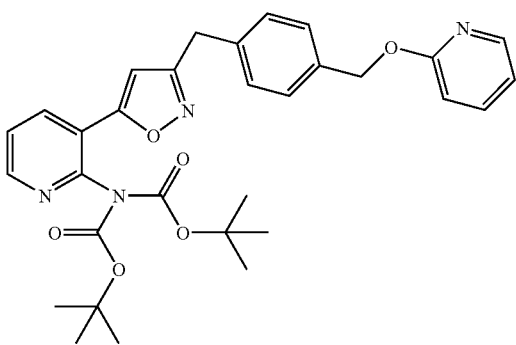 [SMILES: CC(C)(C)OC(=O)N(C(=O)OC(C)(C)C)c1ncccc1-c1cc(Cc2ccc(COc3ccccn3)cc2)no1]

The operation of the first batch was carried out as described below. Under a nitrogen gas stream, after di-tert-butyl {3-[3-(chloromethyl)isoxazol-5-yl]pyridin-2-yl}imidodicarbonate (20.80 kg, 50.75 mol), 2-{[4-(5,5-dimethyl-1,3,2-dioxaborinan-2-yl)benzyl]oxy}pyridine (19.61 kg, 66.00 mol, 1.30 m/M), (oxydi-2,1-phenylene)bis(diphenylphosphine) (1.367 kg, 2.54 mol, 0.05 m/M), potassium carbonate (9.11 kg, 65.91 mol, 1.30 m/M) were added to a 500 L reactor 2 which was nitrogen-substituted beforehand, the interior of the reactor was nitrogen-substituted again, N,N-dimethyl formamide (147 kg, 7.08 w/w) was added thereto and stirring was started. Then, after maintaining at an internal temperature of from 15 to 25° C. and a level of the reduced pressure of –0.090 mPa or greater for three to five minutes maintenance, the reduced pressure was released with nitrogen. This operation was repeated five times to degas the solution. After degassing was finished, solution of palladium acetate in N,N-dimethyl formamide (mixed solution of palladium acetate (0.570 kg, 2.54 mol, 0.05 m/M) and degassed N,N-dimethyl formamide (9.8 kg, 0.5 w/w, a portion of which was set aside for thorough wash)) was added thereto, and washed thereto down with the set aside degassed N,N-dimethyl formamide. Next, after stirring for 10 minutes, immediately degassed water (10.4 kg, 0.5 w/w) was added thereto dropwise at an internal temperature of from 20 to 30° C., and the operation of reducing the pressure to –0.087 mPa level of the reduced pressure and releasing the reduced pressure with nitrogen was repeated three times. Thereafter, hot water at approximately 60° C. was circulated quickly to adjust the internal temperature to from 55 to 65° C. and the solution was stirred for three hours from the start of the heating. After the end of the reaction was confirmed by HPLC analysis, toluene (90 kg, 4.34 w/w) was added thereto at an internal temperature of from 0 to 25° C. and water (156 kg, 7.5 w/w) was added thereto dropwise at the same temperature range. Then, after stirring at an internal temperature of from 15 to 30° C. for 30 minutes, the solution was left standing still for 30 minutes or longer standing, and the lower layer was eliminated. To the upper layer inside of the reactor was added water (104 kg, 5.0 w/w), which was stirred at an internal temperature of from 15 to 30° C. for five minutes, then left standing still overnight, and only the lower layer containing no insoluble matter was eliminated. The upper layer and the lower layer containing insoluble matter were filtered with Celite 503 RV (2.8 kg, 0.135 w/w) under pressure by a filtration device, and the reactor and the filtration device were pour-washed with toluene (18.0 kg, 0.867 w/w, a portion was set aside for flushing and thorough washing). The obtained filtrate and washes were returned to the 500 L reactor 2 and washed thereto down with the previously set aside toluene. Subsequently, after the internal temperature was adjusted to 15 to 30° C., the solution was left standing still for 30 minutes or longer, and the lower layer was eliminated. After the stirring speed was adjusted to approximately maximum and n-heptane (152 kg, 7.32 w/w) was added thereto dropwise over one hour or longer at an internal temperature of from 15 to 30° C., the solution was stirred at the same temperature range for two hours or longer. Then, after thiocyanuric acid (0.90 kg, 5.08 mol, 0.1 m/M) was added thereinto with divided fractions over 30 minutes or longer at an internal temperature of from 15 to 30° C., the solution was stirred at the same temperature range for one hour or longer. Once more, thiocyanuric acid (0.90 kg, 5.08 mol, 0.1 m/M) was added thereinto with divided fractions over 30 minutes or longer at an internal temperature of from 15 to 30° C. and the solution was stirred overnight at the same temperature range. After overnight stirring, the solution in the reactor was filtered with activated carbon by a filtration device which was prepared beforehand, and the reactor and the filtration device were washed thoroughly with a mixed solution of n-heptanetoluene (mixed solution of n-heptane (130 kg) and toluene (83 kg), a portion of which was set aside for wetting the activated carbon (Seisei Shirasagi)). After adding thiocyanuric acid (1.80 kg, 10.16 mol, 0.2 m/M) thereinto once more, filtration with activated carbon was carried out using the same amount of Celite 503 RV, activated carbon (Seisei Shirasagi) and mixed solution of n-heptane-toluene. The obtained filtrate and washes were added to the 500 L reactor 1, which was concentrated under a reduced pressure and hot water circulation at 40 to 70° C. until the content solution was approximately 100 L visually. And, the residue was left standing still under a nitrogen atmosphere and at an internal temperature of 30° C. or lower until activated carbon filtration of the second batch was finished.

As a second batch, the same operation as described above was carried out. The filtrate and washes of the second batch were added to the 500 L reactor 1 to be pooled with the residue of the first batch, and concentration under a reduced pressure was started. Under hot water circulation at 60 to 70° C., when the distillate outflow had weakened, toluene (144 kg) was added thereto, then, again, under hot water circulation at 60 to 70° C., concentration under a reduced pressure was carried out until distillate outflow weakened. At this point, the residue was analyzed and the toluene/target product ratio (0.167 w/w) was calculated from the di-tert-butyl[3-(3-{4-[(pyridin-2-yloxy)methyl]benzyl}isoxazol-5-yl)pyridin-2-yl]imido dicarbonate content and the toluene content in the concentration residue. Toluene (29.66 kg, corresponding to a toluene/target product ratio of 0.700 w/w) was added thereto, the solution was stirred at an internal temperature of from 15 to 30° C. for 30 minutes or longer to obtain a toluene solution of title compound (containing 42.37 kg of the target product; yield: 74.7%).

HPLC conditions: column: CAPCELL PAK C18 mGII (5 μm, 150×4.6 mm I.D., SHISEIDO), mobile phase: acetonitrile/water/trifluoroacetic acid=180/820/1 to 900/100/1 (v/v/v).

Reference Example 33

3-(3-(4-Pyridin-2-yloxymethyl)-benzyl)-isoxazol-5-yl)-pyridin-2-ylamine

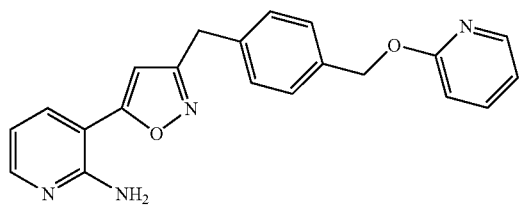 [SMILES: Nc1ncccc1-c1cc(Cc2ccc(COc3ccccn3)cc2)no1]

To a toluene solution of di-tert-butyl[3-(3-{4-[(pyridin-2-yloxy)methyl]benzyl}isoxazol-5-yl)pyridin-2-yl]imido dicarbonate (containing 42.37 kg (75.85 mol)) was added formic acid (181 kg, 4.27 w/w) dropwise at an internal temperature of from −5 to 20° C., which was stirred at an internal temperature of from 22 to 32° C. for 19 to 20 hours. After the end of the reaction was confirmed by HPLC analysis, the internal temperature was cooled to −5 to 10° C. and the content solution was divided into two fractions and added to the 500 L reactors 1 and 2, respectively.

For the 500 L reactor 1, post-processing was carried out as described below. Under stirring, water (74 kg, 1.75 w/w) was added thereto dropwise at an internal temperature of from −5 to 20° C., further, tert-butylmethylether (31.4 kg, 0.74 w/w) and n-heptane (29.0 kg, 0.684 w/w) were added thereto at an internal temperature of from 0 to 25° C. The solution was stirred at an internal temperature of from 15 to 25° C. for five minutes, left standing still for 30 minutes or longer to separate the lower layer. The lower layer was returned to the reactor, tert-butylmethylether (31.4 kg, 0.74 w/w) and n-heptane (29.0 kg, 0.684 w/w) were added thereto again at an internal temperature of from 0 to 25° C., the solution was stirred at an internal temperature of from 15 to 25° C. for five minutes, then, left standing still for 30 minutes or longer, and the lower layer was separated again. The lower layer was returned to the reactor and, first, an aqueous solution of 48% sodium hydroxide (116 kg; 1392.0 mol, 18.35 m/M as sodium hydroxide) was added dropwise at an internal temperature of from 0 to 25° C. Next, at the same temperature range, ethyl acetate (96 kg, 2.26 w/w) was added thereto and an aqueous solution of 48% sodium hydroxide (20.5 kg; 246.0 mol, 3.24 m/M as sodium hydroxide) was added thereto dropwise. In addition, herein, at same temperature range, an aqueous solution of approximately 8% sodium hydroxide (mixed solution of an aqueous solution of 48% sodium hydroxide (12.7 kg; 152.4 mol, 2.00 m/M as sodium hydroxide) and water (64 kg, 1.5 w/w)) was added thereto dropwise until a pH of the lower layer was pH 8.00 to 9.00, (actual value: pH 8.58) (0.75 kg used). Thereafter, the solution was stirred for one hour or longer at an internal temperature of from 20 to 30° C. and left standing still overnight, then, the pH of the lower layer was checked again (actual value: pH 8.29) and the lower layer was eliminated. To the upper layer remaining in the reactor was added an aqueous solution of approximately 5% sodium bicarbonate (mixed solution of sodium bicarbonate (5.3 kg, 63.09 mol) and water (101 kg, 2.375 w/w)), which was stirred at an internal temperature of from 20 to 30° C. for one hour or longer and then left standing still for 30 minutes or longer. After the lower layer (pH8.60) was eliminated, to the upper layer was added water (106 kg, 2.5 w/w), which was stirred at an internal temperature of from 20 to 30° C. for one hour or longer, then, left standing still for 30 minutes or longer, and the lower layer (pH7.17) was eliminated again.

For the 500 L reactor 2, the same post-processing was carried out concurrently with the 500 L reactor 1.

The content solution of the 500 L reactor 1 was transferred to the 500 L reactor 2 and concentrated under a reduced pressure under hot water circulation at 55 to 65° C. until the content solution was approximately 100 L. Next, to the concentration residue were added ethanol (42 kg, 1.0 w/w) and ethyl acetate (96 kg, 2.26 w/w), which was stirred for five minutes, then, concentrated under a reduced pressure under hot water circulation at 55 to 65° C. until a level of the reduced pressure of −0.092 mPa or greater and almost no distillate outflow was observed. At this point, as precipitation of crystal was observed, ethyl acetate was added little by little until the crystal dissolved completely (13.85 kg used). After ethanol (18.3 kg) and ethyl acetate (6.7 kg) were further added, the internal temperature was adjusted to 50 to 55° C., and after confirming visually that the crystal was dissolved, n-heptane (33.5 kg, 0.79 w/w) was added thereto over 30 minutes or longer at an internal temperature of from 45 to 55° C. Then, after 3-(3-(4-pyridin-2-yloxymethyl)-benzyl)-isoxazol-5-yl)-pyridin-2-ylamine (0.011 kg), which can be synthesized according to the methods described in the pamphlet of the International Publication WO 08/136,279, Specifications, Example 18, was added thereto at an internal temperature of from 45 to 50° C. and precipitation of crystal was observed, the solution was stirred at the same temperature range for one hour or longer. After n-heptane (66.9 kg, 1.58 w/w) was added dropwise over one hour or longer at an internal temperature of from 45 to 55° C., the internal temperature was cooled to 0 to 10° C. over four hours or longer, and the solution was stirred at the same temperature range for five hours or longer. After the content solution was sampled and it was confirmed that the rate of crystallization of the target product was 94%, the suspension was filtered under pressure, the crystal was pour-washed in the order with mixed solution of ethanol-ethyl acetate-n-heptane (mixed solution of ethanol (3.60 kg, 0.085 w/w), ethyl acetate (4.15 kg, 0.098 w/w) and n-heptane (18.81 kg, 0.444 w/w)), and mixed solution of ethanol-n-heptane (mixed solution of ethanol (7.25 kg, 0.171 w/w) and n-heptane (18.81 kg, 0.444 w/w)) to obtain a wet crude crystal of the title compound (36.52 kg) as a slightly yellow crystal.

The obtained wet crude crystal of 3-(3-(4-pyridin-2-yloxymethyl)-benzyl)-isoxazol-5-yl)-pyridin-2-ylamine (36.52 kg) and ethanol (57.9 kg, 2.37 w/w) were added sequentially to a 500 L dissolution can, which was nitrogen-substituted beforehand, and heated to an internal temperature of from 70 to 75° C. to dissolve the crystal. While maintaining the temperature, this dissolution solution was transferred through a SUS filter to a 500 L crystallization can, and the 500 L dissolution can and SUS filter were washed thoroughly with ethanol (19.3 kg, 0.8 w/w) which was kept heated at an external temperature of approximately 65° C. Next, the filtrate was adjusted to an internal temperature of from 55 to 60° C., and it was confirmed that the solution inside the can was homogenous. Thereafter, when the internal temperature was cooled slowly to 48 to 51° C., crystal precipitated. After heating again to an internal temperature of from 55 to 60° C. to dissolve the crystal, immediately the internal temperature was cooled to 48 to 51° C. and 3-(3-(4-pyridin-2-yloxymethyl)-benzyl)-isoxazol-5-yl)-pyridin-2-ylamine (0.011 kg), which can be synthesized according to the methods described in the pamphlet of the International Publication WO 08/136, 279, Specifications, Example 18, was added immediately. Then, after precipitation of crystal was confirmed visually at an internal temperature of from 45 to 50° C., the suspension was stirred at an internal temperature of from 43 to 47° C. for one hour to one hour and 30 minutes, and the internal temperature was cooled to 0 to 10° C. over four hours or longer. At this point, after a precipitated crystal was sampled and the crystal form thereof was confirmed to be identical to the reference sample, the suspension was stirred overnight at the same temperature range. On the next day, after the crystal form was confirmed to be identical to the reference sample, the crystal was solid-liquid separated with a centrifuge divided in two times, and respectively pour-washed with approximately half of the amount of 19.3 kg of ethanol to obtain a wet crystal of the target product (24.23 kg). This wet crystal was placed into a mixed type vacuum dryer and dried under a reduced pressure at an external temperature of from 20 to 30° C. for 6 hours or longer and an external temperature of from 35 to 45° C. for 12 hours or longer to obtain the title compound (23.52 kg, 65.63 mol, yield: 86.8%) as a pale yellow crystal.

$^1$H-NMR Spectrum (CDCl$_3$) δ (ppm): 4.07 (2H, s), 5.37 (2H, s), 5.42 (2H, brs), 6.25 (1H, s), 6.71 (1H, dd, J=5.2, 7.6 Hz), 6.80 (1H, d, J=8.4 Hz), 6.87-6.91 (1H, m), 7.30 (2H, d, J=7.6 Hz), 7.44 (2H, d, J=7.6 Hz), 7.56-7.61 (1H, m), 7.70 (1H, dd, J=2.0, 7.6 Hz), 8.14 (1H, dd, J=2.0, 4.8 Hz), 8.16-8.19 (1H, m).

HPLC conditions: column: CAPCELL PAK C18 mGII (5 μm, 150×4.6 mm I.D., SHISEIDO), mobile phase: acetonitrile/water/trifluoroacetic acid=180/820/1 to 900/100/1 (v/v/v).

Example 1

2-Amino-1-((phosphonoxy)methyl)-3-(3-((4-((2-pyridinyloxy)methyl)phenyl)methyl)-5-isoxazolyl)-pyridinium

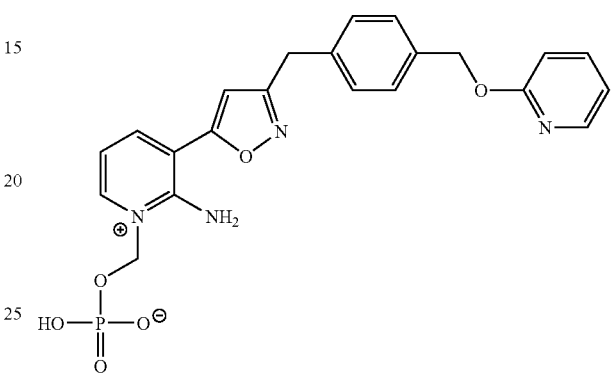

To a mixture of phosphoric acid di-tert-butyl ester chloromethyl ester (1.5 g, 5.6 mmol), sodium iodide (420 mg, 2.8 mmol), and tetrahydrofuran (10 mL) was added 3-(3-(4-(pyridin-2-yloxymethyl)-benzyl)-isoxazol-5-yl)-pyridin-2-ylamine (1.0 g, 2.8 mmol) described in Reference Example 1, which was stirred overnight at room temperature. The reaction mixture was cooled to 0° C., and trifluoroacetic acid (17 mL) was added thereto dropwise at the same temperature. The reaction mixture was allowed to room temperature and stirred for 30 minutes. The reaction solution was concentrated under a reduced pressure, and the residue was performed gel filtration (CHP20P, Mitsubishi Kasei), eluted with water, and then methanol). The eluent was concentrated under a reduced pressure, the residue was then purified in an ODS column (water:acetonitrile:trifluoroacetic acid=1000:10:1, then 1000:200:1.2, then 1000:250:1.25, and then 1500:500:2). The eluent was concentrated under a reduced pressure, small amounts of methanol and ether were added to the residue, and the precipitated solids were collected by filtration. These were dried with forced air for 2.5 hours at 60° C. to obtain the title compound (380 mg, 29%).

$^1$H-NMR spectrum (CD$_3$OD:D$_2$O=1:1) δ (ppm): 4.08 (2H, s), 5.33 (2H, s), 5.75 (2H, d, J=10 Hz), 6.85 (1H, d, J=8.4 Hz), 6.96-7.40 (3H, m), 7.35 (2H, d, J=8.0 Hz), 7.41 (2H, d, J=8.0 Hz), 7.69-7.74 (1H, m), 8.15-8.18 (1H, m), 8.26 (1H, dd, J=1.2, 7.2 Hz), 8.35 (1H, dd, J=1.2, 6.8 Hz).

Example 2

2-Amino-1-((phosphonoxy)methyl)-3-(3-((4-((2-pyridinyloxy)methyl)phenyl)methyl)-5-isoxazolyl)-pyridinium anhydrous form (type 1)

2-Amino-1-((phosphonoxy)methyl)-3-(3-((4-((2-pyridinyloxy)methyl)phenyl)methyl)-5-isoxazolyl)-pyridinium (30 mg) was suspended in dimethylsulfoxide at 80° C., then, while stirring, water and acetic acid were added to turn the solution transparent. Then, the solution was returned to room temperature and the precipitated solid was recovered by filtration to obtain the title compound (15 mg).
$^1$H-NMR Spectrum (DMSO-$d_6$) δ (ppm): 4.07 (2H, s), 5.33 (2H, s), 5.72 (2H, d, J=9.2 Hz), 6.84-6.87 (1H, m), 6.97-7.20 (2H, m), 6.98 (1H, s), 7.35 (2H, d, J=8.4 Hz), 7.42 (2H, d, J=8.4 Hz), 7.69-7.74 (1H, m), 8.15-8.18 (1H, m), 8.25 (1H, dd, J=1.6, 7.2 Hz), 8.33-8.37 (1H, m).

Example 3

2-Amino-1-((phosphonoxy)methyl)-3-(3-((4-((2-pyridinyloxy)methyl)phenyl)methyl)-5-isoxazolyl)-pyridinium anhydrous form (type 2)

To a mixture of phosphoric acid di-tert-butyl ester chloromethyl ester (541 mg, 2.1 mmol) and tetrahydrofuran (10 mL), 3-(3-(4-(pyridin-2-yloxmethyl)-benzyl)-isoxazol-5-yl)-pyridin-2-ylamine described in Reference Example 1 (300 mg, 0.84 mmol) and sodium iodide (251 mg, 1.7 mmol) were added at 4° C., which was stirred at 4° C. for 66 hours. To the reaction mixture, under ice cooling, an aqueous solution of 2N hydrochloric acid (10 mL) was added, which was stirred at room temperature for 3.5 hours. To the reaction mixture was added ethyl acetate (10 mL) and water (10 mL), and was then extracted. The aqueous layer was separated, ethyl acetate (10 mL) was added to the aqueous layer, and then, 1N aqueous sodium hydroxide was added until a pH of the aqueous layer reached 2, which was extracted. The aqueous layer was separated, ethyl acetate (10 mL) was added to the aqueous layer, and then, 1N aqueous sodium hydroxide was added until a pH of the aqueous layer reached 2.5, which was extracted. The aqueous layer was separated, ethyl acetate (10 mL) was added to the aqueous layer, and then, 1N aqueous sodium hydroxide was added until a pH of the aqueous layer reached 3, which was extracted. The aqueous layer was separated, 1N aqueous sodium hydroxide was added until a pH of the aqueous layer reached 4, and the aqueous layer was stirred overnight at room temperature. The precipitated crystal was filtered and washed sequentially with water at pH=4 (2 mL) and ethyl acetate (2 mL) to obtain the title compound (68 mg, 17%).
$^1$H-NMR Spectrum (DMSO-$d_6$) δ (ppm): 4.08 (2H, s), 5.33 (2H, s), 5.73 (2H, d, J=9.2 Hz), 6.84-6.87 (1H, m), 6.97-7.04 (3H, m), 7.35 (2H, d, J=8.1 Hz), 7.42 (2H, d, J=8.1 Hz), 7.70-7.74 (1H, m), 8.16-8.18 (1H, m), 8.25 (1H, dd, J=1.5, 7.5 Hz), 8.34-8.36 (1H, m).

Example 4

2-Amino-1-((phosphonoxy)methyl)-3-(3-((4-((2-pyridinyloxy)methyl)phenyl)methyl)-5-isoxazolyl)-pyridinium anhydrous form (type 3)

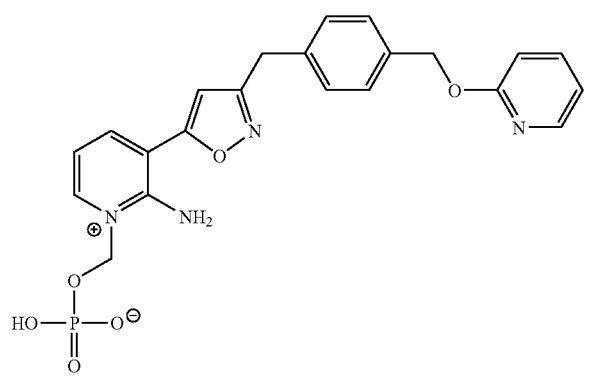 [SMILES: Nc1c(-c2cc(Cc3ccc(COc4ccccn4)cc3)no2)ccc[n+]1COP(=O)([O-])O]

To a mixture of chloromethyl di-tert-butylphosphate (6.73 g, 26 mmol) and tetrahydrofuran (22 mL), sodium iodide (6.03 g, 40 mmol) and copper powder (127 mg, 2 mmol) were added, which was stirred at room temperature. After 5 hours, 3-(3-(4-(pyridin-2-yloxymethyl)-benzyl)-isoxazol-5-yl)-pyridin-2-ylamine (7.17 g, 20 mmol) described in Example 1, toluene (20 mL), and 5N aqueous sodium hydroxide (22 mL) were added thereto, followed by stirring at room temperature. After 23 hours, a mixture of chloromethyl di-tert-butylphosphate (3.63 g, 14 mmol), sodium iodide (3.25 g, 21.5 mmol), copper powder (68 mg, 1.08 mmol), and tetrahydrofuran (12 mL), which was prepared as described above, was added thereto, which was stirred at room temperature. After 20 hours, the reaction mixture was filtered to remove the insoluble matter, and the organic layer was separated. To the resulting organic layer, 5N hydrochloric acid (22 mL) was added dropwise with an ice-water cooling bath, followed by stirring at room temperature. After 2.5 hours, ethyl acetate (35 mL) was added to the reaction mixture, and 5N aqueous sodium hydroxide was added dropwise with an ice-water cooling bath so as to adjust a pH to be from 10.5 to 11.0. The aqueous layer was separated, followed by washing with ethyl acetate (35 mL), and the same procedure was repeated twice. To the resulting aqueous layer, acetonitrile (70 mL) was added, followed by stirring at room temperature for one hour, so as to remove the insoluble matters by filtration. The aqueous layer was separated, acetonitrile (70 mL) was added thereto, followed by stirring for 30 minutes with an ice-water cooling bath. Then, the solution was stored in a refrigerator over night. Next day, the insoluble matters was removed by filtration. To the resulting aqueous layer, 5N hydrochloric acid was added dropwise, so as to adjust a pH to be 3.5. A small amount of solid of 2-Amino-1-((phosphonoxy)methyl)-3-(3-((4-((2-pyridinyloxy)methyl)phenyl)methyl)-5-isoxazolyl)-pyridinium was added into the solution, followed by stirring at room temperature over night. After 18 hours, the precipitated solid was filtrated, followed by washing with water (8 mL), water-acetonitrile (1:1, 8 mL), and acetonitrile (8 mL) in this order, and dried under a reduced pressure to obtain the crude solid (3.39 g) as a pale-brown solid.

To the resulting crude solid (3.39 g), sodium sulfite (3.39 g) and water (67.7 mL) were added followed by stirring at room temperature for 0.5 hours. After it was confirmed that the insoluble matters was not observed, acetonitrile (13.5 mL) was added thereto. Addition of 5N hydrochloric acid dropwise resulted in gradual formation of the crystal. After adjusting a pH to be 3.5, the stirring was carried out at room temperature overnight. After 17 hours, the precipitated crystal was filtrated, then washed with water-acetonitrile (1:1; 14 mL), acetonitrile (21 mL) in this order, and dried under a reduced pressure to obtain the title compound (2.98 g) as a pale-yellow crystal.
$^1$H-NMR Spectrum (DMSO-$d_6$) δ (ppm): 4.08 (2H, s), 5.33 (2H, s), 5.73 (2H, d, J=9.2 Hz), 6.84-6.87 (1H, m), 6.97-7.04 (3H, m), 7.35 (2H, d, J=8.1 Hz), 7.42 (2H, d, J=8.1 Hz), 7.70-7.74 (1H, m), 8.16-8.18 (1H, m), 8.25 (1H, dd, J=1.5, 7.5 Hz), 8.34-8.36 (1H, m).

Example 5

2-Amino-1-((phosphonoxy)methyl)-3-(3-((4-((2-pyridinyloxy)methyl)phenyl)methyl)-5-isoxazolyl)-pyridinium hydrate

To a mixture of phosphoric acid di-tert-butyl ester chloromethyl ester (43 mg, 0.17 mmol) and acetone (1 mL), 3-(3-(4-(pyridin-2-yloxmethyl)-benzyl)-isoxazol-5-yl)-pyridin-2-ylamine described in Reference Example 1 (30 mg, 0.084 mmol) and sodium iodide (25 mg, 0.17 mmol) were added at room temperature, which was stirred at 4° C. for 17 hours, then, stirred at room temperature for 3 days. To the reaction mixture, tetrahydrofuran (1 mL) and an aqueous solution of 2N hydrochloric acid (1 mL) were added at room temperature, which was stirred at room temperature for 1.5 hours. To the reaction mixture, ethyl acetate was added under ice cooling, and then, 5N aqueous sodium hydroxide was added at the same temperature until a pH of the aqueous layer reached 7.5. The aqueous layer was separated and an aqueous solution of 1N hydrochloric acid was added at room temperature until a pH of the aqueous layer reached 5. The aqueous layer was added with ethyl acetate at room temperature and was stirred overnight at the same temperature. The precipitated crystal was filtered and sequentially washed with water at pH=4 (2 mL) and isopropanol (2 mL) to obtain the title compound (9.7 mg, 23%).

$^1$H-NMR Spectrum (DMSO-$d_6$) δ (ppm): 4.07 (2H, s), 5.32 (2H, s), 5.69 (2H, d, J=9.3 Hz), 6.84-6.89 (2H, m), 6.97-7.00 (2H, m), 7.34 (2H, d, J=8.1 Hz), 7.41 (2H, d, J=8.2 Hz), 7.69-7.74 (1H, m), 8.16-8.19 (2H, m), 8.27 (1H, d, J=6.6 Hz).

Example 6

2-Amino-1-((phosphonoxy)methyl)-3-(3-((4-((2-pyridinyloxy)methyl)phenyl)methyl)-5-isoxazolyl)-pyridinium acetic acid solvate

2-Amino-1-((phosphonoxy)methyl)-3-(3-((4-((2-pyridinyloxy)methyl)phenyl)methyl)-5-isoxazolyl)-pyridinium (30 mg) was suspended in ethanol at 80° C., then, while stirring, acetic acid was added to obtain a transparent solution. Then, the solution was returned to room temperature and the precipitated solid was recovered by filtration to obtain the title compound (22 mg).

$^1$H-NMR Spectrum (DMSO-$d_6$) δ (ppm): 1.91 (3H, s), 4.08 (2H, s), 5.33 (2H, s), 5.73 (2H, d, J=9.6 Hz), 6.84-6.87 (1H, m), 6.97-7.30 (2H, m), 6.98 (1H, s), 7.35 (2H, d, J=8.0 Hz), 7.42 (2H, d, J=8.0 Hz), 7.69-7.74 (1H, m), 8.15-8.18 (1H, m), 8.25 (1H, dd, J=1.6, 7.6 Hz), 8.36 (1H, dd, J=1.6, 6.4 Hz).

Example 7

2-Amino-1-((phosphonoxy)methyl)-3-(3-((4-((2-pyridinyloxy)methyl)phenyl)methyl)-5-isoxazolyl)-pyridinium amorphous

2-Amino-1-((phosphonoxy)methyl)-3-(3-((4-((2-pyridinyloxy)methyl)phenyl)methyl)-5-isoxazolyl)-pyridinium (50 mg) was dissolved in 0.023% aqueous ammonia (25 mL), then lyophilized to obtain the title compound.

Example 8

2-Amino-1-((phosphonoxy)methyl)-3-(3-((4-((2-pyridinyloxy)methyl)phenyl)methyl)-5-isoxazolyl)-pyridinium monohydrochloride

2-Amino-1-((phosphonoxy)methyl)-3-(3-((4-((2-pyridinyloxy)methyl)phenyl)methyl)-5-isoxazolyl)-pyridinium (100 mg) was suspended in water (1 mL) and methanol (1 mL), then, while stirring, 2N hydrochloric acid (0.5 ml) was added to obtain a transparent solution. Then, acetone (13 mL) was added thereto, and the solid precipitated by subjecting to ultrasound treatment was recovered by filtration to obtain a white solid (97 mg). The resulting solid (97 mg) was dissolved in water (1 mL), acetone (19 mL) was added, and the solid precipitated by subjecting to ultrasound treatment was recovered by filtration to obtain the title compound (92 mg).

$^1$H-NMR Spectrum (DMSO-$d_6$) δ (ppm): 4.10 (2H, s), 5.33 (2H, s), 5.96 (2H, d, J=12.8 Hz), 6.84-6.87 (1H, m), 6.97-7.01 (1H, m), 6.99 (1H, s), 7.08 (1H, t, J=7.2 Hz), 7.35 (2H, d, J=8.0 Hz), 7.42 (2H, d, J=8.0 Hz), 7.70-7.75 (1H, m), 8.15-8.18 (1H, m), 8.31 (2H, d, J=7.2 Hz).

Example 9

2-Amino-1-((phosphonoxy)methyl)-3-(3-((4-((2-pyridinyloxy)methyl)phenyl)methyl)-5-isoxazolyl)-pyridinium monohydrochloride

2-Amino-1-((phosphonoxy)methyl)-3-(3-((4-((2-pyridinyloxy)methyl)phenyl)methyl)-5-isoxazolyl)-pyridinium (50 mg) was suspended in water (0.5 mL) and methanol (0.5 mL), then, while stirring, 2N hydrochloric acid (214 µL) was added to obtain a transparent solution. Then, acetone was added until the solution turned slightly turbid, which was stirred for 30 minutes. The precipitated solid was recovered by filtration to obtain the title crystal (33 mg).

$^1$H-NMR Spectrum (DMSO-$d_6$) δ (ppm): 4.10 (2H, s), 5.33 (2H, s), 5.98 (2H, d, J=12.8 Hz), 6.84-6.87 (1H, m), 6.97-7.01 (1H, m), 6.99 (1H, s), 7.07-7.11 (1H, m), 7.35 (2H, d, J=7.6 Hz), 7.42 (2H, d, J=7.6 Hz), 7.70-7.75 (1H, m), 8.15-8.18 (1H, m), 8.28-8.33 (2H, m).

Example 10

2-Amino-1-((phosphonoxy)methyl)-3-(3-((4-((2-pyridinyloxy)methyl)phenyl)methyl)-5-isoxazolyl)-pyridinium hemisulfate

2-Amino-1-((phosphonoxy)methyl)-3-(3-((4-((2-pyridinyloxy)methyl)phenyl)methyl)-5-isoxazolyl)-pyridinium (50 mg) was dissolved in water (0.5 mL) methanol (0.5 mL) and 2N sulfuric acid (52.5 mg). Acetone (approximately 0.5 mL) was added to cloud the solution, which was stirred briefly at room temperature. The cloudy solution was subjected to the ultrasound treatment, then, the precipitated solid was recovered by filtration to obtain the title crystal (38 mg).

$^1$H-NMR Spectrum (DMSO-$d_6$) δ (ppm): 4.10 (2H, s), 5.33 (2H, s), 5.94 (2H, d, J=12.4 Hz), 6.84-6.87 (1H, m), 6.97-7.01 (2H, m), 7.06-7.10 (1H, m), 7.35 (2H, d, J=8.4 Hz) 7.42 (2H, d, J=8.4 Hz), 7.70-7.75 (1H, m), 8.15-8.18 (1H, m), 8.28-8.32 (2H, m).

Example 11

2-Amino-1-((phosphonoxy)methyl)-3-(3-((4-((2-pyridinyloxy)methyl)phenyl)methyl)-5-isoxazolyl)-pyridinium mononitrate

An aqueous solution of 9% nitric acid was added to 2-amino-1-((phosphonoxy)methyl)-3-(3-((4-((2-pyridinyloxy)methyl)phenyl)methyl)-5-isoxazolyl)-pyridine (50 mg) at room temperature until a transparent solution was obtained. After concentration, water was added to the residue and insoluble matter was removed by filtration. The filtrate was concentrated, and small amounts of methanol and acetone were added to the residue. After concentration, addition of a small amount of ethanol to the residue, followed by subjecting to the ultrasound treatment, the mixture was refluxed for two minutes. After returning to room temperature, the precipitated solid was recovered by filtration to obtain the title crystal (35 mg).

$^1$H-NMR Spectrum (DMSO-$d_6$) δ (ppm): 4.10 (2H, s), 5.33 (2H, s), 5.98 (2H, d, J=13.6 Hz), 6.86 (1H, d, J=8.4 Hz), 6.97-7.01 (2H, m), 7.09 (1H, dd, J=7.6, 7.6 Hz), 7.35 (2H, d, J=8.0 Hz), 7.42 (2H, d, J=8.0 Hz), 7.70-7.75 (1H, m), 8.15-8.18 (1H, m), 8.26-8.34 (2H, m).

Example 12

2-Amino-1-((phosphonoxy)methyl)-3-(3-((4-((2-pyridinyloxy)methyl)phenyl)methyl)-5-isoxazolyl)-pyridinium monohydrobromide 2-Amino-1-((phosphonoxy)methyl)-3-(3-((4-((2-pyridinyloxy)methyl)phenyl)methyl)-5-isoxazolyl)-pyridinium (50 mg) was dissolved in water (0.5 mL), methanol (0.5 mL) and 2N hydrobromic acid (0.3 mL). A small amount of acetone was added to cloud the solution, which was left to stand still for a while. The precipitated solid was recovered by filtration to obtain the title crystal (44 mg).

$^1$H-NMR Spectrum (DMSO-$d_6$) δ (ppm): 4.10 (2H, s), 5.33 (2H, s), 5.98 (2H, d, J=13.2 Hz), 6.84-6.87 (1H, m), 6.98-7.01 (2H, m), 7.09 (1H, dd, J=7.6, 7.6 Hz), 7.35 (2H, d, J=8.0 Hz), 7.42 (2H, d, J=8.0 Hz), 7.70-7.75 (1H, m), 8.15-8.18 (1H, m), 8.27-8.33 (2H, m).

Example 13

2-Amino-1-((phosphonoxy)methyl)-3-(3-((4-((2-pyridinyloxy)methyl)phenyl)methyl)-5-isoxazolyl)-pyridinium sodium salt 2-Amino-1-((phosphonoxy)methyl)-3-(3-((4-((2-pyridinyloxy)methyl)phenyl)methyl)-5-isoxazolyl)-pyridinium (50 mg) was suspended in methanol (3 mL) and 1N aqueous sodium hydroxide (0.107 mL) was added thereto. This solution was stirred for two hours at room temperature, then, concentrated under a reduced pressure. An appropriate amount of acetone was added to this residue to let a yellow crystal precipitate. The precipitated yellow crystal was recovered by filtration and dried under a reduced pressure at room temperature to obtain the title compound (26 mg).

$^1$H-NMR Spectrum ($D_2O$) δ (ppm): 3.96 (2H, s), 5.12 (2H, s), 5.62 (2H, d, J=2.3 Hz), 6.60 (1H, s), 6.70 (1H, d, J=2.1 Hz), 6.84-6.88 (2H, m), 7.21 (2H, d, J=1.8 Hz), 7.29 (2H, d, J=1.8 Hz), 7.27-7.59 (1H, m), 7.90-7.98 (3H, m).

Example 14

2-Amino-1-((phosphonoxy)methyl)-3-(3-((4-((2-pyridinyloxy)methyl)phenyl)methyl)-5-isoxazolyl)-pyridinium hemicalcium salt 2-Amino-1-((phosphonoxy)methyl)-3-(3-((4-((2-pyridinyloxy)methyl)phenyl)methyl)-5-isoxazolyl)-pyridinium (30 mg) was suspended in water (0.5 mL), 1N aqueous sodium hydroxide (0.064 mL) was added at room temperature, followed by adding calcium acetate monohydrate (5.6 mg) in water (0.32 mL). The reaction mixture was stirred overnight at room temperature. The precipitated crystal was centrifuged to separate it from the supernatant. The crystal was washed twice with water (2 mL) and then washed once with acetone (2 mL) to obtain the title compound (12 mg).

$^1$H-NMR Spectrum ($CD_3OD/D_2O$=1/1) δ (ppm): 4.13 (2H, s), 5.29 (2H, s), 5.79 (2H, d, J=8.8 Hz), 6.85 (1H, s), 6.88-6.90 (1H, m), 7.02-7.06 (2H, m), 7.37 (2H, d, J=8.2 Hz), 7.44 (2H, d, J=8.4 Hz), 7.74-7.78 (1H, m), 8.09-8.11 (1H, m), 8.17-8.19 (1H, m), 8.23 (1H, dd, J=1.6, 7.6 Hz).

Example 15

2-Amino-1-((phosphonoxy)methyl)-3-(3-((4-((2-pyridinyloxy)methyl)phenyl)methyl)-5-isoxazolyl)-pyridinium lithium salt 2-Amino-1-((phosphonoxy)methyl)-3-(3-((4-((2-pyridinyloxy)methyl)phenyl)methyl)-5-isoxazolyl)-pyridinium (50 mg) was suspended in methanol (3 mL) and an aqueous solution of 4 m lithium hydroxide (0.027 mL) was added thereto. This mixture was stirred for 20 hours at room temperature and then concentrated under a reduced pressure. An appropriate amount of acetone was added to this residue to let a yellow crystal precipitate. The precipitated yellow crystal was recovered by filtration and dried under a reduced pressure at room temperature to obtain the title compound (35 mg).

$^1$H-NMR Spectrum ($D_2O$) δ (ppm): 3.96 (2H, s), 5.13 (2H, s), 5.59 (2H, d, J=2.2 Hz), 6.59 (1H, s), 6.71 (1H, d, J=2.1 Hz), 6.79 (1H, t, J=1.8 Hz), 6.85-6.88 (1H, m), 7.21 (2H, d, J=2.1 Hz), 7.29 (2H, d, J=2.1 Hz), 7.56-7.60 (1H, m), 7.88-7.94 (3H, m).

Example 16

2-Amino-1-((phosphonoxy)methyl)-3-(3-((4-((2-pyridinyloxy)methyl)phenyl)methyl)-5-isoxazolyl)-pyridinium potassium salt 2-Amino-1-((phosphonoxy)methyl)-3-(3-((4-((2-pyridinyloxy)methyl)phenyl)methyl)-5-isoxazolyl)-pyridinium (65 mg) was suspended in methanol (3 mL) and 1 m potassium hydroxide (0.107 mL) was added thereto. This mixture was stirred for 16 hours at room temperature and then concentrated a under reduced pressure. An appropriate amount of acetone was added to this residue to let a yellow crystal precipitate. The precipitated yellow crystal was recovered by filtration and dried under a reduced pressure at room temperature to obtain the title compound (23 mg).

$^1$H-NMR Spectrum ($D_2O$) δ (ppm): 3.96 (2H, s), 5.12 (2H, s), 5.62 (2H, d, J=2.3 Hz), 6.60 (1H, s), 6.70 (1H, d, J=2.1 Hz), 6.85-6.88 (2H, m), 7.21 (2H, d, J=2.1 Hz), 7.29 (2H, d, J=2.1 Hz), 7.55-7.60 (1H, m), 7.90-7.92 (2H, m), 7.93-7.97 (1H, m).

Example 17

2-Amino-1-((phosphonoxy)methyl)-3-(3-((4-((2-pyridinyloxy)methyl)phenyl)methyl)-5-isoxazolyl)-pyridinium phosphate 2-Amino-1-((phosphonoxy)methyl)-3-(3-((4-((2-pyridinyloxy)methyl)phenyl)methyl)-5-isoxazolyl)-pyridinium (30 mg) was suspended in methanol (0.50 mL) and water (0.50 mL), and phosphoric acid (85%, 0.11 mL) was added thereto at room temperature for dissolution. Acetone (3.0 mL)

was added dropwise to the reaction mixture, which turned into a colorless suspension. The solvent was eliminated by decantation to obtain the title compound (27 mg).

$^1$H-NMR Spectrum (DMSO-$d_6$) δ (ppm): 4.16 (2H, s), 5.38 (2H, s), 5.92 (2H, d, J=12.0 Hz), 6.87 (1H, s), 7.11 (1H, dd, J=7.0, 8.0 Hz), 7.15 (1H, d, J=8.0 Hz), 7.21 (1H, ddd, J=1.5, 6.0, 7.0 Hz), 7.40 (2H, d, J=8.0 Hz), 7.48 (2H, d, J=8.0 Hz), 8.01 (1H, ddd, J=1.5, 7.0, 9.0 Hz), 8.17-8.20 (2H, m), 8.29 (1H, dd, J=1.5, 8.0 Hz).

Example 18

2-Amino-1-((phosphonoxy)methyl)-3-(3-((4-((2-pyridinyloxy)methyl)phenyl)methyl)-5-isoxazolyl)-pyridinium N-methyl-D-glucamine salt 2-Amino-1-((phosphonoxy)methyl)-3-(3-((4-((2-pyridinyloxy)methyl)phenyl)methyl)-5-isoxazolyl)-pyridinium (30 mg) was suspended in water (1.0 mL), and N-methyl-D-glucamine (99%, 15.1 mg) and water (0.12 ml) were added thereto for dissolution. The reaction mixture was concentrated under a reduced pressure, and the residue was dissolved by adding methanol (1.0 mL). The solution was concentrated under a reduced pressure, then, acetone (4.0 mL) was added thereto, the solvent was eliminated by decantation to obtain the title compound (69%, 27 mg).

$^1$H-NMR Spectrum (DMSO-$d_6$) δ (ppm): 2.76 (3H, s), 3.15 (1H, dd, J=9.5, 13.0 Hz), 3.20 (1H, dd, J=3.5, 13.0 Hz), 3.62-3.67 (3H, m), 3.71-3.76 (2H, m), 3.79-3.82 (3H, m), 4.05-4.10 (2H, m), 4.12 (2H, s), 5.28 (2H, s), 5.79 (2H, d, J=9.0 Hz), 6.83 (1H, s), 6.88 (1H, d, J=8.5 Hz), 7.01-7.05 (2H, m), 7.36 (2H, d, J=8.0 Hz), 7.43 (2H, d, J=8.0 Hz), 7.72-7.78 (1H, m), 8.09 (1H, dd, J=1.5, 5.0 Hz), 8.17 (1H, dd, J=1.5, 6.5 Hz), 8.20 (1H, dd, J=1.5, 7.5 Hz).

Example 19

2-Amino-1-((phosphonoxy)methyl)-3-(3-((4-((2-pyridinyloxy)methyl)phenyl)methyl)-5-isoxazolyl)-pyridinium 1 lysine salt 2-Amino-1-((phosphonoxy)methyl)-3-(3-((4-((2-pyridinyloxy)methyl)phenyl)methyl)-5-isoxazolyl)-pyridinium (50 mg), L-lysine (15.6 mg) was dissolved in ethanol (2 mL) and water (1 mL) and then, the solvent was concentrated under a reduced pressure. Ethanol (1 mL) was added to the residue to suspend and recover by filtration the solid. The resulting solid was dissolved in methanol and then concentrated. A small amount of methanol was added to the residue, which was heated to 60 to 70° C. Once the solid was solved, crystal began to precipitate, which was recovered by filtration to obtain the title crystal (25 mg).

$^1$H-NMR Spectrum (DMSO-$d_6$) δ (ppm): 1.25-1.42 (4H, m), 1.53-1.62 (2H, m), 1.72-1.80 (2H, m), 2.86 (2H, t, J=8.0 Hz), 3.59 (1H, t, J=5.6 Hz), 3.95 (2H, s), 5.10 (2H, s), 5.62 (2H, d, J=9.2 Hz), 6.58 (1H, s), 6.67 (1H, d, J=8.4 Hz), 6.82-6.88 (2H, m), 7.19 (2H, d, J=7.6 Hz), 7.27 (2H, d, J=7.6 Hz), 7.53-7.58 (1H, m), 7.86-7.91 (2H, m), 7.97 (1H, d, J=7.2 Hz).

(Powder X-Ray Diffraction Measurement)

For each crystal and each amorphous obtained in the Examples, approximately 5 mg of sample was ground with a mortar, then, placed on an aluminum measurement pan and measured under the following conditions:

Apparatus used: X-ray DSC System: TTR-III (Manufactured by Rigaku Corporation)
X-ray used: CuK alpha beam
Goniometer: TTR-III horizontal goniometer
Counter: scintillation counter
Sample plate: aluminum
Target: Cu
Tube voltage: 50 kV
Tube current: 300 mA
Scanning speed: 2.000°/min
Scanning axis: 2θ/θ
Scanning range: 2θ=2.000~35.000°
Divergence slit: 0.5 mm
Vertical divergence limiting slit: 2 mm
Scattering slit: open
Sensor slit: open
Sampling width: 0.02°
Integration time: 1

The X-ray diffraction patterns of the powders for each crystal and each amorphous obtained in each of Example are shown respectively in FIG. 1 to FIG. 14, and representative peaks and relative intensities for the diffraction angle (2θ) of each crystal described above are shown in Table 1.

TABLE 1

|  | Free anhydrous form type 1 | | Free anhydrous form type 2 | | Free anhydrous form type 3 | | Free anhydrous form | |
| --- | --- | --- | --- | --- | --- | --- | --- | --- |
|  | Peak diffraction angle (2θ) | Relative intensity | Peak diffraction angle (2θ) | Relative intensity | Peak diffraction angle (2θ) | Relative intensity | Peak diffraction angle (2θ) | Relative intensity |
| Example crystal | 4.08 | 100 | 3.74 | 100 | 3.860 | 100 | 4.46 | 100 |
|  | 8.24 | 31 | 9.98 | 34 | 17.800 | 57 | 7.18 | 54 |
|  | 9.20 | 14 | 17.38 | 71 | 18.240 | 23 | 7.86 | 52 |
|  | 16.54 | 95 | 18.22 | 52 |  |  | 18.52 | 99 |
|  | 17.06 | 100 |  |  |  |  |  |  |

|  | Free acetic acid-added compound | | Free amorphous | |
| --- | --- | --- | --- | --- |
|  | Peak diffraction angle (2θ) | Relative intensity | Peak diffraction angle (2θ) | Relative intensity |
| Example crystal | 2.72 | 100 |  |  |
|  | 16.60 | 13 |  |  |
|  | 18.10 | 25 |  |  |

TABLE 1-continued

| | Monohydrochloride | | Hemisulfate | | Nitrate | | Hydrobromide | |
|---|---|---|---|---|---|---|---|---|
| | Peak diffraction angle (2θ) | Relative intensity | Peak diffraction angle (2θ) | Relative intensity | Peak diffraction angle (2θ) | Relative intensity | Peak diffraction angle (2θ) | Relative intensity |
| Example crystal | 6.26 | 67 | 7.84 | 52 | 11.88 | 83 | 12.40 | 29 |
| | 12.54 | 56 | 19.42 | 100 | 12.22 | 69 | 17.82 | 16 |
| | 20.38 | 100 | 20.24 | 59 | 16.7 | 75 | 20.20 | 100 |
| | | | 21.14 | 62 | 19.72 | 100 | | |
| | | | 21.52 | 62 | 21.5 | 75 | | |

| | Sodium salt | | ½ Ca | | Lithium | | Potassium | |
|---|---|---|---|---|---|---|---|---|
| | Peak diffraction angle (2θ) | Relative intensity | Peak diffraction angle (2θ) | Relative intensity | Peak diffraction angle (2θ) | Relative intensity | Peak diffraction angle (2θ) | Relative intensity |
| Example crystal | 2.32 | 100 | 3.78 | 56 | 2.10 | 100 | 2.10 | 100 |
| | 4.60 | 6 | 14.36 | 32 | 4.36 | 15 | 4.30 | 12 |
| | | | 15.78 | 34 | 10.88 | 7 | 10.98 | 6 |
| | | | 18.22 | 100 | | | | |
| | | | 18.44 | 60 | | | | |

The compounds according to the present invention represented by formula (I), (IA), or (IB) were used in a *Candida* systemic infection experiment with mice, which showed that there was pronounced improvement in the average number of survival days, and that the properties were excellent, especially in terms of solubility in water and stability in aqueous solutions, as well as safety and in-vivo kinetics, demonstrating that these compounds are extremely useful for the prevention or treatment of fungal infections.

1. Comparative Test Example of Solubility in Water 3-(3-(4-(Pyridin-2-yloxymethyl)-benzyl)-isoxazol-5-yl)-pyridin-2-ylamine described in Reference Example 1, which is the parent compound, and the compound of Example 1 were compared for solubility in a Britton-Robinson buffer (ionic strength: 0.3) at 25° C. Table 2 shows the results.

TABLE 2

| | Solubility (mg/mL) | | | |
|---|---|---|---|---|
| | pH 5 | pH 7 | pH 8 | pH 9 |
| Parent compound | <0.1 | <0.1 | <0.1 | <0.1 |
| Compound of Example 1 | 1.9 | 10.5 | 16.4 | >21.1 |

As can be clear from the results in Table 2, the compound of Example 1 has markedly higher solubility in water than does the parent compound over various pH regions.

Pharmacological Test Examples

2. Experimental Systemic Candidal Infection Model in Mice (1) Preparation of Fungal Inoculant A standing culture of *C. albicans* E81022 strain was carried out for 24 hours at 35° C. in sabouraud dextrose agar medium (Difco), and the recovered fungal cells were suspended in sterile physiological saline (Otsuka Pharmaceutical). By counting the fungal number on cytometry plate, the suspension was diluted to $2 \times 10^7$ cells/mL with sterilized physiological saline to serve fungal inoculum.

(2) Infection

The fungal inoculum was used in an amount of 0.2 mL to inoculate the mice in the tail vein ($4 \times 10^6$ cells/mouse).

(3) Preparation of Agent Solution, and Treatment

The compound of Example 1 was dissolved in concentrations of 13 mg/mL and 3.25 mg/mL with a 50 mM glycine buffer with a pH of 10 (Wako Pure Chemicals), these solutions were then diluted 10 times with 5% glucose (Otsuka Pharmaceutical). At 0.5 and 9 hours after infection, 0.2 mL of the agent solution was administered into a tail vein of the mice. The agent concentrations were 2.5 and 10 mg/kg (calculated as the active form). The number of animals in one group was 5 animals.

(4) Evaluation of Effect

The protective effect was determined by observing life/death until 14 days after infection and calculating the mean survival days. The protective effect on the systemic candidal infection was measured for the compound of Example 1 by the method described in section 2. As a result, as shown in Table 3, the mice administered with the compound of Example 1 survived for a longer time as compared to the untreated group, and the compound of Example 1 have found to demonstrate an in vivo protective effect.

TABLE 3

| Average Number of Survival Days in *Candida* Infection Experiment | |
|---|---|
| Administration Group | Mean Survival Days |
| Control | 2.4 |
| Compound of Example 1: 3.25 mg/kg (calculated as active form: 2.5 mg/kg) | 7.4 |
| Compound of Example 1, 13 mg/kg (calculated as active form: 10 mg/kg) | 12.8 |

Note that, in vitro, the compound of Example 1 demonstrated an activity of only 1/100 or less with respect to the parent compound (Reference Example 1). From these results, the compound of Example 1 was shown to act as a prodrug in vivo.

3. Pharmacokinetic Evaluation in Mice (1) Preparation of Administration Solution The compound of Example 1 was dissolved in a concentration of 0.45 mg 1 mL with a 50 mM glycine buffer with a pH of 9 (Wako Pure Chemicals), and the active form was dissolved in a concentration of 0.45 mg/mL in a 10 mM hydrochloric acid solution (Wako Pure Chemicals) containing 5% glucose (Otsuka Pharmaceutical).

(2) Administration, and Sampling of Blood and Plasma

Using five-week-old female ICR mice (Charles River Japan), with the number of mouse in one group being 2 mice, the compound according to the present invention and an active form thereof were administered into the tail vein in a dose of 3 mg/kg. The tail vein was punctured 0.25, 0.5, 1.5, 3, 5, and 8 hours after administration, and blood was collected with a heparin-treated pipette. The blood samples were put into sampling tubes and stored under ice cooling. Thereafter, they were centrifuged for 5 minutes at 10,500×g and at 4° C. The plasma thus obtained was accurately divided into 5 μL amounts and stored at −20° C. until they were analyzed.

(3) Plasma Concentration Measurement Method

The plasma concentrations of the compound of Example 1 and the active form thereof were measured using a liquid chromatography mass spectrometer (LC-MS), and quantified by internal standard method. Imipramine hydrochloride (Sigma) was dissolved in a mixed solution of acetonitrile and methanol (1:1) so that the concentration would be 0.5 μmol/L, to prepare an internal standard substance solution (IS solution). The plasma was melted, 50 μL of IS solution was then added thereto and mixed, and this was centrifuged (deproteinated) for 10 minutes at 1500×g and at 4° C., the supernatant was then analyzed by LC-MS (Waters). In the chromatogram thus obtained, the surface area of the peaks for the compound of Example 1 and the active form thereof (the parent compound of the compound of Example 1), and of the peak corresponding to the internal standard substance, were analyzed by MassLynx (Waters), and the concentration of the compound included in the plasma was calculated by internal standard method.

Figure 15:
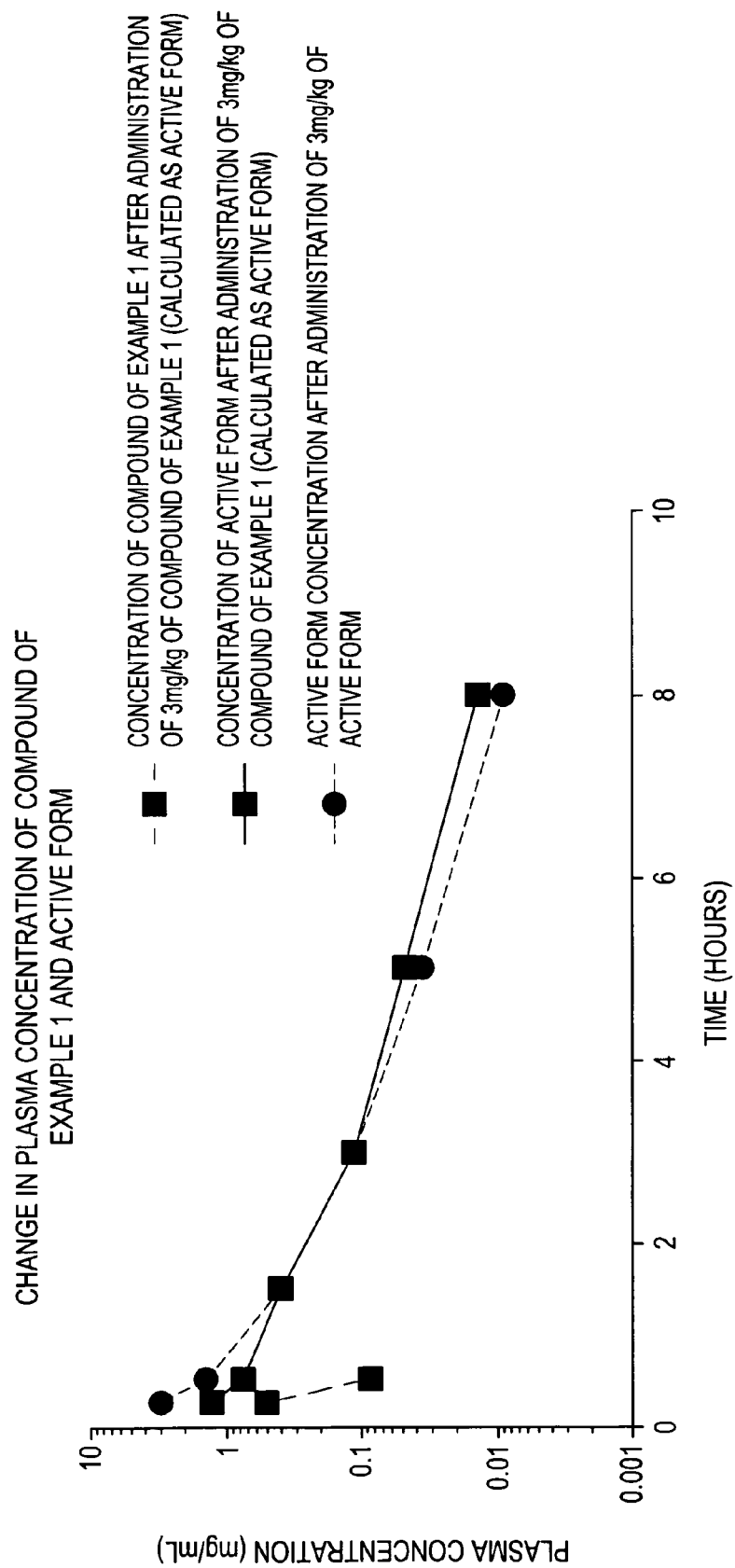
FIG. 15 shows a drawing of results of measuring the plasma concentration of the compound of Example 1 and the active form (the parent compound of the compound of Example 1) measured by pharmacokinetic evaluation in mice in one aspect of the present invention.

The plasma concentration was measured for the compound of Example 1 and the active form by the method described in section 3. As a result, as shown in FIG. 15, the plasma concentration of the compound of Example 1 decreased quickly after administration, and the plasma concentration of the active form increased quickly from immediately after administration of the compound of Example 1, exhibiting a plasma concentration change that was similar to that at the time of active form administration. The above suggests that the compound of Example 1 is rapidly converted into the active form in the bodies of the mice.

4. Pharmacokinetic Evaluation in Monkeys (1) Preparation of Administration Solution The compound of Example 1 was dissolved in a concentration of 1.5 mg/mL with a 50 mM glycine buffer with a pH of 9 (Wako Pure Chemicals), and the active form (the parent compound thereof) was dissolved in a concentration of 1 mg/mL in a 10 mM hydrochloric acid solution (Wako Pure Chemicals) containing 5% glucose (Otsuka Pharmaceutical).

(2) Administration, and Sampling of Blood and Plasma

Using five-year-old male crab-eating macaques (GFD), with the number of monkeys in one group being 2 monkeys, the compound of Example 1 and the active form thereof were administered into a radial cutaneous vein in a dose of 0.4 mg/kg. Blood was collected from the radial cutaneous vein 0.25, 0.5, 1, 2, 4, and 6 hours after administration using a heparin-treated syringe. The blood samples were put into sampling tubes and stored under ice cooling, they were then centrifuged for 5 minutes at 10,500×g and at 4° C. The plasma thus obtained was accurately divided into 5 μL amounts and stored at −20° C. until they were analyzed.

(3) Plasma Concentration Measurement Method

The plasma concentrations of the compound of Example 1 and the active form thereof were measured using a liquid chromatography mass spectrometer (LC-MS), and quantified by internal standard method. Imipramine hydrochloride (Sigma) was dissolved in a mixed solution of acetonitrile and methanol (1:1) so that the concentration would be 0.5 μmol/L, to prepare an internal standard substance solution (IS solution). The plasma was melted, 200 μL of IS solution was then added thereto and mixed, and this was centrifuged (deproteinated) for 10 minutes at 1500×g and at 4° C., the supernatant was then analyzed by LC-MS (Waters). In the chromatogram thus obtained, the surface area of the peaks for the compound of Example 1 and the active form compound, and of the peak corresponding to the internal standard substance, were analyzed by MassLynx (Waters), and the concentration of the compound included in the plasma was calculated by internal standard method.

Figure 16:
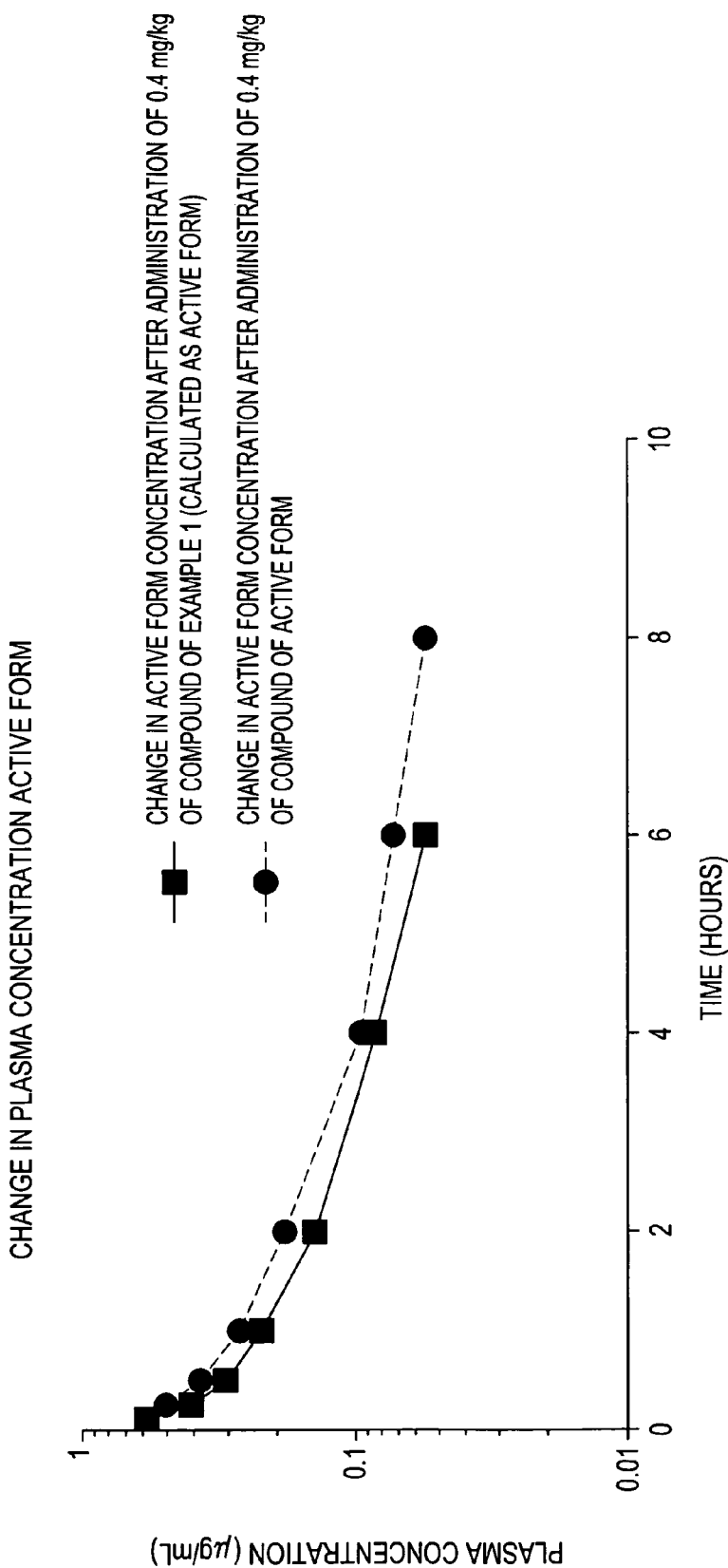
FIG. 16 shows a drawing of results of measuring the plasma concentration of the compound of Example 1 and the active form (the parent compound of the compound of Example 1) measured by pharmacokinetic evaluation in monkeys in other aspect of the present invention.

The plasma concentration of the active form after administration of the compound of Example 1 was measured by the method described in section 4. As a result, as shown in FIG. 16, the plasma concentration of the active form immediately after administration of the compound of Example 1 rose quickly, exhibiting a plasma concentration change similar to that at the time of active form administration. The plasma concentration of the compound of Example 1 was under the detection limit. The above suggests that the compound of Example 1 is quickly converted into the active form inside the bodies of the monkeys.

The present application is based on an U.S. Provisional Patent Application No. 61/017,053 filed with the United States Patent and Trademark Office on Dec. 27, 2007 and a Japanese Patent Application (Japanese Patent Application No. 2007-336977) filed with the Japan Patent Office on Dec. 27, 2007, the contents of which are incorporated herein by reference.

INDUSTRIAL APPLICABILITY

According to the present invention, the compound according to the present invention represented by Formula (I), (IA), or (IB): 1) acts against the onset, development and persistence of infections by inhibiting fungal GPI biosynthesis, thereby inhibiting expression of cell wall proteins and blocking cell wall assembly while preventing the fungus from attaching to cells so that the pathogen cannot become pathogenic, and 2) is superior in terms of physical properties, and particularly its solubility in water, its stability in an aqueous solution, and its safety and in-vivo kinetics, making the above compounds extremely useful as a preventive or therapeutic agent for fungal infections.

What is claimed is:

1. A compound of 2-amino-1-((phosphonooxy)methyl)-3-(3-((4-((2-pyridinyloxy)methyl)phenyl)methyl)-5-isoxazolyl)-pyridinium represented by:

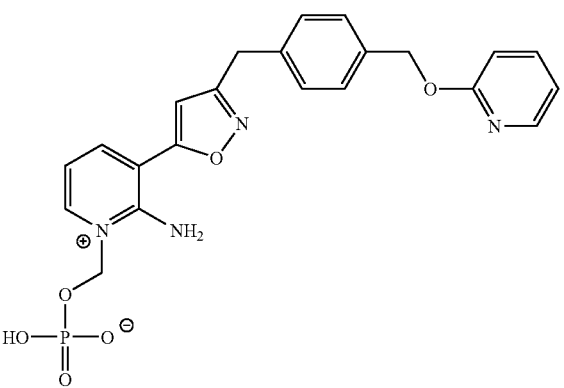 [SMILES: Nc1c(-c2cc(Cc3ccc(COc4ccccn4)cc3)no2)ccc[n+]1COP(=O)([O-])O]

or a salt thereof

2. A pharmaceutical composition comprising the compound or the salt thereof according to claim 1.

3. A method for treating a fungal disease by administering a pharmaceutically effective amount of the compound or the salt thereof according to claim 1.

* * * * *